(12) United States Patent
Heldman et al.

(10) Patent No.: US 11,367,519 B1
(45) Date of Patent: Jun. 21, 2022

(54) SYSTEMS AND METHODS FOR PRECISION OR PERSONAL PHARMACEUTICAL DOSING

(71) Applicants: Dustin A. Heldman, Shaker Heights, OH (US); Brian Kolkowski, Leroy, OH (US); Mark Pennington, Medina, OH (US)

(72) Inventors: Dustin A. Heldman, Shaker Heights, OH (US); Brian Kolkowski, Leroy, OH (US); Mark Pennington, Medina, OH (US)

(73) Assignee: Great Lakes NeuroTechnologies Inc., Cleveland, OH (US)

( * ) Notice: Subject to any disclaimer, the term of this patent is extended or adjusted under 35 U.S.C. 154(b) by 492 days.

(21) Appl. No.: 16/039,581

(22) Filed: Jul. 19, 2018

(51) Int. Cl.
| | |
|---|---|
| *G16H 20/17* | (2018.01) |
| *A61B 5/11* | (2006.01) |
| *A61B 5/00* | (2006.01) |
| *A61M 5/142* | (2006.01) |
| *A61M 5/172* | (2006.01) |

(52) U.S. Cl.
CPC .............. *G16H 20/17* (2018.01); *A61B 5/11* (2013.01); *A61B 5/486* (2013.01); *A61B 5/4839* (2013.01); *A61B 5/7246* (2013.01); *A61B 5/7275* (2013.01); *A61M 5/142* (2013.01); *A61M 5/1723* (2013.01); *A61M 2205/3303* (2013.01); *A61M 2205/505* (2013.01); *A61M 2230/63* (2013.01)

(58) Field of Classification Search
CPC ................ A61M 5/142; A61M 5/1723; A61M 2205/3303; A61M 2205/505; G16H 20/10; G16H 20/17; G16H 20/13; G16H 20/70; G06F 19/34; G06F 19/3468; A61B 5/1104; A61B 5/4836; A61B 5/4839; A61B 5/486; A61B 5/7275
See application file for complete search history.

(56) References Cited

U.S. PATENT DOCUMENTS

| | | | |
|---|---|---|---|
| 6,766,219 B1 * | 7/2004 | Hasey ................... | A61J 7/0084 221/11 |
| 2002/0087114 A1 * | 7/2002 | Hartlaub ........... | A61M 5/14276 604/65 |
| 2005/0277911 A1 * | 12/2005 | Stewart ............. | A61M 5/14228 604/890.1 |

(Continued)

*Primary Examiner* — Nilay J Shah
(74) *Attorney, Agent, or Firm* — Brian Kolkowski

(57) ABSTRACT

Systems and methods are disclosed for providing recommended doses and instructions for pharmaceutical treatments by measuring physiological and/or electrophysiological signals from a subject and providing recommended doses and instructions of pharmaceuticals based at least in part on the measured signals. Further, the recommended doses and instructions are based at least in part on a subject's disease (s), disorder(s), or injuries and/or symptom(s) of such, and/or side effects of medications or treatments the subject is receiving. The recommended doses and instructions are personally tailored to the subject to precisely and personally address the subject's needs, and may be based in part on correlation with database(s) comprising historical data of the subject and/or other subjects to treat the subject's movement disorders, injuries to the body or brain, cognitive diseases and disorders, sleep diseases and disorders, chronic pain, or other conditions.

8 Claims, 10 Drawing Sheets

(56) References Cited

U.S. PATENT DOCUMENTS

| | | | |
|---|---|---|---|
| 2006/0031094 A1* | 2/2006 | Cohen | G16H 20/10 |
| | | | 705/2 |
| 2006/0177381 A1* | 8/2006 | Brooks-Korn | A61K 31/485 |
| | | | 424/10.1 |
| 2013/0123666 A1* | 5/2013 | Giuffrida | A61B 5/0024 |
| | | | 600/595 |
| 2016/0228640 A1* | 8/2016 | Pindado | G06F 16/24 |

* cited by examiner

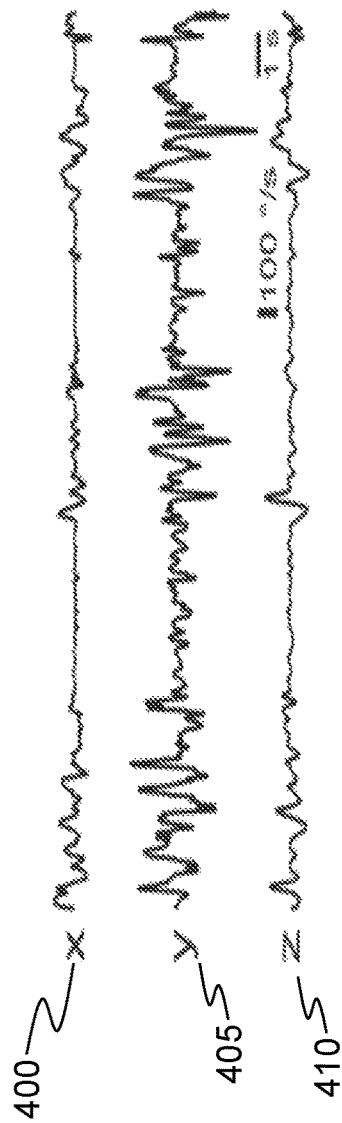

FIG. 4

| DOMAIN | OUTCOME MEASURE |
|---|---|
| Physical Activity | • Percentage of the day spent moving<br>• Relationship between active-rest periods<br>• Percentage of day in different body postures |
| Mobility and Participation | • Leg swing velocity<br>• Stride variability<br>• Double limb support time<br>• Number and duration of trips and stops*<br>• Percentage of time spent at and away from home* |
| Sleep Quality | • Amount of time spent asleep<br>• Number of times awoken<br>• Sleep efficiency |
| Speech | • Alternating motion rate+ |

FIG. 5

SYSTEMS AND METHODS FOR PRECISION OR PERSONAL PHARMACEUTICAL DOSING

BACKGROUND OF THE INVENTION

1. Field of the Invention

The present invention relates to systems and methods for providing recommended doses and instructions for pharmaceutical treatments. More particularly, the present invention relates to systems and methods for measuring physiological and/or electrophysiological signals from a subject and providing recommended doses and instructions of pharmaceuticals based at least in part on the measured signals. Further, the recommended doses and instructions are based at least in part on a subject's disease(s), disorder(s), or injuries and/or symptom(s) of such, and/or side effects of medications or treatments the subject is receiving. The recommended doses and instructions are personally tailored to the subject to precisely and personally address the subject's needs, and may be based in part on correlation with database(s) comprising historical data of the subject and/or other subjects to treat the subject's movement disorders, injuries to the body or brain, cognitive diseases and disorders, sleep diseases and disorders, chronic pain, or other conditions.

2. Technical Background

The present invention is directed to providing precise and personalized dosing and instructions for pharmaceutical treatment of diseases, disorders, or injuries, symptoms of such diseases, disorders, or injuries, or side effects to treatment for such diseases, disorders, or injuries. Diseases, disorders, or injuries in the scope of the present invention may include movement disorders, injuries to the body or brain, cognitive diseases and disorders, sleep diseases and disorders, chronic pain, and the like. Movement disorders may be congenital or otherwise naturally occurring and progressing, or may be the result of injury. Movement disorders include, but are not limited to Parkinson's disease (PD), parkinsonism, essential tremor, tremor, cerebral palsy (CP), multiple sclerosis (MS), chorea, athetosis, hemiballismus, coordination disorders, dystonia and cervical dystonia, ataxia, Huntington's disease, myoclonus, progressive subranuclear palsy (PSP), tics, Tourette Syndrome, Wilson's disease, and the like. Injuries to the body or brain include, but are not limited to stroke, traumatic brain injury (TBI), mild traumatic brain injury (mTBI), or other injuries that result in movement or cognitive impairment. Cognitive diseases and disorders include, but are not limited to, Alzheimer's disease, dementia, depression, mood disorders, obsessive-compulsive disorder, memory impairments, antisocial disorders, and the like. Sleep disorders include, but are not limited to, restless leg syndrome, narcolepsy, sleep walking (somnambulating), obstructive sleep apnea, insomnia, excessive daytime sleepiness, and the like. Chronic pain is typically defined as pain persisting beyond a period of normal tissue healing, and/or experienced every day for 3 months or more, and can be the result of some injury or may be naturally occurring. The present invention is further directed to providing recommendations for dosing and instructions for pharmaceutical treatment of many symptoms and treatment side effects of the above types of diseases, disorders, and injuries including, but not limited to, tremor, bradykinesia, rigidity, dyskinesia, gait and/or balance disturbances, memory impairment, cognitive impairment, pain, sleep disturbances, and many others known to those skilled in the art of treatment of each of the types of diseases, disorders, or injuries within the scope of the present invention.

Movement disorders resulting from brain or spinal cord injury, or abnormalities affect millions of individuals worldwide. These movement disorders can be the result of stroke, cerebral palsy (CP), Parkinson's disease (PD) and the like. Since these injuries or abnormalities can affect most parts of the brain or the spinal cord, the possible results are numerous. Effects can include motor paralysis, sensory disturbances, language difficulties, memory problems, tremor, and issues with swallowing or slurred speech. These disorders can also result in loss of motor control of the individual's extremities, including paralysis or weakness, abnormal muscle tone, abnormal posture, abnormal movement synergies and loss of coordination. Many individuals that experience a movement disorder develop a physical disability that affects activities of daily living including eating, dressing and personal hygiene.

Two of the most prevalent treatment methods currently implemented for alleviating movement disorder symptoms are electrical stimulation, particularly deep brain stimulation (DBS) and functional electrical stimulation (FES), and the use of pharmaceutical treatments (i.e., medications, drugs). The effectiveness of both electrical stimulation and pharmaceutical treatment vary widely depending on a patient's individual symptoms and the causes thereof. Furthermore, the efficacy of each treatment method generally varies greatly throughout the day, as well as the life of the treatment due to numerous environmental and circumstantial factors that play a role in the onset of such symptoms.

Additional treatments may include surgery and physiotherapy which are used to help counter the effects of movement disorders. Little evidence, however, exists of their efficacy. Optionally, occupational and physical therapy contributes to the functional recovery of patients suffering from movement disorders. Research has shown that forced use through repetitive motor activity may provide the basis for motor learning and functional recovery. For example repetitive movement execution or repetitive sensorimotor training may be of great benefit for functional outcomes of motor rehabilitation of the arm and hand. Physical therapy has been found to lead to enhancement of motor function if the individual performs voluntary motor activities with that arm. Methods used by rehabilitation therapists to effectively stimulate functional plasticity and motor recovery include active/passive range of motion, bilateral training, forced use, and constraint induced therapy.

Both simple, isolated, single joint movements and complex movement tasks improve motor recovery. Repetitive training of complex movements has been found to provide significant improvement of motor function in distal and proximal affected upper extremities. Grip strength, another important requirement for daily living, is also significantly improved. The repetitive execution of complex motor movements accelerates and supports functional recovery. Increasing the amount of time spent as well as using behavioral methods to encourage motor learning helps improve function for those individuals suffering from a movement disorder.

Deep brain stimulation (DBS) and functional electrical stimulation (FES) are two forms of electrical stimulation that have been used by clinicians to help counter the effects of certain movement disorders. For example, DBS is the stimulation of target areas of the central nervous system to affect therapeutic benefit. Such stimulation has been accomplished with, for example, implanted electrodes that deliver electrical stimulation to target brain regions. Although the exact neurological mechanisms by which DBS therapies succeed are complex and are not yet fully understood, such therapies have proven effective in treating Parkinson's disease motor symptoms (such as tremor, bradykinesia, rigidity, and gait/balance disturbances), and investigation into the use of DBS for the treatment of this and other neurological and mental health disorders, including major depression, obsessive-compulsive disorder, tinnitus, obesity, criminal tendencies, and antisocial disorders, is ongoing.

Functional electrical stimulation (FES) has been found to be advantageous for individuals suffering from CP partially because it is non-invasive and causes minimal side effects. FES stimulates the muscles to create a contraction. Some individuals with CP have paralyzed muscles while others with early acquired motor deficits can have difficulty producing selective movements in an affected extremity due to a form of apraxia caused by defective motor planning in early infancy. Therefore, a muscle normally required for a task, but inactive due to CP could potentially be included during therapy using functional electrical stimulation. Additionally, utilizing functional electrical stimulation at the sensory level helps the individual to localize the muscle they are trying to use for a particular task.

During electrical stimulation, electrical pulses characterized by amplitude (volts/amps), frequency (Hz), and pulse width (microseconds) are regulated by a pulse generator placed beneath the skin on the chest or worn externally. The pulse generator typically includes a battery and circuitry for telemetered communication with an external programming device used to adjust, or "tune," lead stimulation parameters, which may include stimulation frequency, amplitude, pulse width (or wavelength), and contact configuration (that is, the selection of which electrodes are utilized from among the electrodes available on a lead, and, if two or more electrodes are active, the relative polarity of each). These parameters are initially set during implantation surgery and are then further fined-tuned in the outpatient clinic or in a doctor's office following surgery to maximize therapeutic benefit and minimize undesirable stimulation-induced side effects.

While various pharmaceutical agents exist for treatment of movement disorder symptoms, oral administration of L-3,4-dihydroxyphenylalanine ("levodopa" or "L-DOPA") is presently the most common, particularly for PD, and will thus be the focus of the examples set forth herein. Levodopa is a dopamine precursor molecule that alleviates symptoms by crossing the blood brain barrier and being subsequently converted into dopamine. During treatment, levodopa is typically taken orally by a subject several times per day at intervals specified by a physician. The dosage, taken at such intervals, allows the level of levodopa in the blood to remain somewhat constant throughout the day. However, physiological differences between subjects means that there will be no single dosage of levodopa that will be effective for all subjects. It will be appreciated that this same effect is also observed in pharmaceutical treatment of subjects with various other movement disorders besides PD.

This lack of uniformity among subjects and the temporal variation of levodopa efficacy in treating PD raise a need for a method and/or device that allows a physician to more optimally customize a subject's drug regimen or protocol based on the drug's effect on a specific subject at specific times and under a subject's specific circumstances. Automated medication titration and delivery systems can help physician's achieve some of these goals, however, the current technology is subject to a number of problems, for example, the devices cannot be controlled in real-time to account for a patient's dyskinesias and are limited to a single medication.

While electrical stimulation and pharmaceutical treatments can improve functional outcomes for patients with movement disorders, these treatments can require frequent returns and long stays in a treatment center. What is needed is a system and/or method that allows individuals to customize their therapy outside a treatment center. What is also needed is a system and/or method that allows individuals to continue and improve treatment without the need for a clinician to be available to apply the treatment. What is still further needed is a system and/or method that allows for intensive home treatment of individuals affected with movement disorders.

It is therefore an object of the present invention to provide a system and method for treating individuals with movement disorders without needing a clinician to apply the treatment. It is still another object of the present invention to provide a system, which provides functional recovery. It is still another object of the present invention to provide a system and method that provides feedback and recommendations to the clinician providing a patient with customized and adaptive treatment. It is still further another object of the present invention to provide precise and personalized treatment recommendations for each individual subject tailored to each subject's personal conditions and needs.

Chronic pain affects as much as 30% of the population and is defined as pain persisting beyond a period of normal tissue healing, and/or experienced every day for 3 months or more. Chronic low back pain (CLBP) affects approximately one quarter of adults in any given year and is the most common cause of physical disability in the working population. While not a disease, people with CLBP report that most, if not all, aspects of their lives are significantly affected by their pain, and it can have a similar impact on health-related quality of life (QOL) as liver disease and cancer. Chronic pain has a significant economic impact, with an estimated health care cost of $300 billion per year. The pathophysiology of pain is not always well defined, which contributes to inconsistent patient outcomes, especially considering the reliance on patient-reported subjective outcomes. While the patient's perspective is an integral component, both treatment and research into chronic pain are greatly compromised by the fact that there is no objective diagnostic test that can complement the subjective assessment of chronic pain conditions.

Spinal cord stimulation (SCS) is the most common form of neuromodulation used in managing chronic back or leg pain, with more than 14,000 SCS implantations performed worldwide each year. SCS is a minimally invasive treatment in which electrodes are placed in the epidural space and masks pain by substituting it with paresthesia. A permanent implant is typically preceded by a trial evaluation during which the electrodes are placed percutaneously and connected to a small external stimulator. SCS has a success rate of about 50%, with sustained decreases pain intensity scores, functional improvement, and decreased medication usage. Recent evidence from off-label studies of deep brain stimulation, a more invasive form of neuromodulation, supports its use in treating forms of neuropathic pain and depression that are resistant to conventional treatments. An emerging form of neuromodulation which uses high frequency stimulation to block nerve conduction has shown promise for blocking pain transmission and is being commercialized for amputation pain. Despite these advances in the technological aspects of therapy, efficacy is universally judged by a reduction in subjective patient-reported severity, which is an important yet incomplete assessment of pain's impact on quality of life.

A number of validated tools, such as the visual analog scale and numerical rating scale and patient global impression scale, have been used to assess pain intensity. There are also a number of measures that assess the impact back pain has on function and QOL, including the pain self-efficacy scale and Oswestry disability index, but they have several limitations including: 1) they rely on self-reporting and recall, which are subjective and prone to bias, 2) they cannot be used in subjects with cognitive or communication impairments, and 3) they are not electronically time stamped and fail to capture the dynamic nature of pain and its impact on daily life.

Functional brain imaging (e.g., fMRI) has been proposed as an objective biomarker for pain intensity and perception. While imaging may eventually accurately capture pain perception, scans in the lab will not measure the effect of pain on QOL and independence, which are arguably the most important outcomes.

A number of sensors and sensing modalities are known to be useful in the measurement of pain, typically physiological signal sensors used to measure bioelectrical signals from a subject, for example EEG sensors. However, many other sensors and sensing modalities are not typically known to be useful in applications for measuring a subject's pain. For example, movement sensors such as accelerometers, gyroscopes, magnetometers, resistive bend sensors and the like, designed to measure a subject's external body motion, are not known in the art to be generally useful for measuring a subject's pain. Similarly, other sensors and sensing modalities such as audio and speech sensors, sleep sensors, video sensors, global positioning (GPS) sensors, skin conductance sensors, pulse oximeters, and even some physiological signal sensors are not generally known to be useful for pain measurement.

It is therefore an object of the present invention to: 1) effectively combine kinematic data from accelerometers and gyroscopes, and other sensor data related to physiological characteristic affected by chronic pain, with location, diary, and speech information obtained through data acquisition devices including, for example, smart phones, tablet computers, laptop computers, and the like, into a powerful research tool; 2) provide objective measures in the clinical market to quantify and optimize therapeutic response to treatments; and 3) particularly optimize pharmaceutical treatment for chronic pain to help minimize the need for advanced therapy modalities requiring surgery and stimulation. It is further an object of the present invention to provide accurate, objective monitoring of behavioral patterns of physical activity with sensors that may provide an accurate, objective appraisal of the impact of pain on the physical, social, and emotional functioning that complements standard patient-reported outcome measures. Still further, it is an object of the present invention that the method, system or device can be used to help manage chronic pain patients, enabling them to capture objective data related to therapeutic response. In addition to chronic pain, it is an object of the present invention that the method, system or device will have implications for other monitoring disorders (e.g., depression) that affect behavioral patterns and rely on subjective patient self-assessment. It is yet a further object of the present invention that the method, system or device could be adapted in other programs as a telemedicine platform for delivering behavioral therapy, which has been shown to be a potential mechanism for expanding health care access for pain patients.

Dementia, in general, is a decline in mental ability that is typically severe enough to interfere with a person's daily life. Dementia is generally not considered a disease in and of itself, but rather is an overall term used to describe a wide range of symptoms associated with the decline of mental ability, including memory and other thinking skills in a manner that reduces a person's ability to perform everyday activities. There are numerous types and degrees of dementia, including: Alzheimer's disease, vascular dementia, dementia with Lewy bodies (DLB), mixed dementia, dementia related to Parkinson's disease, frontotemporal dementia, and dementia related to Creutzfeldt-Jakob disease, normal pressure hydrocephalus, Huntington's disease, or Wernicke-Korsakoff Syndrome. Alzheimer's disease is the most common type of dementia, accounting for approximately 60% to 80% of dementia cases. Vascular dementia, which is a type that occurs following a stroke, is the second most common type of dementia. Dementia with Lewy bodies (DLB) is another type wherein subjects often have memory loss and thinking problems common in Alzheimer's, but are more likely than people with Alzheimer's to have initial or early symptoms such as sleep disturbances, well-formed visual hallucinations, and slowness, gait imbalance or other parkinsonian movement features. Lewy bodies are abnormal aggregations (or clumps) of the protein alpha-synuclein. When they develop in a part of the brain called the cortex, dementia can result. Alpha-synuclein also aggregates in the brains of people with Parkinson's disease, but the aggregates may appear in a pattern that is different from dementia with Lewy bodies. The brain changes of dementia with Lewy bodies alone can cause dementia, or they can be present at the same time as the brain changes of Alzheimer's disease and/or vascular dementia, with each abnormality contributing to the development of dementia. When this happens, the individual is said to have mixed dementia. In mixed dementia abnormalities linked to more than one cause of dementia occur simultaneously in the brain. Recent studies suggest that mixed dementia is more common than previously thought. With respect to dementia related to Parkinson's disease, as Parkinson's disease progresses, it often results in a progressive dementia similar to dementia with Lewy bodies or Alzheimer's. Problems with movement are common symptoms of the disease. If dementia develops, symptoms are often similar to dementia with Lewy bodies. Alpha-synuclein clumps are likely to begin in an area deep in the brain called the substantia nigra. These clumps are thought to cause degeneration of the nerve cells that produce dopamine. As for dementia related to Huntington's disease, Huntington's disease is a progressive brain disorder caused by a single defective gene on chromosome 4, and may present symptoms including abnormal involuntary movements, a severe decline in thinking and reasoning skills, and irritability, depression and other mood changes. The gene defect causes abnormalities in a brain protein that, over time, lead to worsening symptoms. Still many other sources or conditions exist as causes for dementia, such as thyroid issues and vitamin deficiencies. The greatest known risk factor is increasing age, and the majority of people with Alzheimer's or dementia are 65 and older. But Alzheimer's is not just a disease of old age. Approximately 200,000 Americans under the age of 65 have younger-onset Alzheimer's disease (also known as early-onset Alzheimer's). Alzheimer's is a progressive disease, where the dementia symptoms gradually worsen over a number of years. In its early stages, memory loss is mild, but with late-stage Alzheimer's, individuals lose the ability to carry on a conversation and respond to their environment. Alzheimer's is the sixth leading cause of death in the United States. Those with Alzheimer's live an average of eight years after their symptoms become noticeable to others, but survival can range from four to 20 years, depending on age and other health conditions. There is currently no known cure for Alzheimer's or most other forms of dementia, but there are treatments available. Although current Alzheimer's treatments cannot stop Alzheimer's from progressing, they can temporarily slow the worsening of dementia symptoms and improve quality of life for those with Alzheimer's and their caregivers.

In general, dementia is caused by damage to brain cells. This damage interferes with the ability of brain cells to communicate with each other. When brain cells cannot communicate normally, thinking, behavior and feelings can be affected. The brain has many distinct regions, each of which is responsible for different functions (for example, memory, judgment and movement). When cells in a particular region are damaged, that region cannot carry out its functions normally. Different types of dementia are associated with particular types of brain cell damage in particular regions of the brain. For example, in Alzheimer's disease, high levels of certain proteins inside and outside brain cells make it hard for brain cells to stay healthy and to communicate with each other. The brain region called the hippocampus is the center of learning and memory in the brain, and the brain cells in this region are often the first to be damaged. That's why memory loss is often one of the earliest symptoms of Alzheimer's. While most changes in the brain that cause dementia are permanent and worsen over time, thinking and memory problems caused by the following conditions may improve when the condition is treated or addressed: depression, medication side effects, excess use of alcohol, thyroid problems, and vitamin deficiencies.

There is currently no one test to determine if someone has dementia. Doctors diagnose Alzheimer's and other types of dementia based on a careful medical history, a physical examination, laboratory tests, and the characteristic changes in thinking, day-to-day function and behavior associated with each type. Doctors can determine that a person has dementia with a high level of certainty. But it's harder to determine the exact type of dementia because the symptoms and brain changes of different dementias can overlap. In some cases, a doctor may diagnose "dementia" and not specify a type. If this occurs it may be necessary to see a specialist such as a neurologist or gero-psychologist.

Treatment of dementia depends on its cause. In the case of most progressive dementias, including Alzheimer's disease, there is no cure and no treatment that slows or stops its progression. But there are drug treatments that may temporarily improve symptoms. The same medications used to treat Alzheimer's are among the drugs sometimes prescribed to help with symptoms of other types of dementias. Non-drug therapies can also alleviate some symptoms of dementia. Ultimately, the path to effective new treatments for dementia is through increased research funding and increased participation in clinical studies. Right now, volunteers are urgently needed to participate in more than 180+ actively enrolling clinical studies and trials about Alzheimer's and related dementias Some risk factors for dementia, such as age and genetics, cannot be changed. But researchers continue to explore the impact of other risk factors on brain health and prevention of dementia. Some of the most active areas of research in risk reduction and prevention include cardiovascular factors, physical fitness, and diet. Cardiovascular risk factors: Your brain is nourished by one of your body's richest networks of blood vessels. Anything that damages blood vessels anywhere in your body can damage blood vessels in your brain, depriving brain cells of vital food and oxygen. Blood vessel changes in the brain are linked to vascular dementia. They often are present along with changes caused by other types of dementia, including Alzheimer's disease and dementia with Lewy bodies. These changes may interact to cause faster decline or make impairments more severe. You can help protect your brain with some of the same strategies that protect your heart—don't smoke; take steps to keep your blood pressure, cholesterol and blood sugar within recommended limits; and maintain a healthy weight. Physical exercise: Regular physical exercise may help lower the risk of some types of dementia. Evidence suggests exercise may directly benefit brain cells by increasing blood and oxygen flow to the brain. Diet: What you eat may have its greatest impact on brain health through its effect on heart health. The best current evidence suggests that heart-healthy eating patterns, such as the Mediterranean diet, also may help protect the brain. A Mediterranean diet includes relatively little red meat and emphasizes whole grains, fruits and vegetables, fish and shellfish, and nuts, olive oil and other healthy fats.

As noted above, there is no single test for determining whether a patient or subject is suffering from Alzheimer's or dementia. Rather, a diagnosis typically requires a complete assessment of all possible causes included reviewing the subject's medical history including family history of Alzheimer's or dementia, physical exams, neurological exams, mental status tests, and even brain imaging. Physical exams help a medical professional determine the subject's diet, use of alcohol, medication, vital statistics, and otherwise determine overall health and risk factors, along with performing lab tests. Information from a physical exam and laboratory tests can help identify health issues that can cause symptoms of dementia. Conditions other than Alzheimer's that may cause confused thinking, trouble focusing or memory problems include anemia, infection, diabetes, kidney disease, liver disease, certain vitamin deficiencies, thyroid abnormalities, and problems with the heart, blood vessels and lungs. Genetic testing may be performed to identify certain known risk genes that may show increased risk of Alzheimer's or dementia such as APOE-e4, a gene with high indication of increased risk for Alzheimer's, or tests for deterministic genes for autosomal dominant Alzheimer's disease (ADAD).

Neurological exams involve a clinician closely evaluating a subject for problems that may signal brain disorder's other than Alzheimer's such as strokes, Parkinson's disease, tumors, or other conditions that may impair memory or thinking by testing the subject's reflexes, coordination, muscle tone and strength, eye movement, speech, and sensation, and possibly brain imaging as well. Mental status tests are used to evaluate memory, ability to solve simple problems and other thinking skills to give an overall sense of whether the subject is aware of any symptoms, knows the date, time and location, and can remember lists of words, follow instructions and do simple calculation. Two common mental status, or cognitive, tests include the mini-mental state exam and the mini-cog test. The mini-mental state exam (MMSE) involves the clinician asking the subject a series of questions designed to test a range of everyday mental skills and is scored on a 0-30 scale where lower scores indicate more sever dementia or Alzheimer's. The mini-cog test (MCT) involves asking the subject to perform two tasks: 1) remember and a few minutes later repeat the names of common objects; and 2) draw a face of a clock showing all 12 numbers in the right places and a time specified by the clinician administering the exam. The results of this exam provide a general overview cognitive status of the subject and are used to determine whether further evaluation is needed. A growing area of research is the development of devices to administer computer-based tests of thinking, learning and memory, called cognitive tests. The U.S. Food and Drug Administration (FDA) has cleared several computerized cognitive testing devices for marketing. These are the Cantab Mobile, Cognigram, Cognivue, Cognision and Automated Neuropsychological Assessment Metrics (ANAM) devices. Some physicians use computer-based tests such as these in addition to the MMSE and Mini-Cog. Computerized tests have several advantages, including giving tests exactly the same way each time. Using both clinical tests and computer-based tests can give physicians a clearer understanding of cognitive difficulties experienced by patients. In addition to assessing mental status, the doctor will evaluate a person's sense of well-being to detect depression or other mood disorders that can cause memory problems, loss of interest in life, and other symptoms that can overlap with dementia. Further, a standard medical workup for Alzheimer's disease often includes structural imaging with MRI or CT; these tests are primarily used to rule out other conditions that may cause symptoms similar to Alzheimer's but require different treatment. Structural imaging can reveal tumors, evidence of small or large strokes, damage from severe head trauma or a buildup of fluid in the brain.

However, there are a number of other symptomatic factors that are not generally or robustly monitored in dementia patients. Cognition and mental ability are by far the most addressed symptoms or issues in diagnosing and treating Alzheimer's disease and other dementia, and rightfully so. However, combining the cognitive assessments with other symptoms and measurements, such as related to speech and/or movement, may provide a more complete objective picture of a patient's status and create a better diagnostic and treatment tool to earlier detect the onset of Alzheimer's or other dementia and to more effectively treat the disease and its symptoms. For example, many patients with Alzheimer's disease have walking difficulties. When these difficulties occur, patients walk with slow and irregular steps and find it hard to negotiate turns, climb onto a stepping stool, avoid obstacles in their path, or lie down and rise from the doctor's couch. Within three years after diagnosis, approximately 50% of Alzheimer patients reported problems in walking, and of these about 33% were classified as non-ambulatory. Patients with Alzheimer's disease may walk more slowly than healthy elderly people. These walking problems are interpreted as manifestations of the extrapyramidal deficits which affect 12-28% of Alzheimer's patients or as side effects of drug treatment—for example, with neuroleptic agents. However, Alzheimer's patients without apparent extrapyramidal signs may also show overt problems in walking and trunk movements. A proportion of these individuals may be affected by "frontal gait disorder," a syndrome coterminous with gait apraxia. Gait apraxia is the loss of ability to properly use the lower limbs in the act of walking. Gait apraxia includes disturbances of trunk movements, standing, and walking that are not caused by orthopedic abnormalities (for example, bone and joint degeneration), muscle wasting, arteriosclerosis obliterans of the lower limbs, pyramidal deficits, ataxia (cerebellar, vestibular or proprioceptive), dystonias and dyskinesias (from diseases that involve the basal ganglia), psychiatric disease (for example, schizophrenic mannerisms), side effects of drugs, or "cautious gait" because of fear of falling (also known as "trepidante Abasie" or staso-baso-phobia). Several forms of apraxia have been reported in patients with Alzheimer's disease, though walking problems and trunk movement deficits have been under-investigated in this condition.

It is therefore an object of the present invention to: 1) effectively combine kinematic data from accelerometers and gyroscopes, and other sensor data related to physiological characteristic affected by Alzheimer's or other dementia, with location, diary, and speech information obtained through data acquisition devices including, for example, smart phones, tablet computers, laptop computers, and the like, into a powerful research tool; 2) provide objective measures in the clinical market to quantify and optimize therapeutic response to treatments; and 3) optimize pharmaceutical treatments to reduce or minimize cognitive impairments and to decrease the risk of symptoms and side effects of such impairments. It is further an object of the present invention to provide accurate, objective monitoring of behavioral patterns of physical activity with sensors that may provide an accurate, objective appraisal of the impact of Alzheimer's or dementia on the physical, social, and emotional functioning that complements standard patient-reported outcome measures. Given the challenges and opportunities outlined above, the present invention aims to create an objective assessment method, system or device that will utilize motion sensors, other sensors related to physiological characteristics affected by Alzheimer's or dementia, and processing and interface components (such as a smart phone application, or "app") to monitor physical activity, and self-reported information on Alzheimer's or dementia symptoms and quality of life (QOL). Still further, it is an object of the present invention that the method, system or device can be used to help manage Alzheimer's or dementia patients, enabling them to capture objective data related to therapeutic response. In addition to Alzheimer's or dementia, it is an object of the present invention that the method, system or device will have implications for monitoring other disorders (e.g., depression) that affect behavioral patterns and rely on subjective patient self-assessment. It is yet a further object of the present invention that the method, system or device could be adapted in other programs as a telemedicine platform for delivering behavioral therapy, which has been shown to be a potential mechanism for expanding health care access for Alzheimer's or dementia patients.

SUMMARY OF THE INVENTION

The present invention relates to systems and methods for monitoring symptoms of diseases, disorders, and injuries. More particularly, the present invention relates to such systems and methods for monitoring symptoms of diseases, disorders, and injuries and also for providing possible treatment methods including titrations, changes and recommendations for those diseases, disorders, and injuries and their symptoms and side effects of treatment. The present invention further relates to a system and method of providing possible treatment methods for diseases, disorders, and injuries, their symptoms, and side effects of treatment based on a correlation of the particular subject's movement data with a database of similar data. Most particularly, the present invention relates to a patient customized and adaptive treatment and recovery system and method of improving the treatment and recovery of a subject regarding their diseases, disorders, and injuries. The present invention provides for a system and method that can determine patient customized treatments, particularly pharmaceutical treatments, either self-administered or with drug delivery devices in semi-closed loop or closed-loop control, but also for electrical stimulation parameters for deep brain stimulation (DBS), functional electrical stimulation (FES), transcranial direct current stimulation (tDCS), or the like, where such stimulation parameters include amplitude, current, frequency, pulse width, activation timing and the like. Preferably, the present invention achieves these goals by utilizing physiological and electrophysiological information from sensors, and many embodiments preferably utilize a database, or system of databases, of patient and treatment histories to correlate current subject information and data with historical data. The systems and methods preferably provide for pharmaceutical parameters such as drug titrations, doses and times. The present invention further includes a system and methods of storing and cataloging the movement related information and patient specific treatments in a database system to be used for continuous improvement of the treatment protocols for use with subjects in the future.

The present invention provides for systems and methods that can accurately measure, monitor, and quantify symptoms of disorders, diseases, and injuries, as well as side effects of treatment. The systems and methods accurately quantify symptoms and side effects utilizing physiological and/or electrophysiological sensor data, where the sensors or devices comprising the sensors can be worn continuously to provide continuous information to be analyzed as needed by system and/or a clinician, physician, or technician. The systems and methods can operate in real-time, including all measurement/sensing and analysis functions, which allows for home monitoring of symptoms and side effects in subjects to capture the complex fluctuation patterns of the disease, disorder, or injury over the course of days, weeks or months in a manner that maximizes subject safety and efficacy of treatment, and that provides remote access to the clinician, physician, or technician. The present invention relates to methods for semi-automatically and automatically adjusting, or tuning, treatment parameters in movement disorder therapy devices and systems, and more specifically for optionally remotely and intelligently adjusting or tuning such devices and systems. Semi-automatic adjustment includes providing the clinician, physician or technician with objective, quantitative or semi-quantitative data or measurements related to a subject's movement disorder symptoms, determining desired parameters, and then remotely entering those parameters either semi-automatically or automatically into the subject's therapy device. Semi-automatic or automatic adjustment (including but not limited to remote adjustment by clinicians) includes for example providing data including, but not limited to, objective, quantitative or semi-quantitative data and/or measurements related to a subject's movement disorder symptoms to an algorithm, using the data or measurements for determining desired parameters using the algorithm, and then entering those parameters either semi-automatically (i.e., allowing clinician, physician or technician to review and/or approve/adjust) or to automatically into the subject's therapy device. Alternatively or in addition, semi-automatic or automatic adjustment may not require sensors to provide data and/or measurements related to a subject's movement disorder symptoms, but rather may use qualitative or quantitative information such as, for example, traditional telemedicine techniques or remote observation by a clinician, physician or technician via video connection. In such embodiments, the clinician, physician or technician would perform a more classic scoring of the subject's symptoms rather than using quantified data and/or measurements from sensors attached to the subject's body or device such as for example by using video links between the clinician and the patient or subject. Remote adjustment or tuning includes the control and or decision regarding the therapy parameters to be programmed into the subject's therapy device being located remotely from the subject. For example, remote adjustment or tuning may be controlled by a clinician, physician or technician or an automated or semi-automated system using data transmitted from the subject and/or his or her therapy device without the subject having to travel to the clinical site to for such data to be obtained or transferred. The present invention further relates to a system for screening patients to determine if they are viable candidates for certain therapy modalities. The present invention still further provides methods of quantifying movement disorders for the treatment of patients who exhibit symptoms of such movement disorders including, but not limited to, Parkinson's disease and Parkinsonism, Dystonia, Chorea, and Huntington's disease, Ataxia, Tremor and Essential Tremor, Tourette syndrome, and the like. The present invention yet further relates to methods of automatically and intelligently tuning a therapy device using objective quantified movement disorder symptom data acquired by a movement disorder diagnostic device with the therapy settings or parameters to be provided to the subject via his or her therapy device.

Objective measurement and quantification of a subject's movement disorder symptoms, which is a preferable embodiment of the present invention includes symptoms such as tremor, bradykinesia, dyskinesia, gait and/or balance disturbances, and the like requires, as a first step, a measurement of the movement. This measurement can be performed by measuring a single movement metric, different movement metrics, or a combination of a number of movement metrics; and the movement metric or metrics being measured may include linear or rotational displacement, velocity, or acceleration, or any other metric that could give a quantitative indication of motion; and the part of the body being measured for motion may be a limb (as at a wrist, ankle, or finger) or may be the trunk of the body (as at a shoulder or torso), and the head. Sensors used for measuring body movement or motion include gyroscopes and accelerometers, preferably miniaturized, electromagnets, video, a multitude of sensors or system disclosed herein, or other sensors known to those skilled in the art. Additionally, sensors for measuring physiological signals such as electromyogram (EMG), electrooculogram (EOG), electroencephalogram (EEG), electrocardiogram (EKG), or other physiological signals which can directly or indirectly measure movement metrics in the subject may be included if such sensors and signals may be used to sense, detect, measure, and/or quantify the subject's external body motion, or related aspects. Other systems that can be used to detect and measure body motion include motion capture systems, machine vision systems, sonic or laser Doppler velocity transducers, infrared systems, GPS, or any other system known to those skilled in the art. The movement disorder diagnostic device used in the present invention may incorporate one or more of any of the above sensors or systems. Currently used movement data acquisition and diagnostic systems, such as described in U.S. Pat. No. 8,187,209 issued on May 29, 2012, herein incorporated by reference, may similarly be used in certain embodiments of the present invention. In the present disclosure, "movement data" is construed as including, but not being limited to, any signal or set of signals, analog or digital, corresponding to movement of any part of the body or multiple parts of the body, independently or in conjunction with each other. This includes physiological signals from which movement data or symptoms can be derived. Preferably, this movement data is generated with a movement sensor such as for example a gyroscope and/or an accelerometer, and additionally or optionally a video sensor.

Movement may be continuously measured over long time spans, or may be measured only over a short time span, for example, as during the period of one or more tests taken from or based on the UPDRS motor exam. A measurement time period comprises two separate time periods: (i) a sensing time during which the movement disorder diagnostic device and its included sensors are used to sense and measure the subject's external physical motion; and (ii) a processing or calculation time wherein the measured motion data is used to calculate objective scores and/or other kinematic data that quantify the severity of the subject's movement disorder symptoms and side effects, and wherein the scores. The measurement time required to adequately and accurately sense, measure and quantify the subject's movement can depend on the particular movement test or task being performed, which typically corresponds to a particular symptom of a movement disorder. Generally, however, the system aims to minimize the amount of measurement time required to obtain sufficient movement data and provide quantitative scores and/or kinematic data to continue the evaluative process. Preferably, the measurement time required to provide objective scores, symptom quantification, and/or kinematic data is less than about 120 minutes. More preferably, the measurement time required to provide objective scores, symptom quantification, and/or kinematic data is less than about 90 minutes. Still more preferably, the measurement time required to provide objective scores, symptom quantification, and/or kinematic data is less than about 60 minutes. Yet more preferably, the measurement time required to provide objective scores, symptom quantification, and/or kinematic data is less than about 45 minutes. Even more preferably, the measurement time required to provide objective scores, symptom quantification, and/or kinematic data is less than about 30 minutes. Still yet more preferably, the measurement time required to provide objective scores, symptom quantification, and/or kinematic data is less than about 15 minutes. Still even more preferably, the measurement time required to provide objective scores, symptom quantification, and/or kinematic data is less than about 10 minutes. Yet still more preferably, the measurement time required to provide objective scores, symptom quantification, and/or kinematic data is less than about 5 minutes. Yet even more preferably, the measurement time required to provide objective scores, symptom quantification, and/or kinematic data is less than about 60 seconds. Even still more preferably, the measurement time required to provide objective scores, symptom quantification, and/or kinematic data is less than about 30 seconds. Even yet more preferably, the measurement time required to provide objective scores, symptom quantification, and/or kinematic data is less than about 15 seconds. Still even yet more preferably, the measurement time required to provide objective scores, symptom quantification, and/or kinematic data is less than about 1 second.

In some embodiments, a periodic system may be employed wherein the subject's external body motions are sensed, measured, and quantified repeatedly but at predefined or altering intervals. In such periodic embodiments, the periodic measurements preferably conform to the above described measurement time period standards. Embodiments utilizing periodic measurement may begin when the subject attaches or dons the movement disorder diagnostic device, and may involve a step of instructing the subject to attach or don the device to begin a measurement period. Protocols for periodic measurement may be envisioned wherein a subject follows a particular schedule for measurement and quantification of movement disorder data, and wherein the schedule may change throughout the course of treatment and/or therapy. In still other embodiments, a continuous monitoring system may be employed wherein the movement disorder diagnostic device continuously senses, measures and quantifies the subject's external body movements over extended periods of time, such as hours, days, weeks or months. Preferably, in the continuous measurement embodiments, the diagnostic device senses, measures and/or quantifies the subject's external body movements substantially continuously, with no breaks or stoppages in its operation. However, the limits of continuous operation may be defined by characteristics of the device, such as battery life, form factor and construction (e.g., if it needs to be removed to shower), and other such concerns.

The movement disorder diagnostic device contains at least one electronic component that further may contain internal or onboard memory for storage of the movement data such that the data may be transferred at a later time. More preferably, the movement disorder diagnostic device further may contain communications electronics, which transmit the movement data to an external device for storage and/or analysis. The communication electronics preferably is/are wireless, and most preferably is/are radio frequency wireless. The external device may be a centralized storage database, parallel databases, a cloud-based database, a computer, tablet, cell phone including for example smartphone, personal data assistant (PDA) or similar device, or a combination of database and computer or communication devices. Preferably, such transmission of data occurs substantially in real-time. By real-time, it is meant that preferably, data is transmitted within 30 minutes of being acquired, measured, or calculated. More preferably, data is transmitted within 20 minutes of being acquired, measured, or calculated. Still more preferably, data is transmitted within 10 minutes of being acquired, measured, or calculated. Yet more preferably, data is transmitted within 5 minutes of being acquired, measured, or calculated. Even more preferably, data is transmitted within 5 minutes of being acquired, measured, or calculated. Still yet more preferably, data is transmitted within 3 minutes of being acquired, measured, or calculated. Even yet more preferably, data is transmitted within 60 seconds of being acquired, measured, or calculated. Yet still more preferably, data is transmitted within 45 seconds of being acquired, measured, or calculated. Yet even more preferably, data is transmitted within 30 seconds of being acquired, measured, or calculated. Even still more preferably, data is transmitted within 15 seconds of being acquired, measured, or calculated. Even yet more preferably, data is transmitted within 5 seconds of being acquired, measured, or calculated. Still even yet more preferably, data is transmitted within 1 second of being acquired, measured, or calculated. Yet even still more preferably, data is transmitted substantially simultaneously within milliseconds of being acquired, measured, or calculated.

Following measurement of symptomatic movement, the next step in objective quantification of a subject's movement disorder symptoms is the extraction of statistical kinematic features from the acquired movement data via processing. This processing may take place during or following data acquisition and may occur within a movement data acquisition device or within a different processing device, such as a personal computer, PDA, smart phone, tablet computer, touch screen interface, or the like, with which the acquisition device interfaces, either through a cable connection or by wireless transmission. Useful kinematic features that may be extracted from gyroscopic data may include, for example, peak power angular velocity, peak power angle, RMS angular velocity, frequency, maximum amplitude, maximum peak-to-peak amplitude, mean angular velocity, and wavelet parameters, as well as the covariance or standard deviation over time of any of these metrics. Useful kinematic features that may be extracted from accelerometer data may include, for example, peak power acceleration, peak power velocity, peak power position, RMS acceleration, RMS velocity, RMS position, frequency, maximum amplitude, maximum peak-to-peak amplitude, mean acceleration, and wavelet parameters, as well as the covariance or standard deviation over time of any of these metrics. In a movement data acquisition system, or movement disorder diagnostic measuring apparatus, that combines a three-axis accelerometer and a three-axis gyroscope to produce 6 channels of movement data, one or any combination of the above kinematic features can be extracted from any of the 6 kinematic channels to be used as inputs to a trained scoring algorithm in the next step. The listed kinematic features for the sensors above are intended to be exemplary, and not limiting; other types of sensors will produce different data from which different sets of features may be extracted.

The trained scoring algorithm used to process the kinematic features extracted from the movement data may comprise, for example, one or more of a simple or multiple linear regression, an artificial neural network, a Bayesian network, or a genetic algorithm. The output of the trained scoring algorithm may be a single score or multiple scores of any scale; a single score on the same scale as that of the UPDRS may be preferred in certain applications where simplicity or familiarity is the paramount concern, while more sophisticated scores and scales may be preferred for other advanced applications, such as those that involve recommendations for treatment or closed-loop automated treatment delivery.

In various embodiments, following the step of symptom quantification, a separate tuning algorithm may compute suggested changes to the therapy system parameter settings based on the result of the symptom quantification algorithm and known or predicted current therapy system parameter settings and physiological models.

Depending on the embodiment of the invention, the current therapy system parameter settings changes may be input into the algorithm by a software user interface (integrated tuning), or may be automatically sensed and input from the therapy or treatment parameter settings by communicating with a treatment device or implant (e.g., drug pump or electrical stimulation device such as DBS) or its programmer device or unit (intelligent tuning), or may be known because the therapy or treatment parameter settings have been preset to some known baseline settings or restored to a previously saved settings preset. The existing parameter settings might also be predicted or derived based, for example, on observed or measured therapy effectiveness. Suggested therapy system parameter settings changes are then input into the therapy system, and their effectiveness is measured using the above-described method of symptom quantification.

The process of tuning therapy system parameter settings may remain iterative, but the present invention significantly minimizes, or at least greatly reduces the time and expertise required to arrive at optimized stimulation or therapy parameter settings, advantageously allowing clinicians, technicians or physicians with lesser training or experience to adjust parameter settings during patient visits, and to do so in less time than is currently required. Additionally, the present invention increases access to geographically disparate populations by putting the expertise into the system and reducing or eliminating the need for an expert or trained clinician to be present with each subject.

Many embodiments of the present invention utilize a remote tuning or adjustment system. In such embodiments, at least one electronic component for transmitting and receiving signals is required. In such embodiments, data corresponding to the subject's measured and quantified movement and symptom data may be collected by the movement disorder diagnostic device and transmitted using the at least one electronic component for transmitting signals to a remote location or remote locations. The data may be transmitted to a clinical center or location where a clinician, physician or technician can view the data. In such embodiments, the clinician, physician or technician can then make a decision and determination regarding a second level of therapy settings that should be applied to the subject's therapy device. Alternatively or in addition, an algorithm may be used to provide the determination as to the second level of therapy parameters to be applied to the subject's therapy device, and a clinician, physician or technician may optionally review the settings determined by the algorithm. In the remote tuning or adjustment embodiments, once a determination as to a second or next level of therapy parameters is made, this second or next level of parameters is then transmitted back to the subject's therapy device where it is received by at least on electronic component for receiving signals. In still other remote embodiments, a tuning algorithm, as described below, of the movement disorder diagnostic device may provide suggested or determined second or next levels of therapy parameters, and in such embodiments the movement data and/or such suggested or determined parameters may be transmitted to storage or other remote locations as described. Additionally, the movement data and/or second or next level of therapy parameters may additionally be transmitted to a central server, cloud based server, or other such database for storage and backup purposes.

Many embodiments of the present invention include optimization or tuning algorithm(s) which are used to determine or recommend optimum therapy settings or parameters. Such optimization algorithms may include, but are not limited to simplex algorithms, extensions of the simplex algorithm designed for quadratic and/or linear function programming, combinatorial algorithms, and other multi-variant optimization algorithms known to those in the art. In order to determine what a desired or optimal level of therapy parameters might be, the subject's symptoms or side effects must first be measured and quantified. The measurement and quantification preferably take place while the subject is performing at least one movement disorder test as instructed. Once the initial measurement and quantification has been obtained, the system and/or, in some embodiments a clinician, physician or technician, programs a second level of therapy parameters into the subject's therapy device, and the subject repeats the movement disorder test(s) while the symptoms or side effects are again measured and quantified. This process is repeated until the desired result(s), goals or constraints are achieved. These processes and steps are described in greater detail below. Preferably, whether obtaining optimized therapy parameters or settings, or when iteratively testing to determine a second level of therapy parameters, preferably, the subject is instructed to perform, and performs, at least 1 movement disorder test, where the test comprises at least one task related to the subject's external body motion. More preferably, the subject is instructed to perform, and performs, at least 2 movement disorder tests. Still more preferably, the subject is instructed to perform, and performs, at least 3 movement disorder tests. Yet more preferably, the subject is instructed to perform, and performs, at least 4 movement disorder tests. Even more preferably, the subject is instructed to perform, and performs, at least 5 movement disorder tests. Still yet more preferably, the subject is instructed to perform, and performs, at least 6 movement disorder tests. Even still more preferably, the subject is instructed to perform, and performs, at least 7 movement disorder tests.

Optimization of therapy or treatment parameters or settings, or recommended drug regimens or protocols, can be described in reference to various constraints or desired results. In some embodiments, optimization of the recommended treatment or therapy based at least in part on sensor data, subject data, results and/or quantifications refers to a reduction or minimization of symptom occurrence and/or severity. Preferably in such embodiments, an optimized or second level of therapy parameters or settings, or recommended drug regimens or protocols, corresponds to at least a 10% reduction in the occurrence and/or severity of the subject's disorders and/or symptoms while the subject is receiving therapy or is under the effects of recently received therapy. More preferably, an optimized or second level of therapy parameters or settings, or recommended drug regimens or protocols, corresponds to at least a 20% reduction in the occurrence and/or severity of the subject's disorders and/or symptoms while the subject is receiving therapy or is under the effects of recently received therapy. Yet more preferably, an optimized or second level of therapy parameters or settings, or recommended drug regimens or protocols, corresponds to at least a 30% reduction in the occurrence and/or severity of the subject's disorders and/or symptoms while the subject is receiving therapy or is under the effects of recently received therapy. Still more preferably, an optimized or second level of therapy parameters or settings, or recommended drug regimens or protocols, corresponds to at least a 40% reduction in the occurrence and/or severity of the subject's disorders and/or symptoms while the subject is receiving therapy or is under the effects of recently received therapy. Even more preferably, an optimized or second level of therapy parameters or settings, or recommended drug regimens or protocols, corresponds to at least a 50% reduction in the occurrence and/or severity of the subject's disorders and/or symptoms while the subject is receiving therapy or is under the effects of recently received therapy. Still yet more preferably, an optimized or second level of therapy parameters or settings, or recommended drug regimens or protocols, corresponds to at least a 60% reduction in the occurrence and/or severity of the subject's disorders and/or symptoms while the subject is receiving therapy or is under the effects of recently received therapy. Even yet more preferably, an optimized or second level of therapy parameters or settings, or recommended drug regimens or protocols, corresponds to at least a 70% reduction in the occurrence and/or severity of the subject's disorders and/or symptoms while the subject is receiving therapy or is under the effects of recently received therapy. Yet still more preferably, an optimized or second level of therapy parameters or settings, or recommended drug regimens or protocols, corresponds to at least a 75% reduction in the occurrence and/or severity of the subject's disorders and/or symptoms while the subject is receiving therapy or is under the effects of recently received therapy. Even still more preferably, an optimized or second level of therapy parameters or settings, or recommended drug regimens or protocols, corresponds to at least an 80% reduction in the occurrence and/or severity of the subject's disorders and/or symptoms while the subject is receiving therapy or is under the effects of recently received therapy. Yet even more preferably, an optimized or second level of therapy parameters or settings, or recommended drug regimens or protocols, corresponds to at least an 85% reduction in the occurrence and/or severity of the subject's disorders and/or symptoms while the subject is receiving therapy or is under the effects of recently received therapy. Still even more preferably, an optimized or second level of therapy parameters or settings, or recommended drug regimens or protocols, corresponds to at least a 90% reduction in the occurrence and/or severity of the subject's disorders and/or symptoms while the subject is receiving therapy or is under the effects of recently received therapy. Yet still even more preferably, an optimized or second level of therapy parameters or settings, or recommended drug regimens or protocols, corresponds to at least a 95% reduction in the occurrence and/or severity of the subject's disorders and/or symptoms while the subject is receiving therapy or is under the effects of recently received therapy. Most preferably, an optimized or second level of therapy parameters or settings, or recommended drug regimens or protocols, corresponds to substantially eliminating the occurrence and/or severity of the subject's disorders and/or symptoms while the subject is receiving therapy or is under the effects of recently received therapy.

In other embodiments, optimization of the recommended treatment or therapy based at least in part on sensor data, subject data, results and/or quantifications refers to a reduction or minimization of side effect occurrence and or severity. Side effects may be a result of pharmaceutical therapy (medication) the subject is receiving to treat his or her movement disorders, or from the stimulation therapy (e.g., DBS). Preferably in such embodiments, an optimized or second level of therapy parameters or settings, or recommended drug regimen or protocol, corresponds to at least a 10% reduction in the occurrence and/or severity of the subject's side effects while the subject is receiving therapy or is under the effects of recently received therapy. More preferably, an optimized or second level of therapy parameters or settings, or recommended drug regimen or protocol, corresponds to at least a 20% reduction in the occurrence and/or severity of the subject's side effects while the subject is receiving therapy or is under the effects of recently received therapy. Yet more preferably, an optimized or second level of therapy parameters or settings, or recommended drug regimen or protocol, corresponds to at least a 30% reduction in the occurrence and/or severity of the subject's side effects while the subject is receiving therapy or is under the effects of recently received therapy. Still more preferably, an optimized or second level of therapy parameters or settings, or recommended drug regimen or protocol, corresponds to at least a 40% reduction in the occurrence and/or severity of the subject's side effects while the subject is receiving therapy or is under the effects of recently received therapy. Even more preferably, an optimized or second level of therapy parameters or settings, or recommended drug regimen or protocol, corresponds to at least a 50% reduction in the occurrence and/or severity of the subject's side effects while the subject is receiving therapy or is under the effects of recently received therapy. Still yet more preferably, an optimized or second level of therapy parameters or settings, or recommended drug regimen or protocol, corresponds to at least a 60% reduction in the occurrence and/or severity of the subject's side effects while the subject is receiving therapy or is under the effects of recently received therapy. Even yet more preferably, an optimized or second level of therapy parameters or settings, or recommended drug regimen or protocol, corresponds to at least a 70% reduction in the occurrence and/or severity of the subject's side effects while the subject is receiving therapy or is under the effects of recently received therapy. Yet still more preferably, an optimized or second level of therapy parameters or settings, or recommended drug regimen or protocol, corresponds to at least a 75% reduction in the occurrence and/or severity of the subject's side effects while the subject is receiving therapy or is under the effects of recently received therapy. Even still more preferably, an optimized or second level of therapy parameters or settings, or recommended drug regimen or protocol, corresponds to at least an 80% reduction in the occurrence and/or severity of the subject's side effects while the subject is receiving therapy or is under the effects of recently received therapy. Yet even more preferably, an optimized or second level of therapy parameters or settings, or recommended drug regimen or protocol, corresponds to at least an 85% reduction in the occurrence and/or severity of the subject's side effects while the subject is receiving therapy or is under the effects of recently received therapy. Still even more preferably, an optimized or second level of therapy parameters or settings, or recommended drug regimen or protocol, corresponds to at least a 90% reduction in the occurrence and/or severity of the subject's side effects while the subject is receiving therapy or is under the effects of recently received therapy. Yet still even more preferably, an optimized or second level of therapy parameters or settings, or recommended drug regimen or protocol, corresponds to at least a 95% reduction in the occurrence and/or severity of the subject's side effects while the subject is receiving therapy or is under the effects of recently received therapy. Most preferably, an optimized or second level of therapy parameters or settings, or recommended drug regimen or protocol, corresponds to substantially eliminating the occurrence and/or severity of the subject's side effects while the subject is receiving therapy or is under the effects of recently received therapy.

Still further, optimization of the recommended treatment or therapy based at least in part on sensor data, subject data, results and/or quantifications may refer to managing the subject's disorders and/or symptoms may further be measured with respect to the quantified severity or level thereof. Presuming that a quantification of the subject's disorders and/or symptoms involves a scale in which a higher value corresponds to more severe levels, intensities, occurrences, frequencies, and/or the like, preferably, the optimized or second level of therapy parameters, or recommended drug regimen or protocol, is adapted to maintain the quantification value below the total or highest value of the scale. In the alternative, or in addition, it may be preferable to maintain the quantification values of the subject's disorders and/or symptoms below a desired threshold value of the given scale. Preferably, the optimized or second level of therapy parameters, or recommended drug regimen or protocol, is adapted to maintain the quantification value below 75% of the highest scale value or the desired threshold. More preferably, the optimized or second level of therapy parameters, or recommended drug regimen or protocol, is adapted to maintain the quantification value below 65% of the highest scale value or the desired threshold. Still more preferably, the optimized or second level of therapy parameters, or recommended drug regimen or protocol, is adapted to maintain the quantification value below 50% of the highest scale value or the desired threshold. Yet more preferably, the optimized or second level of therapy parameters, or recommended drug regimen or protocol, is adapted to maintain the quantification value below 35% of the highest scale value or the desired threshold. Even more preferably, the optimized or second level of therapy parameters, or recommended drug regimen or protocol, is adapted to maintain the quantification value below 25% of the highest scale value or the desired threshold. Still yet more preferably, the optimized or second level of therapy parameters, or recommended drug regimen or protocol, is adapted to maintain the quantification value below 15% of the highest scale value or the desired threshold. Yet even more preferably, the optimized or second level of therapy parameters, or recommended drug regimen or protocol, is adapted to maintain the quantification value below 10% of the highest scale value or the desired threshold. Even still more preferably, the optimized or second level of therapy parameters, or recommended drug regimen or protocol, is adapted to maintain the quantification value below 5% of the highest scale value or the desired threshold. Yet still more preferably, the optimized or second level of therapy parameters, or recommended drug regimen or protocol, is adapted to maintain the quantification value below 3% of the highest scale value or the desired threshold. Still even more preferably, the optimized or second level of therapy parameters, or recommended drug regimen or protocol, is adapted to maintain the quantification value below 1% of the highest scale value or the desired threshold. If the scale comprises values where a higher value is indicative of less severe levels, intensities, occurrences, frequencies, and/or the like, then opposite of the above statements would be true, where the preferable ranges begin with 25% and end with 99%, and the preferred value is above those percentages.

Preferably, where the desired result is to reduce or minimize the subject's disorders and/or symptoms, the optimized or second level of therapy parameters, or recommended drug regimen or protocol, results in a reduction or minimization of at least 1 disorder and/or symptom. More preferably, the optimized or second level of therapy parameters, or recommended drug regimen or protocol, results in a reduction or minimization of at least 2 disorder and/or symptoms. Still more preferably, the optimized or second level of therapy parameters, or recommended drug regimen or protocol, results in a reduction or minimization of at least 3 disorder and/or symptoms. Yet more preferably, the optimized or second level of therapy parameters, or recommended drug regimen or protocol, results in a reduction or minimization of at least 4 disorder and/or symptoms. Even more preferably, the optimized or second level of therapy parameters, or recommended drug regimen or protocol, results in a reduction or minimization of at least 5 disorders and/or symptoms.

Preferably, where the desired result is to reduce or minimize the subject's side effects from medication or therapy, the optimized or second level of therapy parameters, or recommended drug regimen or protocol, results in a reduction or minimization of at least 1 side effect. More preferably, the optimized or second level of therapy parameters, or recommended drug regimen or protocol, results in a reduction or minimization of at least 2 side effects. Still more preferably, the optimized or second level of therapy parameters, or recommended drug regimen or protocol, results in a reduction or minimization of at least 3 side effects. Yet more preferably, the optimized or second level of therapy parameters, or recommended drug regimen or protocol, results in a reduction or minimization of at least 4 side effects. Even more preferably, the optimized or second level of therapy parameters, or recommended drug regimen or protocol, results in a reduction or minimization of at least 5 side effects.

Other secondary constraints or desired results may also be considered when optimizing or determining a second level of therapy parameters or settings such as maximizing the battery life of the therapeutic (e.g., drug pump or DBS) device, maximizing the therapeutic window, and the like. Such constraints or desired results as these are secondary only in that the primary goal of the therapy is to increase the subject's quality of life by reducing or minimizing symptoms or side effects, or balancing both, while also trying to improve the duration and quality of therapy otherwise. For example, maximizing battery life of the therapy device helps to increase the time required between subject's visits to the clinician, physician or technician as well as ensuring that the device has sufficient power and capability to effectively provide the determined levels of therapy. Similarly with maximizing the therapeutic window, which also increases the time between visits, but also maximizes the length of time that the stimulation therapy has a positive effect on the subject and reducing the number of stimulations required to achieve the desired results. Typically, the subject and his or her clinician, physician or technician will agree upon the primary desired result, such as minimizing symptoms, but numerous other such constraints will also be considered, weighed and balanced in determining the optimized or second level of parameters or settings.

Several embodiments may include a general optimization strategy in which combinations of the above desired results or constraints are used to select the appropriate optimized settings. For example, such embodiments may optimize based on reducing or minimizing both symptoms and side effects. Any combination of type and/or number of desired results or constraints may be used to optimize the system. Preferably, at least two different desired results or constraints are considered when determining an optimized group of therapy settings or parameters. More preferably, at least three different desired results or constraints are considered when determining an optimized group of therapy settings or parameters. Still more preferably, at least four different desired results or constraints are considered when determining an optimized group of therapy settings or parameters. Yet more preferably, at least five different desired results or constraints are considered when determining an optimized group of therapy settings or parameters. Even more preferably, at least six different desired results or constraints are considered when determining an optimized group of therapy settings or parameters. Most preferably, more than seven different desired results or constraints are considered when determining an optimized group of therapy settings or parameters.

The present invention provides dynamic assessment of the subject's physiological and environmental status. Such assessment is quite useful for mental and cognitive diseases, disorders, injuries and other impairments. For example, with specific respect to mental, cognitive, and memory impairments, it may be particularly relevant to describe the invention in regards to analysis of Alzheimer's disease and dementia. There are three main phases of Alzheimer's: mild, moderate, and severe. Each stage has its own set of symptoms. Mild Alzheimer's is the first stage and typically lasts approximately 2 to 4 years. Symptoms of mild Alzheimer's include: having less energy and drive to do things; less interest in work and social activities and spending more time just sitting, watching TV, or sleeping; loss of recent memories, like forgetting conversations and events that just happened; language problems, like trouble putting their thoughts into words or understanding others; mild coordination problems, such as trouble writing or using familiar objects; having a hard time with everyday tasks, such as following a recipe or balancing a checkbook; mood swings that involve depression or a lack of interest; and trouble with driving, like getting lost on familiar routes. When a person has one or a few of these issues, it doesn't necessarily mean he or she has Alzheimer's. There are other medical conditions that can cause the same problems, such as: conditions that affect metabolism, such as a thyroid problem; drug abuse, such as taking medications that don't work well together; Parkinson's disease; stress; or depression. Thus, it becomes increasingly difficult to diagnose the onset or presence of Alzheimer's or dementia given the cross-indications of many of the symptoms and the ease with which the individual symptoms may be overlooked or ignored. Medical professionals are able to perform tests to check the symptoms in order to determine if it is actually Alzheimer's/dementia, or some other problem with similar symptoms. Moderate Alzheimer's is the second stage, and the one when memory loss gets worse and starts to cause problems in daily life. This stage can last from 2 to 10 years. Someone with moderate Alzheimer's may start to forget details about his life, like where he or she went to high school or when he or she got married. He or she may not recognize or remember family members and friends, might also forget where he or she leaves things and can't retrace steps to find them, or other similar forms of memory loss. Other symptoms at this stage can include: rambling speech; trouble coming up with the right words and using the wrong ones; having a hard time planning or solving problems; confusion about time or place—may get lost in places he or she has been before or may not know how or why he or she got to that place; not dressing appropriately for the weather; getting angry or upset easily, sometimes lashing out at family or caregivers; trouble sleeping; wandering; and/or having delusions, such as thinking a caregiver is trying to hurt him. Some people with moderate Alzheimer's also become more aware that they're losing control of their lives, which can make them even more frustrated or depressed. The third stage is severe or late Alzheimer's which typically lasts about 1 to 3 years. People in this phase might have some or all of these symptoms: major confusion about what's in the past and what's happening now; inability to express themselves, remember, or process information; problems with swallowing and control of their bladder and bowels; weight loss, seizures, skin infections, and other illnesses; extreme mood swings; seeing, hearing, or feeling things that aren't really there, called hallucinations; and/or inability to move easily on their own. As noted above, many patients with Alzheimer's disease have walking difficulties. When these difficulties occur, patients walk with slow and irregular steps and find it hard to negotiate turns, climb onto a stepping stool, avoid obstacles in their path, or lie down and rise from the doctor's couch. Within three years after diagnosis, approximately 50% of Alzheimer patients reported problems in walking, and of these about 33% were classified as non-ambulatory. Patients with Alzheimer's disease may walk more slowly than healthy elderly people. These walking problems are interpreted as manifestations of the extrapyramidal deficits which affect 12-28% of Alzheimer's patients or as side effects of drug treatment—for example, with neuroleptic agents. However, Alzheimer's patients without apparent extrapyramidal signs may also show overt problems in walking and trunk movements. A proportion of these individuals may be affected by "frontal gait disorder," a syndrome coterminous with gait apraxia. Gait apraxia is the loss of ability to properly use the lower limbs in the act of walking. Gait apraxia includes disturbances of trunk movements, standing, and walking that are not caused by orthopedic abnormalities (for example, bone and joint degeneration), muscle wasting, arteriosclerosis obliterans of the lower limbs, pyramidal deficits, ataxia (cerebellar, vestibular or proprioceptive), dystonias and dyskinesias (from diseases that involve the basal ganglia), psychiatric disease (for example, schizophrenic mannerisms), side effects of drugs, or "cautious gait" because of fear of falling (also known as "trepidante Abasie" or staso-baso-phobia).

A number of sensors and sensing modalities may be useful with the present invention in the measurement and analysis of symptoms of Alzheimer's disease or other forms of dementia, including physiological signal sensors used to measure bioelectrical signals from a subject, for example electroencephalogram (EEG) or electromyogram (EMG) sensors. However, many other sensors and sensing modalities are not typically known to be useful in applications for measuring or analysis of a subject's Alzheimer's or dementia, particularly given that current diagnosis and analysis is generally all cognitive testing with subjective analysis by the test administrator. For example, movement sensors such as accelerometers, gyroscopes, magnetometers, resistive bend sensors and the like, designed to measure a subject's external body motion, are not known in the art to be generally useful for measuring or analyzing a subject's Alzheimer's or dementia. Similarly, other sensors and sensing modalities such as audio and speech sensors, sleep sensors, video sensors, global positioning (GPS) sensors, skin conductance sensors, pulse oximeters, and even some physiological signal sensors are not generally known to be useful for measurement or analysis of Alzheimer's or dementia symptoms.

Combining sensor-based analysis and measurement with cognitive testing allows the present invention to provide a diagnostic tool that may provide earlier and more accurate diagnostic capabilities than cognitive tests alone. The present invention provides a much broader source of data points that can be combined to analyze more aspects of the patient's health status to more accurately determine warning signs or occurrence of Alzheimer's or dementia symptoms. Expanding the diagnostic model to include objective, sensor-based measurements increases diagnostic accuracy by providing an objective component to the subjective clinician evaluation typically involved in cognitive tests. The objective sensor data can be correlated and/or compared with cognitive results through databases that preferably grow with new patient data providing an expansive correlative database that can train the algorithms as time goes on to produce better results to supplement and inform cognitive testing results. This diagnostic tool can then be coupled with treatment plans in order to delay the onset or progression of symptoms and improve the subject's QOL for a longer period of time.

Treatment of dementia depends on its cause. In the case of most progressive dementias, including Alzheimer's disease, there is no cure and no treatment that slows or stops its progression. But there are drug treatments that may temporarily improve symptoms. The same medications used to treat Alzheimer's are among the drugs sometimes prescribed to help with symptoms of other types of dementias. The U.S. Food and Drug Administration (FDA) has approved two types of medications—cholinesterase inhibitors (e.g., Aricept, Exelon, Razadyne) and memantine (Namenda)—to treat the cognitive symptoms (memory loss, confusion, and problems with thinking and reasoning) of Alzheimer's disease. There is also a medication that combines one of the cholinesterase inhibitors (donepezil) with memantine called Namzaric. As Alzheimer's progresses, brain cells die and connections among cells are lost, causing cognitive symptoms to worsen. While current medications cannot stop the damage Alzheimer's causes to brain cells, they may help lessen or stabilize symptoms for a limited time by affecting certain chemicals involved in carrying messages among the brain's nerve cells. Doctors sometimes prescribe both types of medications together. All of the prescription medications currently approved to treat Alzheimer's symptoms in early to moderate stages are from a class of drugs called cholinesterase inhibitors. Cholinesterase inhibitors are prescribed to treat symptoms related to memory, thinking, language, judgment and other thought processes. Cholinesterase inhibitors: prevent the breakdown of acetylcholine, a chemical messenger important for learning and memory which communication among nerve cells by keeping acetylcholine levels high, delay or slow worsening of symptoms, effectiveness varies from person to person; and are generally well tolerated, if side effects occur, they commonly include nausea, vomiting, loss of appetite and increased frequency of bowel movements. Three cholinesterase inhibitors are commonly prescribed: Donepezil (Aricept) is approved to treat all stages of Alzheimer's; Rivastigmine (Exelon) is approved to treat mild to moderate Alzheimer's, and galantamine (Razadyne) is approved to treat mild to moderate Alzheimer's. Memantine (Namenda) and a combination of memantine and donepezil (Namzaric) are approved by the FDA for treatment of moderate to severe Alzheimer's. Memantine is prescribed to improve memory, attention, reason, language and the ability to perform simple tasks. It can be used alone or with other Alzheimer's disease treatments. There is some evidence that individuals with moderate to severe Alzheimer's who are taking a cholinesterase inhibitor might benefit by also taking memantine. A medication that combines memantine and a cholinesterase inhibitor is available. Memantine: regulates the activity of glutamate, a chemical involved in information processing, storage and retrieval; improves mental function and ability to perform daily activities for some people; and can cause side effects, including headache, constipation, confusion and dizziness. An overview of current Alzheimer's disease and dementia drugs and medications can be seen in Table 1 below.

TABLE 1

Alzheimer's and Dementia Treatments - Medication

| Generic | Brand name | Approved for | Side Effects |
|---------|------------|--------------|--------------|
| donepezil | Aricept | All stages | Nausea, vomiting, loss of appetite, increased frequency of bowel movements |
| galantamine | Razadyne | Mild to moderate | Nausea, vomiting, loss of appetite, increased frequency of bowel movements |
| memantine | Namenda | Moderate to severe | Headache, constipation, |

TABLE 1-continued

Alzheimer's and Dementia Treatments - Medication

| Generic | Brand name | Approved for | Side Effects |
|---|---|---|---|
| rivastigmine | Exelon | Mild to moderate | confusion and dizziness Nausea, vomiting, loss of appetite, increased frequency of bowel movements |
| memantine + donepezil | Namzaric | Moderate to severe | Nausea, vomiting, loss of appetite, increased frequency of bowel movements, headache, constipation, confusion and dizziness |

Another form of treating Alzheimer's or dementia, other than focusing solely on memory loss, is to treat the behavioral changes symptomatic of the disease. Many people find the changes in behavior caused by Alzheimer's to be the most challenging and distressing effect of the disease. The chief cause of behavioral symptoms is the progressive deterioration of brain cells. However, medication, environmental influences and some medical conditions also can cause symptoms or make them worse. In early stages, people may experience behavior and personality changes such as: irritability; anxiety; and depression. In later stages, other symptoms may occur including: anger; agitation; aggression; general emotional distress; physical or verbal outbursts; restlessness, pacing, shredding paper or tissues; hallucinations (seeing, hearing or feeling things that are not really there); delusions (firmly held belief in things that are not true); and sleep disturbances. Events or changes in a person's surroundings often play a role in triggering behavioral symptoms. Change can be stressful for anyone and can be especially difficult for a person with Alzheimer's disease. It can increase the fear and fatigue of trying to make sense out of an increasingly confusing world. Situations affecting behavior may include: moving to a new residence or nursing home; changes in a familiar environment or caregiver arrangements; misperceived threats; admission to a hospital; being asked to bathe or change clothes, or the like. Identifying what has triggered a behavior can often help in selecting the best approach to deal with it. Even though the chief cause of behavioral symptoms is the effect of Alzheimer's disease on the brain, an examination may reveal other treatable conditions that are contributing to the behavior. Contributing conditions may include: drug side effects, discomfort from infections or other conditions, uncorrected problems with hearing or vision. With drug side effects, many people with Alzheimer's take prescription medications for other health issues. Drug side effects or interactions among drugs can affect behavior. Regarding infections or other conditions, as the disease gets worse, those with Alzheimer's have increasing difficulty communicating with others about their experience. As a result, they may be unable to report symptoms of common illnesses. Pain from infections of the urinary tract, ear or sinuses may lead to restlessness or agitation. Discomfort from a full bladder, constipation, or feeling too hot or too cold also may be expressed through behavior. Uncorrected hearing or vision problems can contribute to confusion and frustration and foster a sense of isolation. Non-drug therapies are preferably used first to try and alleviate these symptoms. Non-drug approaches to managing behavior symptoms promote physical and emotional comfort. Many of these strategies aim to identify and address needs that the person with Alzheimer's may have difficulty expressing as the disease progresses. Non-drug approaches should always be tried first. Steps to developing successful non-drug treatments include: recognizing that the person is not just "acting mean or ornery," but is having further symptoms of the disease; identifying the cause and how the symptom may relate to the experience of the person with Alzheimer's; and changing the environment to resolve challenges and obstacles to comfort, security and ease of mind. However, many Alzheimer's or dementia patients do not respond, or do not respond well-enough, to non-drug treatments alone. Many drug or medication based treatments are known for dealing with such behavioral changes due to Alzheimer's or dementia. If non-drug approaches fail after being applied consistently, introducing medications may be appropriate for individuals with severe symptoms or who have the potential to harm themselves or others. While prescription medications can be effective in some situations, they must be used carefully and are most effective when combined with non-drug approaches. When considering use of medications, it is important to understand that no drugs are specifically approved by the U.S. Food and Drug Administration (FDA) to treat behavioral and psychiatric dementia symptoms. Some of the examples discussed below represent "off label" use, a medical practice in which a physician may prescribe a drug for a different purpose than the ones for which it is approved. Some medications commonly used to treat behavioral and psychiatric symptoms of Alzheimer's disease include the following: antidepressants for low mood and irritability (e.g., citalopram, fluoxetine, paroxetine, sertraline, trazadone); anxiolytics for anxiety, restlessness, verbally disruptive behavior and resistance (e.g., lorazepam, oxazepam); antipsychotic medications for hallucinations, delusions, aggression, agitation, hostility and uncooperativeness (e.g., aripiprazole, clozapine, haloperidol, olanzapine, quetiapine, risperidone, ziprasidone).

Further, with treating Alzheimer's or dementia, subjects often have problems with sleeping or may experience changes in their sleep schedule. Scientists do not completely understand why these sleep disturbances occur. As with changes in memory and behavior, sleep changes somehow result from the impact of Alzheimer's on the brain. When managing sleep changes, non-drug coping strategies are typically tried first. Many people with Alzheimer's experience changes in their sleep patterns. Scientists do not completely understand why this happens. As with changes in memory and behavior, sleep changes somehow result from the impact of Alzheimer's on the brain. Many older adults without dementia also notice changes in their sleep, but these disturbances occur more frequently and tend to be more severe in Alzheimer's. There is evidence that sleep changes are more common in later stages of the disease, but some studies have also found them in early stages. Sleep changes in Alzheimer's may include: difficulty sleeping or daytime napping or other shifts in the sleep-wake cycle. Many people with Alzheimer's wake up more often and stay awake longer during the night. Brain wave studies show decreases in both dreaming and non-dreaming sleep stages. Those who cannot sleep may wander, be unable to lie still, or yell or call out, disrupting the sleep of their caregivers. Individuals may feel very drowsy during the day and then be unable to sleep at night. They may become restless or agitated in the late afternoon or early evening, an experience often called "sundowning." Experts estimate that in late stages of Alzheimer's, individuals spend about 40 percent of their time in bed at night awake and a significant part of their daytime sleeping. In extreme cases, people may have a complete reversal of the usual daytime wakefulness-nighttime sleep pattern. A person experiencing sleep disturbances should have a thorough medical exam to identify any treatable illnesses that may be contributing to the problem. Examples of conditions that can make sleep problems worse include: depression; restless legs syndrome, a disorder in which unpleasant "crawling" or "tingling" sensations in the legs cause an overwhelming urge to move them; and sleep apnea, an abnormal breathing pattern in which people briefly stop breathing many times a night, resulting in poor sleep quality. For sleep changes due primarily to Alzheimer's disease, there are non-drug and drug approaches to treatment. Most experts and the National Institutes of Health (NIH) strongly encourage use of non-drug measures rather than medication. Studies have found that sleep medications generally do not improve overall sleep quality for older adults. Use of sleep medications is associated with a greater chance of falls and other risks that may outweigh the benefits of treatment. Non-drug treatments aim to improve sleep routine and the sleeping environment and reduce daytime napping. Non-drug coping strategies should always be tried before medications, since some sleep medications can cause serious side effects. To create an inviting sleeping environment and promote rest for a person with Alzheimer's: maintain regular times for meals and for going to bed and getting up; seek morning sunlight exposure; encourage regular daily exercise, but no later than four hours before bedtime; avoid alcohol, caffeine and nicotine; treat any pain; if the person is taking a cholinesterase inhibitor (tacrine, donepezil, rivastigmine or galantamine), avoid giving the medicine before bed; make sure the bedroom temperature is comfortable; provide nightlights and security objects; if the person awakens, discourage staying in bed while awake; use the bed only for sleep; discourage watching television during periods of wakefulness. In some cases, non-drug approaches fail to work or the sleep changes are accompanied by disruptive nighttime behaviors. For those individuals who do require medication, experts recommend that treatment "begin low and go slow." The risks of sleep-inducing medications for older people who are cognitively impaired are considerable. They include increased risk for falls and fractures, confusion and a decline in the ability to care for oneself. If sleep medications are used, an attempt should be made to discontinue them after a regular sleep pattern has been established. The type of medication prescribed by a doctor is often influenced by behaviors that may accompany the sleep changes. The decision to use an antipsychotic drug should be considered with extreme caution. Research has shown that these drugs are associated with an increased risk of stroke and death in older adults with dementia. The FDA has ordered manufacturers to label such drugs with a "black box" warning about their risks and a reminder that they are not approved to treat dementia symptoms. Examples of medications used to treat sleep changes include: tricyclic antidepressants, such as nortriptyline and trazodone; benzodiazepines, such as lorazepam, oxazepam and temazepam; "sleeping pills" such as zolpidem, zaleplon and chloral hydrate; "atypical" antipsychotics such as risperidone, olanzapine and quetiapine; or older "classical" antipsychotics such as haloperidol.

Dynamic assessment of the subject's physiological and environmental status is also particularly relevant for subjects with chronic pain. Analyses of the temporal dynamics of movement have shown that measures of the relationship between periods of rest and activity (e.g., fractal and burstiness exponents) contain clinically relevant information in both chronic pain and depression patients. This evaluation of changes in the duration of successive activity and rest periods makes intuitive sense because the duration of resting time after a physically demanding activity increases in conditions such as chronic pain and fatigue. The importance of dynamic assessment is further supported by recent studies which have demonstrated that activity fluctuations, rather than mean activity level over time, contributed significantly in explaining disability in patients with CLBP. A different dimension of motor control in speech is affected by pain, as CLBP has been demonstrated to influence speech motor rates (i.e., the rate at which syllables such as "puh" and "tuh" can be produced) independently of disability and depression. The present invention leverages the processing and interface components (e.g., smartphone microphone) to record vocal samples and quantify speech motor control. In additional to physical limitations, sleep disturbance is a common behavioral-level complaint of patients with chronic pain. Polysomnography is very useful and established for diagnosis of most sleep disorders. However, motion sensors can also be used as an effective tool for quantifying sleep. The present invention leverages the motion sensor technology to quantify and analyze a subject's sleep, particularly in relation to pain, but can also utilize traditional sleep sensors and monitoring modalities in certain embodiments. The primary focus is on use of motion sensors to obtain objective motion data which broadens the appeal of such a system because motion sensors such as accelerometers have been integrated into treatment or therapy systems such as those using neurostimulators (e.g., RestoreSensor, Medtronic) providing feedback of posture for controlling stimulation. The present invention allows for the utilization sensors in the implant of such treatment or therapy devices that allow for the capture of a comprehensive picture of motor activity, which is crucial for characterizing disability.

The present invention utilizes a device that can objectively measure various aspects or metrics from the subject and quantify a level or severity symptoms related to Alzheimer's disease or dementia, and/or to quantify a level of pain, using an algorithm and data derived from the measured sensor data. Some embodiments of the present invention integrate collection of multidimensional data and automatic report generation for tracking therapy response. Some embodiments of the present invention utilize multiple motion sensors, other sensors related to physiological characteristics affected by Alzheimer's or dementia, or pain, symptoms or the subject's response to those symptoms, GPS, and processing and interface components (e.g., smartphone application) to monitor physical activity, sleep quality, speech patterns, community mobility, self-reported patient information on symptom level or severity and quality of life. Various embodiments of the present invention may further utilize open-loop, semi-closed-loop or closed-loop treatment or therapy delivery systems to provide treatment or therapy to the subject in light of the quantified level or severity of Alzheimer's disease or dementia, or pain, symptoms determined by the system, reported by the subject, or diagnosed by a clinician, physician, or technician. In an open-loop system, or as part of a semi-closed-loop system, the subject or a third-party such as a clinician, physician, or technician may be able to apply or administer treatment or therapy such as a drug or medication, for example using a portable drug titration and/or delivery device, or by titrating a new dose and/or regimen or protocol for self-administered medications. The subject may be able to call for a bolus of medication on demand, but such allowances should be limited to a certain maximum dose or number of doses in order to protect the safety of the subject and to prevent over-reliance or addiction to medications. Preferably, all drug titrations are governed at least in part by the drug's intended uses, indications of use and limitations. Similarly, a clinician, physician, or technician may be able to provide a dosage of drug or medication when necessary. In a semi-closed-loop system, the system may alert the user or clinician when a quantified level or severity of Alzheimer's disease or dementia, or pain, symptoms exceeds a certain threshold, or a calculated time period has passed, in order to allow the user or clinician to administer the treatment or therapy, or may provide a recommended treatment or dosage that the clinician can either confirm or override. Again, all drug dose and regimen or protocol instructions preferably are within drug indication limitations. Allowing a clinician, physician, or technician to see, review and interact with the quantified levels or severities Alzheimer's disease or dementia, or pain, symptoms of a subject and the treatment or therapy for the subject's Alzheimer's disease or dementia, or pain, allows the clinician, physician, or technician to understand the particular subject's symptoms in a more robust way. Each subject feels and perceives symptoms differently, and the present invention allows the clinician, physician, or technician the ability to understand the subject's perception in relation to the objective determination or quantification of Alzheimer's disease or dementia, or pain, symptoms provided by the system. Such understanding allows the clinician, physician, or technician to better understand and appreciate each subject's symptoms and to more accurately and effectively treat each patient. Closed-loop systems allow for the system to automatically provide tailored treatment or therapy, again preferably within drug indication limitations for drug-based therapies, to the subject based on the quantified level or severity of symptoms, while still allowing for clinician, physician, or technician override.

All data may be managed and processed on a secure cloud server synchronized with the smartphone app, or locally on the processing component of the method, system or device. Encrypted data may be uploaded to the server for processing whenever a mobile broadband or Wi-Fi connection is available. Reports will present changes in several behavioral-level measures, including, but not limited to: 1) percentage of day spent moving, 2) percentage of day spent in various body postures (e.g., lying, standing), 3) dynamic fluctuations in activity level throughout the day, 4) stride velocity and variability, 5) number and duration of trips away from home, 6) quality of sleep, and 7) speech alternating motion rates (AMRs). Validating these measures for Alzheimer's or dementia, or pain, and integrating them into a single system may provide significant differentiators between the present invention and existing commercial activity monitoring systems, with the primary innovations with unique and unexpected improvements based on algorithms and semi-closed loop or closed-loop control of therapy. Further, additional and unexpected improvements are also based on identification of physiological characteristics affected by Alzheimer's or dementia, or pain, and the data acquisition sensitivity required to identify those characteristics.

The methods, systems or devices of the present invention utilizes motion sensors, other sensors related to physiological characteristics affected by Alzheimer's disease or dementia, or pain, and processing and interface components (e.g., smart phone application) to monitor physical activity, location, and self-reported patient information on symptoms and QOL. The method, system or device of the present invention provides objective ambulatory measures of physical activity, physiological response, and community participation in patients with Alzheimer's disease or dementia, or chronic pain. Motion sensors, other sensors related to physiological characteristics affected by Alzheimer's or dementia, or pain, and processing and interface components (e.g., smart phone application) save data from the motion sensor units and log patient activity via GPS. Subjects may use the interface component to enter diary information such as when they took their medications, what they were doing, or how they felt and to record vocal samples. The method, system or device then analyzes and processes the collected data to quantify response to Alzheimer's or dementia, or pain therapies.

A motion sensor system or sensor unit, such as those described in U.S. Pat. No. 8,187,209 issued on May 29, 2012, U.S. Pat. No. 8,679,038 issued on Mar. 25, 2014, U.S. patent application Ser. No. 12/250,792 filed on Oct. 14, 2008, and U.S. patent application Ser. No. 15/210,990 filed on Jul. 15, 2016, each of which is herein incorporated by reference, may be used to acquire the various movement data. Communications for the sensor can be performed by any radio communications link known to those skilled in the art, including the preferred low-energy Bluetooth 4.0 radio or by a wired or tethered system. Using the low-energy Bluetooth radio, the device's battery will preferably last all day without needing to be recharged, and synchronization across multiple sensors is feasible. Sensor unit firmware is preferably able to communicate with the internal Bluetooth in a smartphone via the present invention's software app. The sensor board layout and housing of the motion sensor system preferably are designed and constructed so that the motion sensors and other sensors of the system can be easily worn on the wrist, torso, thigh, ankle, or any other part of a subject's body for which measurement is desired or best captured. The method, system or device may include an enclosure and strap design that utilizes a combination of elastic and rubber in the strap to maintain proper sensor alignment.

Where the present invention utilizes a smartphone and associated application ("app") for the processing and interface components, such app will preferably be available for use with any type of capable phone and operating system (e.g., Apple or Android operating systems). The app preferably includes a simple user-interface and several key features (e.g., activity monitoring via GPS, data transfer). The software preferably will take advantage of the smartphone's internal Bluetooth to collect kinematic data from the motion sensors, other sensors related to physiological characteristics affected by Alzheimer's or dementia, GPS, and mobile broadband/Wi-Fi. All data is preferably encrypted. Preferably, all software and app versions adhere to recently published FDA guidance on mobile medical applications.

The software app preferably takes advantage of the smartphone's internal GPS to track where the patient travels throughout the day. Studies have shown that the more active a patient is, the better his/her QOL. However, Alzheimer's or dementia, or pain, patients will often become confused or disoriented or experience reluctance to movement and activity. Monitoring the GPS signals of the system, whether in a subject's smartphone or in a separate monitoring and/or diagnostic device, can allow for identification of wandering movements that indicate confusion or disorientation, or sedentary or low-activity lifestyles that may indicate difficulty in moving or performing activities of daily living. The app tabulates how often the patient is at home, traveling, and at various locations. In addition to location, the app stores kinematic data from the motion sensors and other sensors related to physiological characteristics affected by Alzheimer's or dementia, or pain, which will be analyzed to extract features related to physical activity. The activity monitoring feature may be designed to continuously run in the background unless disabled by the patient. The frequency of GPS tracking and communication with motion sensors and the other sensors related to physiological characteristics affected by Alzheimer's or dementia, or pain, (e.g., once every two minutes) are preferably optimized to ensure that the smartphone battery lasts for at least 18 hours.

The software app also preferably includes a diary which patients will use to log their medication and dosing information (e.g., what drugs they took, when, what conditions, etc.), sleep habits, travel/activities, and self-rated disability/activity limitations (e.g., symptom occurrence, subjective reports on subject status). A diary may be created that allows subjects to note the: 1) Type of day (e.g., work, school, day off), 2) Periods of sleep and waking, including periods of being awake at night, 3) Consumption of coffee or alcohol, and 4) other similar or related activity or status inputs. Subjects may also complete an Epworth Sleepiness Scale (ESS) or utilize other assessment methods or devices once per day to rate sleepiness. The travel log enables subjects to "check-in" at locations throughout the day, similar to functions included in social networking sites. If no entries are detected, the app may provide a cue or alarm (vibrotactile or auditory) once per hour during the day as a reminder. Self-rated Alzheimer's or dementia symptoms can be entered using a 10-point numerical rating scale, which includes asking subjects to record ratings several times per day using paper forms to monitor treatment efficacy. Similarly, self-rated pain can be entered using an 11-point numerical pain rating scale (NPRS), similar to the current gold standard for clinical trials and pain management, which includes asking subjects to record ratings several times per day using paper forms to monitor treatment efficacy. Other scales may also be used for either Alzheimer's or dementia, or pain, ratings. For example, additional pain rating scales may include the Quebec Back Pain Disability Scale to score disability, and 3) the Tampa Scale for Kinesiophobia to score pain-related fear of movement. Some embodiments of the present invention may include non-clinically-known numerical scales that are based on independently researched and developed algorithms. Disability and activity limitations may be logged via subject questionnaires to be completed in the smartphone app once per day. These subject-centered manual entries of symptom intensity, disability, and community mobility are used to assess the accuracy of the automatic tracking that the app performs in the background using GPS motion sensors, and other sensors related to physiological characteristics affected by Alzheimer's or dementia, or pain. As a secondary outcome measure, speech analysis is also integrated into the methods, systems or devices and associated software. An additional push button allows subjects to complete a word or pattern alternating motion rate (AMR) task, during which the syllable sequence "puh" "tuh" "kah" will be repeated as rapidly and as accurately as possible on a single breath, which is particularly useful for chronic pain subjects. Alzheimer's or dementia, or chronic pain, may influence speech motor rates in performance of this standardized task and built-in smartphone hardware is leveraged by the present invention for vocal quantification.

In some embodiments, subject data may be entered into a visual representation of results which, for the purposes of the present invention, is called a map. The map visually presents the quantified symptoms based at least on movement data, but optionally also based on other sensor-measured data as detected, measured or otherwise determined by the method, system or device, as a result of a given set of conditions, variables or constraints. The map, in many embodiments, may be a two-dimensional representation of a three-dimensional plot of data and results. The conditions, variables or constraints may include anything which may affect the subject's symptom response, including, but not limited to: movement being performed, posture, time of day, locations, position, and the like. The conditions, variables or constrains may be measured, detected or determined objectively by the method, system or device, or may be manually entered by the subject. A clinician, technician or physician may manually enter the subject's movement or physiological data into a map upon reviewing the recorded data and results, or the data may be semi-automatically or automatically entered into a map by the software of the system. The software for the system, including mapping capabilities, may be installed on and operated directly by the methods, systems or devices, or can be web based through a web portal. The map is a tool that allows the system or a clinician, technician or physician to diagnose a subject or to determine treatment modalities or therapies to be used, or to tune therapeutic settings or parameters for a therapy device, such as a DBS device or medication infusion and/or titration device.

Preferably, the map is a two-dimensional representation of a three-dimensional graph or display of data. Generally, the horizontal and vertical axes of the map represent individual conditions, variables or constraints, or a grouping of multiple conditions, variables or constraints. The map is then populated with quantified symptom response and/or other test results obtained while the conditions, variables or constraints were affecting the subject. For example, in some embodiments, the vertical axis represents the time of day, and the horizontal axis represents the subject's posture. The map is then populated with coded indicators relating to an objective measured and quantified Alzheimer's or dementia, or pain, symptom response or measured movement data, where the indicators may be coded by color, pattern, quantified score, or some other representation of the score or test result. Thus, if it is 2:00 AM, and the subject is in a prone position, and registers a high pain or symptom response or symptomatic movement, then the map would be populated with a high symptom response marker for the given time and posture. An alternative used in many embodiments utilizes groupings of conditions, variables or constraints along one of the axes, rather than a single condition, variable or constraint. For example, the vertical axis may represent a combination of time of day and posture (e.g., axis points correlate to the time and a correlated posture measurement for that time), but now the horizontal axis may represent a measured movement (e.g., trunk rotation, perhaps indicative of the subject flipping over in his or her sleep). In such embodiments, the parameter groupings can be pre-defined sets of multiple conditions, variables or constraints, or can be combinations of pre-defined and measured conditions, variables or constraints. Therefore, instead of merely representing a single parameter, the axes may now represent groups with different combinations of conditions, variables or constraints, thus allowing for a far greater level of analysis rather than being limited to two variables. The condition, variable or constraint groupings are preferably cross-referenced within the tuning software such that the software of the system or a clinician, technician or physician can easily and quickly discern the conditions, variables or constraints comprised in each grouping. Some embodiments further allow the user, clinician, technician, or physician to add notations or comments to the map for later reference.

Preferably such notations or comments are able to be toggled between visible and hidden. These maps, once populated with conditions, variables or constraints and quantified Alzheimer's or dementia, or pain, symptom or movement response results and/or other results, represent the subject's response to the various conditions, variables or constraints, or groups thereof, which contributed to the subject's symptom response.

The subject's quantified pain or symptom responses are recorded in the map indicating the effect which the given set of conditions, variables or constraints had on the subject. The results that are used to populate the disorder and/or symptom response or severity maps may include any sort of measured, observed, or calculated response, or combinations thereof including, but not limited to, sensor recordings (for quantifying Alzheimer's or dementia, or pain symptoms), patient responses and perceptions, clinician observations, and clinician scores. Preferably, subjective perception- or observation-based results are stored as annotations or notations that can be used to provide context to the conditions, variables or constraints or to the quantified, objective symptom response, though some embodiments may incorporate the subjective scores into the recorded symptom response. In some preferred embodiments, it is possible that the map-population process may be entirely automated such that the map is populated entirely by sensor recordings of the subject's response to the conditions, variables or constraints and no human observation or calculation is required. Thus, the maps are populated and present a potentially visible representation of much of the input and output data that the system utilizes and produces.

To minimize the data stored on subjects' phones or other processing or data acquisition device, all data may be encrypted and uploaded to a secure cloud server for storage and processing. The system may store data on an external server that provides the physical safeguards required for HIPAA compliance.

Periods of activity may be identified using the accelerometer from a motion sensor worn on the wrist, or other sensors and/or algorithms. The method, system or device, for example, extracts a measure (i.e., burstiness parameter) of the distribution of the durations of activity and rest, as this has been shown to contain clinically relevant information in Alzheimer's or dementia, or pain patients. Body postures (i.e., sitting, standing, lying) can be detected from the torso and thigh accelerometer signals using validated computational techniques. An appropriate filtering technique (e.g., discrete wavelet transform) is utilized to allow for detection of postural transitions. Analyzing the angular velocities recorded by the motion sensor on the shank, the method, system or device identifies important gait events such as initial/terminal contact and mid-swing. The method, system or device then estimates several temporal (gait cycle time, double support) and spatial (stride length and velocity) parameters using gait models. The method, system or device automatically extracts community mobility measures from the GPS track data. Signal processing algorithms are employed to identify the number of productions of each syllable produced in each vocal sample (i.e., alternating motion rate).

At home subjects may wear the small motion sensors, and other sensors related to physiological characteristics affected by Alzheimer's or dementia, or pain, as they go about their normal routines to monitor physical activity and posture. Sensors may be worn on the wrist, torso, thigh, and ankle, or other parts of the head or body, preferably using an ergonomic form factor. The software app or software may be used to track community mobility by logging location via GPS. The wrist sensor may also be worn during sleep to monitor sleep quality. Subjects may use the processing or acquisition device, for example a smartphone app, to manually log their activities, location, and sleep habits to provide a patient-centered reference for subsequent analyses. Subjects may also use the app to record speech samples. All data may be uploaded to a web server via mobile broadband.

Algorithms automatically calculate a number of measures related to motor control, physiological characteristics and sleep quality. The time spent lying, sitting, standing, and walking, may be expressed as a percentage of the total amount of time that the sensors are worn. Double limb support time, leg swing velocity, and stride variability may be estimated from the lower extremity sensors. Sleep measures include the number of times subjects awoken during the night, the amount of time asleep, and sleep efficiency (i.e., time asleep/(total time in bed−time needed to fall asleep). The kinematic data from the wrist sensor may be used to calculate the percentage of monitoring time the subject is active and the burstiness parameter, which characterizes the dynamic pattern of activity-to-rest transitions throughout the day. The GPS data may be analyzed to identify the number of stops, number of trips, duration of stops, and length of trips. The percentage of time spent at home (i.e., within 50 km of home), in the neighborhood (i.e., within 1 km of home), in town (i.e., within 5 km of home), and out of town (i.e., 20 km and beyond from home) may also be calculated. Additionally or alternatively, wandering or confused movement or travel patterns may be monitored in order to track the subject in the event of confusion or disorientation related to Alzheimer's disease or dementia, or pain. The number of productions of each syllable may be extracted as a measure of speech motor control from each vocal sample.

With specific regard to subject's with chronic pain, the goal of the statistical analysis may be to identify objective features that quantify physical activity, speech motor control, and disability. Separate one-way analysis of variance (ANOVA) calculations with Tukey post-hoc comparisons using the outcome measures above as dependent variable and the subject group (i.e., no pain, moderate pain, or severe pain) as the independent variable can show the correlation between the variables and subject pain response. Pain level is often a significant factor ($p<0.05$) across outcome features. Time spent lying is often directly correlated with pain level, while the amount of time spent standing and walking, as well as the percentage of time active, are often inversely correlated with pain group. Sleep efficiency and the amount of time asleep are often inversely correlated with pain level, while the number of times awoken is directly correlated with pain group. Mobility measures and time spent outside of home are often inversely related to the pain group. Community mobility measures extracted from GPS to the activity and trip diary information can also be compared and demonstrate about 90% agreement between the number of trips and locations tracked. Comparisons of the sleep efficiency measures to the diary entries often show that that patients reporting excessive daytime sleepiness will have significantly increased number of times awoken and lower sleep efficiencies. Comparisons of the speech AMR to pain level often show that they are inversely correlated. A pattern recognition algorithm (i.e., linear discriminant analysis) can be trained to classify subjects into the pain groups using the objective measures as inputs.

A number of embodiments of the present invention are envisioned in this disclosure. These embodiments are examples of the many embodiments encompassed by the present invention, but do not in any way limit the many other embodiments covered by this disclosure.

One embodiment of the present invention includes a precision or personal drug or medication dosing system comprising: at least one movement sensor adapted to acquire movement data or movement data derived from at least one physiological sensor, the movement data related to a first subject's external body motion; at least one processor adapted for processing the acquired movement data; a quantification algorithm adapted to quantify symptom severity and to calculate a quantification score of at least one symptom based at least in part on the acquired movement data; and a treatment algorithm adapted to predict when a drug or medication should be administered to prevent an increase in symptom severity based in part on early detection of changes symptom severity and historical data of at least the first subject and/or other subjects, and to provide a recommended drug or medication regimen or protocol comprising a drug, drug dosage, and/or instructions for administration of the drug and/or drug dosage, the recommended regimen or protocol based at least in part on the calculated quantification score, wherein the algorithms are trained at least in part on reference data of the first subject and/or other subjects, the reference data comprising: movement data collected using at least one movement sensor or a physiological sensor corresponding to the first subject's and/or other subjects' movement, and at least one type of data from the group consisting of: clinician scores or sensor-based symptom quantification scores corresponding to the first subject's and/or other subjects' movement, and treatment parameters for the first subject and/or other subjects corresponding to the first subject's or other subjects' movement.

Another embodiment of the present invention includes a precision or personal drug or medication dosing system comprising: at least one movement sensor adapted to acquire movement data or movement data derived from at least one physiological sensor, the movement data related to a first subject's external body motion; at least one processor adapted for processing the acquired movement data; a quantification algorithm adapted to quantify symptom severity and to calculate a quantification score of at least one symptom based at least in part on the acquired movement data; and a treatment algorithm adapted to predict when a drug or medication should be administered to prevent an increase in symptom severity based in part on early detection of changes symptom severity and historical data of at least the first subject and/or other subjects, and to provide a recommended drug or medication regimen or protocol comprising a drug, drug dosage, and/or instructions for administration of the drug and/or drug dosage, the recommended regimen or protocol based at least in part on the calculated quantification score, wherein the recommended drug or medication regimen or protocol is adapted to provide a desired drug profile in the subject's bloodstream, and the system is further adapted to recommend or provide a new or additional drug dose based on the quantified symptom severity in order to prevent the onset or recurrence of symptoms, and the algorithms are trained at least in part on reference data of the first subject and/or other subjects, the reference data comprising: movement data collected using at least one movement sensor or a physiological sensor corresponding to the first subject's and/or other subjects' movement, and at least one type of data from the group consisting of: clinician scores or sensor-based symptom quantification scores corresponding to the first subject's and/or other subjects' movement, and treatment parameters for the first subject and/or other subjects corresponding to the first subject's or other subjects' movement.

Still another embodiment of the present invention includes a precision or personal drug or medication dosing system comprising: at least one movement sensor adapted to acquire movement data or movement data derived from at least one physiological sensor, the movement data related to a first subject's external body motion; at least one processor adapted for processing the acquired movement data; a quantification algorithm adapted to quantify symptom severity and to calculate a quantification score of at least one symptom based at least in part on the acquired movement data; and a treatment algorithm adapted to predict when a drug or medication should be administered to prevent an increase in symptom severity based in part on early detection of changes symptom severity and historical data of at least the first subject and/or other subjects, to provide a recommended drug or medication regimen or protocol comprising a drug, drug dosage, and/or instructions for administration of the drug and/or drug dosage, the recommended regimen or protocol based at least in part on the calculated quantification score, and to further provide an action recommendation corresponding to a suggested activity, exercise, diet, and/or environmental condition to prevent the onset or recurrence of symptoms, wherein the recommended drug or medication regimen or protocol is adapted to provide a desired drug profile in the subject's bloodstream, and the system is further adapted to recommend or provide a new or additional drug dose based on the quantified symptom severity in order to prevent the onset or recurrence of symptoms, and the algorithms are trained at least in part on reference data of the first subject and/or other subjects, the reference data comprising: movement data collected using at least one movement sensor or a physiological sensor corresponding to the first subject's and/or other subjects' movement, and at least one type of data from the group consisting of: clinician scores or sensor-based symptom quantification scores corresponding to the first subject's and/or other subjects' movement, and treatment parameters for the first subject and/or other subjects corresponding to the first subject's or other subjects' movement.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

BRIEF DESCRIPTION OF THE DRAWINGS

FIG. 4. Alternative display embodiment of monitoring results whereby substantially real-time gyroscope measurement signals are displayed for all three axes of gyroscope measurement.

FIG. 5. Chart presenting metrics either measured or derived by the present invention.

DETAILED DESCRIPTION OF THE INVENTION AND DRAWINGS

Figure 1:
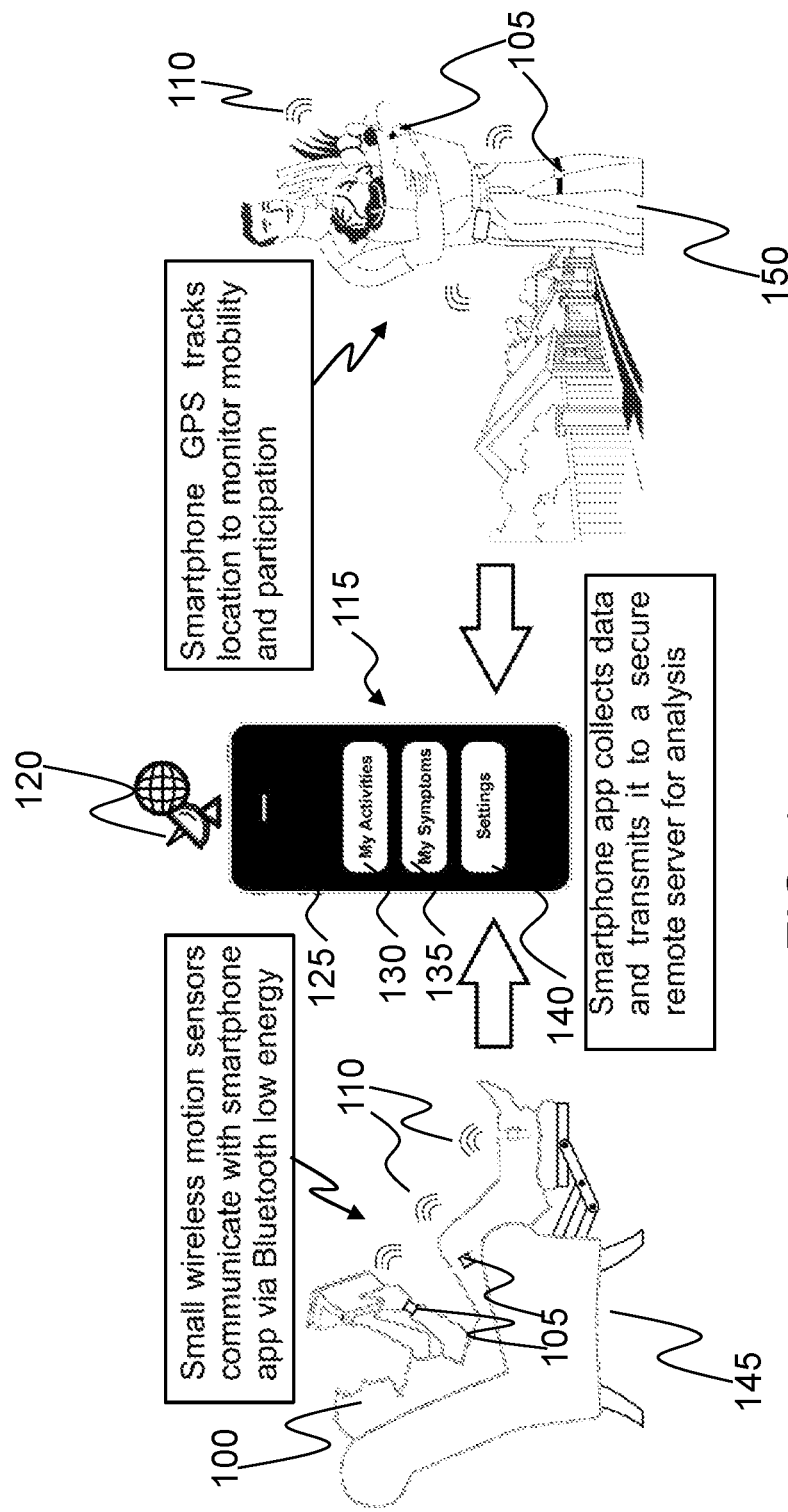
FIG. 1. Pictorial overview of one embodiment of the system of the present invention in use.

The present invention relates to systems and methods for providing recommended doses and instructions for pharmaceutical treatments. More particularly, the present invention relates to systems and methods for measuring physiological and/or electrophysiological signals from a subject and providing recommended doses and instructions of pharmaceuticals based at least in part on the measured signals. Further, the recommended doses and instructions are based at least in part on a subject's disease(s), disorder(s), or injuries and/or symptom(s) of such, and/or side effects of medications or treatments the subject is receiving. The recommended doses and instructions are personally tailored to the subject to precisely and personally address the subject's needs, and may be based in part on correlation with database(s) comprising historical data of the subject and/or other subjects to treat the subject's movement disorders, injuries to the body or brain, cognitive diseases and disorders, sleep diseases and disorders, chronic pain, or other conditions.

The devices of the various embodiments of the present invention can form part of a system for use by a physician, veterinarian, technician or clinician for treatment and further diagnosis of a subject's diseases, disorder, or injuries; for clinical research regarding the diseases, disorders, injuries, or treatments for such; or for delivery of treatment for such disorders, diseases, or injuries in clinical settings or for subjects outside the clinical setting such as at home or away from home while performing activities of daily living. Other elements of this system may include, but are not limited to, receivers, routers, communication devices, processors, displays, drug delivery devices, electrical stimulators, databases, algorithms, and the like, some of which are described further in various embodiments described in more detail below.

The devices worn by the various subjects or the different systems of the various embodiments of the present invention are preferably portable. By portable it is meant among other things that the device is capable of being transported relatively easily. Relative ease in transport means that the therapy device is easily worn and carried, generally, in a carrying case to the point of use or application and then worn by the subject without significantly affecting their range of motion or mobility. Further, portability in the sense of the present invention preferably means that all or a portion of the subject-worn monitoring device(s) is concealable and not openly visible while being worn by the subject. Furthermore, the portable measurement and quantification device, and optional pain treatment or therapy device preferably should be relatively light-weight. By relatively light-weight, preferably the device(s) weigh less than about 3 lbs., more preferably less than about 2 lbs., even more preferably less than about 1 lb., even more preferably less than about 0.5 lbs., still more preferably less than about 0.1 lbs., and most preferably less than about 20 grams. By being light-weight and further compact, the device(s) should gain greater acceptance for use by the subject. The entire system including the measurement and quantification device, treatment or therapy device, feedback modality, and other components including any processors, computers, video screens and the like preferably weigh less in total than about 15 lbs., more preferably less than about 10 lbs., even more preferably less than about 5 lbs., still more preferably less than about 2 lbs., and most preferably less than about 0.5 lbs. This system more preferably can fit in a reasonably sized carrying case so the subject or their caregiver can easily transport the system. Further, the portions of the device that are not worn by the subject while the device is in use should be easily and readily carryable and concealable, such as able to fit into a purse or pocket.

Another advantage of the systems and methods of the present invention is the ability to perform the measurement, analysis and quantification steps including measuring the particular metric(s) related to pain and quantifying the subject's diseases, disorders, injuries, pain, or symptoms (collectively referred to herein as disorders and/or symptoms) thereof, herein referred to as measurement analysis time in a very short amount of time, preferably in real-time. Preferably the system is able to measure the particular metric(s), analyze the data and provide a quantification of the subject's disorders and/or symptoms in less than 2 minutes (this can be referred to as real time measurement and quantification). More preferably, the system can measure the particular metric(s), analyze the data and provide a quantification of the subject's disorders and/or symptoms in less than 1 minute. Still more preferably, the system can measure the particular metric(s), analyze the data and provide a quantification of the subject's disorders and/or symptoms in less than 30 seconds. Yet more preferably, the system can measure the particular metric(s), analyze the data and provide a quantification of the subject's disorders and/or symptoms in less than 1 second. Even more preferably, the system can measure the particular metric(s), analyze the data and provide a quantification of the subject's disorders and/or symptoms in less than 500 milliseconds. Still yet more preferably, the system can measure the particular metric(s), analyze the data and provide a quantification of the subject's disorders and/or symptoms in less than 100 milliseconds. Even still more preferably, the system can measure the particular metric(s), analyze the data and provide a quantification of the subject's disorders and/or symptoms in less than 50 milliseconds. Yet even more preferably, the system can measure the particular metric(s), analyze the data and provide a quantification of the subject's disorders and/or symptoms in less than 1 millisecond. Most preferably, the system can measure the particular metric(s), analyze the data and provide a quantification of the subject's disorders and/or symptoms essentially simultaneously.

Still another advantage of the present invention is the ability to provide treatment or therapy for a subject's disorders and/or symptoms, herein referred to as disorders and/or symptoms treatment or therapy delivery time, that is similarly a very short period of time. disorders and/or symptoms treatment or therapy delivery time refers to the amount of time it takes for the device or system to determine, based on the quantified disorders and/or symptoms level, whether the subject needs disorders and/or symptoms treatment or therapy, or needs a current level of disorders and/or symptoms treatment or therapy to be adjusted, to transmit a signal to the pain treatment or therapy device, and for the disorders and/or symptoms treatment or therapy device to administer, deliver, instruct, or otherwise provide the appropriate treatment or therapy to the subject. Preferably, the disorders and/or symptoms treatment or therapy delivery time is less than 2 minutes. More preferably, the disorders and/or symptoms treatment or therapy delivery time is less than 1 minute. Yet more preferably, the disorders and/or symptoms treatment or therapy delivery time is less than 30 seconds. Still more preferably, the disorders and/or symptoms treatment or therapy delivery time is less than 15 second. Still yet more preferably, the disorders and/or symptoms treatment or therapy delivery time is less than 2 seconds. Even still more preferably, the disorders and/or symptoms treatment or therapy delivery time is less than 1 seconds. Yet even more preferably, the disorders and/or symptoms treatment or therapy delivery time is less than 0.50 seconds. Still yet more preferably, the disorders and/or symptoms treatment or therapy delivery time is less than 0.10 seconds. Most preferably, the system is able to make the appropriate determination, transmit the signal and deliver the appropriate treatment or therapy to the subject essentially simultaneously.

Effectively, the two distinct time periods defined above are intended to operate under the real-time constraints also defined above such that the system preferably operates and performs all required steps essentially instantaneously. In light of the rapid timing of the two stages defined above, the system therefore further provides the advantage of providing disorders and/or symptoms treatment or therapy very rapidly after a measurement is taken in order to minimize the amount of time the subject suffers from the disorders and/or symptoms, and this time period is herein referred to as measurement-to-treatment time, and is particularly related to semi-automated or automated (semi-closed loop or closed loop) treatments or therapies, but may also be useful or self-administered therapies and treatments such as oral or injected medications or drugs. Preferably, the measurement-to-treatment time is less than 4 minutes. More preferably, the measurement-to-treatment time is less than 2 minutes. Still more preferably, the measurement-to-treatment time is less than 1 minute. Yet more preferably, the measurement-to-treatment time is less than 2 minutes. Even more preferably, the measurement-to-treatment time is less than 30 seconds. Still yet more preferably, the measurement-to-treatment time is less than 5 seconds. Even yet more preferably, the measurement-to-treatment time is less than 3 seconds. Yet still more preferably, the measurement-to-treatment time is less than 1 second. Even still more preferably, the measurement-to-treatment time is less than 750 milliseconds. Yet even more preferably, the measurement-to-treatment time is less than 250 milliseconds. Still even more preferably, the measurement-to-treatment time is less than 50 milliseconds. Most preferably, the system measures the particular metric (s), analyzes the data to quantify the subject's disorders and/or symptoms, determines whether disorders and/or symptoms treatment or therapy is required or needs to be adjusted, transmits a signal to trigger the appropriate treatment or therapy, and provides the appropriate treatment or therapy substantially simultaneously.

The present invention is able to provide these significant improvements over systems known to those of skill in the art based on the enhanced and improved hardware and software of the present invention. The sensors utilized with the present invention are more sensitive and accurate than traditional sensors known to those in the art, allowing the system to acquire cleaner, higher quality signals and measurements directly from the subject with less noise or artifacts that need to be removed, and thus minimizing the amount of pre-processing and signal conditioning required, and time required to do so, in order to properly and effectively measure the various metrics and accurately quantify the subject's disorders and/or symptoms. Further, the processing components of the present invention are more powerful and the algorithms novel, more efficient, and better optimized, allowing the system to operate more quickly, more efficiently, and more accurately than those known in the art, further decreasing the time required to analyze the measured data, quantify the subject's disorders and/or symptoms, and administer or adjust treatment or therapy for such disorders and/or symptoms.

The preferable device or system worn, carried by or attached to the subject, contains various physiological or movement sensor(s) used to measure the subject's external body motion and/or other physiological signals from the subject's body, electrophysiological sensors, video sensors, audio sensors, and the like, and various subsets and combinations thereof. The subject-worn device or system may temporarily store the subject's movement or physiological data, or other data such as audio or video sensor data, in onboard memory and/or transmit this data to an external device. In some embodiments, the subject-worn device or system may directly transmit the data to a centralized database, to multiple databases at the same or multiple locations, or to a cloud-based database where the data can be stored and accessed essentially immediately by authorized users who can analyze and/or further process the data, use it to diagnose or assess the subject's symptoms or disorders, or the like. Additionally, or alternatively, the subject-worn device or system can transmit the recorded data to an external computer device, or directly to a remote location for access by a clinician, physician or technician. Transmission to a remote location preferably may include transmission directly to such a computer device at said remote location, or may involve a user (such as a clinician, physician or technician) at the remote location accessing the data or information through the database or databases as described.

The computer or processor device is understood to be any type of device known to those skilled in the art usable for the intended purpose(s) or function(s), including, but not limited to, desktop computers, laptop computers, tablet computers, personal digital assistants (PDAs, "smart" cellular telephones, and the like). The computer or processor device may be provided as part of the present invention's system, but in many embodiments the movement disorder diagnostic device is designed to work with and communicate with such devices of any third-party manufacturer or provider who provides such devices for the intended function or purpose of the present invention. In such cases, a software installation providing the user interface, symptom severity map capabilities, diagnostic and analysis tools, and the like would simply be installed on the third-party computer or processor device as software or an application (or "app"), or the interaction with the user(s) can be web based through a web portal. The symptom severity map is one example of a tool that allows the clinician, physician or technician to review and/or determine the next, or preferably best (optimized) therapeutic settings or parameters for the subject's therapy device. In the present invention, symptom severity maps are used primarily as a tool for review and analysis of results of monitoring as well as any suggested treatment or therapy parameters or settings provided by an algorithm, and/or for full-time or regular interaction and programming by a clinician, physician or technician.

Various embodiments of the present invention that include a central database system may consist of one or many databases specialized to certain forms of patient and/or movement data, such as patient demographics, treatment history, disorder details, recorded movement data, current treatment protocols, symptom severity scores, and the like. Symptom severity scores are may be a rescaling of a measured quantity. Alternatively, symptom severity scores may be representative of a score that a skilled clinician might give to the subject during a diagnostic exam in the clinician's office using a standardized scale. One example is for movement disorders, the symptom severity scores may preferably be correlated to or representative of scores given by a clinician, physician, or technician during a movement analysis exam under the Unified Parkinson's Disease Rating Scale (UPDRS). The central database or databases may be located locally or remotely with respect to a single patient or clinician. Further, the database may be part of another computer system, but is preferably run by a dedicated processor or group of processors. Preferably, all databases will also be located remotely so as to maximize the access by clinicians and patients from medical disorder fields and locations, thereby increasing an algorithm's ability to correlate data and determine a most customized treatment. More preferably, all databases will be adaptive to new patient information, and will grow in size as their use increases, thereby increasing the effectiveness of correlation algorithms as they have more information to compare and contrast with. The database system may be of any framework readily known to those skilled in the art, such as SQL, XML, or the like, so as to allow for relational queries between the databases and correlations with outside data.

Any database or database system of the present invention should comply with the Health Insurance Portability and Accountability Act (HIPAA) of 1996, particularly Title II of the act, which covers the privacy of protected patient and subject health care information. Protected information may be any part of the subject's medical record or payment history which may be linked to the individual. Such information related to this invention may include patient demographics, health history, recorded sensor data, past and current treatment protocols, clinician notes, patient disorder diaries. All data may only be obtained and stored with HIPAA compliant subject authorization. In compliance with the Privacy Rule of Title II, all subjects with data in the database(s) would be able to recover their stored information, or correct any incorrect information. Furthermore, all database workers and administrators should be trained in procedures relating to protected health information, and a privacy official and contact person will be appointed to handle all protected health information concerns.

In compliance with the Security Rule of Title II for electronic protected health information, administrative, physical, and technical safeguards should be implemented to protect sensitive health information. Administrative safeguards should comprise a written set of privacy procedures referencing a privacy officer and management oversight, describing who has access to protected information, how information is restricted to the fewest number of individuals, contingency plans, and internal audits. Preferably, multiple compliance officers should be hired; and during research applications of the invention, only researchers and clinicians should have access to the data, and in many instances, such access should be blind during research; and internal audits should occur at a regular frequency, where regular frequency preferably means once every year, more preferably once every month, even more preferably once every week, and most preferably once every day. Physical safeguards should govern hardware of the database system, access to the equipment and software of the system, and policies regarding workstation use. Preferably, the database hardware, such as the data storage drives, should be maintained in a private, continuously secured building and more preferably in a locked sever room within a private, continuously secured building where only database administrators have access to the hardware. Technical safeguards should comprise encryption techniques for the transfer of data, authentication techniques, records of all network settings, and documented risk analysis and risk management programs. Preferably, encrypted passwords are required used for any access of the database(s), cookies and IP address tracking are used to monitor remote access, a firewall installed on the database system is used to limit inbound and outbound traffic.

The above implementations regarding HIPAA compliance are not meant to be limiting or all inclusive. Instead they are meant to outline some of the primary procedures which will be installed in order to fully comply with the act. All required procedures described in the United States Code and Code of Federal Regulations should be implemented. It is also noted that Subtitle D of the Health Information Technology for Economic and Clinical Health (HITECH) Act, enacted in 2009, extends the privacy and security provisions of HIPAA to business associates of entities using the present invention. Preferably, additional safeguards should also be taken, and every implemented procedure should be continually monitored for technological advances and/or security breaches.

The various components of the system must be able to communicate with each other in order to transmit signals, data, commands, and the like between and amongst each other. Wireless communication is preferred for all communication of data to and from the device. Therefore, a radio or electronic component for communication is included in many embodiments of the present invention. The radio of the device controls and carries out communications between the device components, and between the portable diagnostic/measurement and therapy systems or devices and external devices. The radio may be a Bluetooth® communications device to provide wireless communications with external components such as displays, computers or processors, data acquisition circuitry, internet or cloud-based memory banks or databases, and the like, as well as internal components such as the internal portable diagnostic/measurement and therapy systems or devices memory, microprocessor, and the like. Both internal (between electrical components of the portable device(s)) and external (between the portable device(s) and external components or devices) communications may also be transmitted through wireless, wired, or a combination of both systems and methods. Preferably, a processor or micro-controller comprises algorithms and protocols for coordinating the operation of at least these internal electrical components, and in some embodiments also for preprocessing or processing sensor data.

Many different types and varieties of sensors can be used with the present invention to either directly acquire or measure metrics from the subject, or from whose measurements or signals other metrics may be derived. Different sensors can be used to acquire the subject's physical activity, the subject's mobility and participation in community or various activities, sleep quality, speech, or any other physiological condition of the subject. Preferably, the sensors included in the present invention are those that either directly measure physiological characteristics of the subject that are affected by the subject's disorders and/or symptoms, as well as those from which such measurements may be derived. These physiological characteristics will have either an abnormal pattern or will periodically provide an abnormal pattern which is indicative of disorders and/or symptoms intensity levels—can be suppressed, enhanced spikes, or the like. Various embodiments of the present invention may include a sensor for measuring a subject's external body motion, speech patterns, various physiological signals, and the like. The invention may also include at least one sensor for indirectly measuring movement metrics. Many types of sensors are known by those skilled in the art for measuring external body motion or providing physiological signals through which body movement information may be derived. External body motion sensors include but are not limited to accelerometers, gyroscopes, magnetometers, resistive bend sensors, combinations thereof, and the like. Preferably in some embodiments, a combination using at least an accelerometer and gyroscope is used. Sensors for acquiring physiological signals through which body movement information may be derived include, but are not limited to, electromyogram (EMG), electrooculogram (EOG), electroencephalogram (EEG), electrocardiogram (EKG or ECG), or other physiological signals which can directly or indirectly measure movement metrics in the subject, and may be included if such sensors and signals may be used to sense, detect, measure, and/or quantify the subject's external body motion, or related aspects.

One type of sensor included in many embodiments of the present invention includes gyroscopes. Gyroscopes can be used to measure, detect or otherwise determine orientation of the subject or the method, system or device. Preferably, electronic or MEMS (micro electro-mechanical system)-based gyroscopes are used. The gyroscopes of the present invention are preferably 3-axis gyroscopes, thus requiring only a single gyroscope to measure the angular momentum, and thus orientation in all three dimensions or aces rather than using three separate gyroscopes where one measures each dimension or axis. Typical gyroscopes function on the principle of the Coriolis Effect and a capacitive-based sensing system. Rotation of the sensor causes a shift in response of an oscillating silicon structure resulting in a change in capacitance. A typical application specific integrated circuit (ASIC), manufactured using a standard complementary metal oxide semiconductor (CMOS) manufacturing process, detects and transforms changes in capacitance into an analog output voltage, which is proportional to angular rate. The sensor element design utilizes differential capacitors and symmetry to significantly reduce errors from acceleration and off-axis rotations. However, in spite of the preferred characteristics, the system and devices of the present invention can operate effectively with any type of gyroscope known in the art. The preferred characteristics are such in order to aid in miniaturization and accuracy of the measurements of the system and devices, while also ensuring the most comfortable and enjoyable fit and experience for the user. Inclusion of gyroscopes in particular embodiments of the present invention, particularly in conjunction with accelerometers, allows the system and devices to detect and measure the subject's movement. Such measurements of movement aid in the tracking of health-related metrics and allow for a more robust and diverse set of data to be collected as well as derived.

Another type of sensor that can be used with the present invention includes accelerometers. Accelerometers may be used to measure or determine the subject's body position and orientation. Such accelerometers may be of any type known to those skilled in the art, including magnitude accelerometers and 3-axis accelerometers. Accelerometers can be included to detect angular movements and accelerations, and the like. The accelerometers used with the present invention may optionally be a dual axis acceleration measurement system on a single monolithic integrated circuit (IC). Such embodiments may contain a polysilicon surface-micromachined sensor and signal conditioning circuitry to implement open-loop acceleration measurement architecture. For each axis an output circuit converts the analog signal to a duty cycle modulated (DCM) digital signal that can be decoded with a counter/timer port on a microprocessor. The dual axis accelerometer is capable of measuring both positive and negative accelerations. The sensor may be a surface micromachined polysilicon structure built on top of the silicon wafer. Polysilicon springs suspend the structure over the surface of the wafer and provide a resistance against acceleration forces. Deflection of the structure is measured using a differential capacitor that consists of independent fixed plates and central plates attached to the moving mass. The fixed plates are driven by 180-degree out of phase square waves. Acceleration will deflect the beam and unbalance the differential capacitor, resulting in an output square wave whose amplitude is proportional to acceleration. Phase sensitive demodulation techniques are then used to rectify the signal and determine the direction of the acceleration. The output of the demodulator drives a duty cycle modulator (DCM) stage through a 32 kOhm resistor. At this point a pin is available on each channel to allow the user to set the signal bandwidth of the device by adding a capacitor. This filtering improves measurement resolution and helps prevent aliasing. After being low-pass filtered, the analog signal is converted to a duty cycle modulated signal by the DCM stage. A single resistor sets the period for a complete cycle (T2). A 0 g acceleration produces a nominally 50% duty cycle. The acceleration signal can be determined by measuring the length of the T1 and T2 pulses with a counter/timer or with a polling loop using a low cost microcontroller. More preferably, the accelerometers are 3-axis accelerometers capable of measuring acceleration in all 3 axes.

In preferred embodiments, a single sensor unit comprising at least an accelerometer and a gyroscope may be used. More preferably, a single chip containing both a 3-axis accelerometer and a 3-axis gyroscope (e.g., Invensense MPU-6000, or another chip with similar characteristics and capabilities, or more preferably more advanced characteristics and capabilities), may be used. The sensor unit preferably not only comprises at least an accelerometer and a gyroscope, but also allows for integration of other sensors external to the sensor unit. Preferably, the accelerometer and gyroscope are each three-axis sensors capable of measuring their respective movements (acceleration and orientation) in each of the three dimensions of movement (X, Y and Z). Each of the accelerometer and gyroscope may output a separate signal for their respective measurements in each axis, and these signals are all converted from analog to digital by a bank of analog-to-digital converters (ADC). The separate ADCs for each axis of the accelerometer and gyroscope allow for simultaneous sampling of each sensor and eliminate the need for an external multiplexer. Preferably the sensor unit as a whole, and the accelerometer and gyroscope in particular are capable of operation with low power consumption. Preferably, the accelerometer and gyroscope are user-programmable such that the user may define an operating range in which the sensors will work (e.g., the accelerometer may be programmed to operate from as low as ±2 g to as high as ±16 g, and the gyroscope from as low as ±250 degrees/second to as high as ±2000 degrees/second). Some embodiments may include other sensors integrated into the sensor unit as well, for example, a temperature sensor, which may be used to monitor the temperature of the sensor unit and ensure it is operating properly and under safe conditions.

The sensor unit further preferably comprises a digital motion processor (DMP), which may perform some preprocessing or processing of the sensor signals using algorithms for calculating metrics based on the particular disorders and/or symptoms and the sensors used. The digital motion processor at least preprocesses and/or processes the accelerometer and gyroscope signals to begin the analysis of the signals and to decrease the processing load on the external processor. Many embodiments may include external or additional sensors that are not housed within the sensor unit, but whose signals are transmitted to the sensor unit for integration with the accelerometer and gyroscope signals for further transmission to other internal or external components such as a processor. Such external or additional sensors may include, but are not limited to, force sensors, magnetometers, pressure sensors, bend sensors, combinations thereof, and the like, or other sensors as disclosed herein and not necessarily movement-related. These external or additional sensors communicate with the sensor unit by means of an auxiliary communications interface. The digital motion processor can integrate the signal(s) from these external or additional sensors along with the accelerometer and gyroscope signals and perform preprocessing or processing of all of the signals together, thus further streamlining the data acquisition process and reducing the workload of the external processor.

In many embodiments, the subject-worn device or system comprises a kinetic sensor board (or subject worn external sensor). The kinetic sensor board is preferably configured with at least an accelerometer and a gyroscope for quantifying the subject's motion. In some embodiments, the kinetic sensor board comprises at least three gyroscopes and three orthogonal accelerometers, but in more preferable embodiments the three of each sensor are replaced by at least one 3-axis accelerometer and at least one 3-axis gyroscope. The kinetic sensor board also includes a microprocessor and a power interface section.

Global positioning system (GPS) sensors may also be included on many embodiments of the present invention. GPS sensors are known in the art to be useful in tracking the subject's location, as well as distance traveled. Such measurements or determinations are useful for fitness and health applications whereby an athlete or person exercising can track his or her distance covered during exercise, and can be useful in other applications, for tracking similar values. For example, a subject wearing a device or system of the present invention can track his or her location in order to identify when the subject is at home and when the subject is away from home. By extension, the system can monitor the subject's distance traveled, as well as the time of travel, starts, stops, and the like, in order to monitor and track the subject's activity. The GPS sensors of the present invention may additionally, in some optional embodiments, be able to provide altitude measurements as well by utilizing a trilateration technique of synchronizing and measuring the distances between the method, system or device and at least four different satellites. In regards to the present invention, and particularly with respect to pain measurement and quantification, GPS data is useful in tracking the subject's movement in terms of distance, duration and starts and stops and correlating that data with the various other measures and metrics in order to assess how the subject's pain level is affecting his or her movement and involvement out in the community. For example, GPS data that indicates short distances of travel with numerous starts and stops could indicate a high level of pain as the subject has difficulty moving for longer distances or periods of time.

Another type of sensor that may be included in various embodiments of the present invention includes skin conductance sensors. Skin conductance is a measure of the electrical conductance of the skin, and is commonly known in the art as one of several names including galvanic skin response (GSR), electrodermal response (EDR), psychogalvanic reflex (PGR), skin conductance response (SCR) or skin conductance level (SCL). Galvanic skin response typically varies based on the moisture level of the subject's skin, such as is caused by sweating. Galvanic skin response can be used as an indicator of psychological or physiological stimulation or arousal—including pain. This is due to the fact that sweat is controlled by the sympathetic nervous system, which is the part of the autonomic nervous system that initiates or activates the fight or flight response in response to some stimulus applied to the sympathetic neurons. The sympathetic nervous system reacts to such stimuli by releasing acetylcholine (for preganglionic or presynaptic sympathetic neurons—those that reside in the spinal cord as part of the central nervous system (CNS)) or noradrenaline aka norepinephrine (for postganglionic or postsynaptic sympathetic neurons—those that reside outside the spinal cord, such as in the extremities, as part of the peripheral nervous system). Prolonged activation (exposure to the given stimuli) of the sympathetic nervous system can cause the release of adrenaline. The release of noradrenaline and adrenaline combine to give rise to the fight or flight response, which includes effects of increased sweating, pupil dilation, increased heart rate and increased blood pressure.

Therefore, sensors to measure galvanic skin response, as a function of the increased skin conductance caused by the increase in sweat, can be used to measure a subject's level of pain, excitement, stress, or other such indicates of psychological or physical arousal. Such galvanic skin response sensors measure the recorded electrical resistance between two electrodes when a very weak current is steadily passed between them. The sensors are normally placed a short distance apart, and the resistance recorded varies in accordance with the emotional state of the subject. Galvanic skin potential (GSP) refers to the voltage measured between two electrodes without any externally applied current, and is measured by connecting the electrodes to a voltage amplifier. Similarly, this voltage varies with the emotional state of the subject. Galvanic skin response can be highly sensitive to emotions in some people, though the GSR measurement cannot differentiate between what emotions are causing the response. GSR measurements are typically very small, such as on a microsiemen scale, but an accurately and correctly calibrated sensor and signal acquisition device or electronics can readily ascertain and measure such small values and changes in the GSR on such a scale.

Another example of the sensors that may be used in conjunction with the present invention includes a pulse oximeter. Pulse oximeters of any type known to those skilled in the art may be used. Generally, depending on the location of attachment to the subject's body, pulse oximeters tend to be either transmission or back scatter (a.k.a., reflection) sensors. Transmission sensors operate by generating a source of light at a known frequency and wavelength, passing said light through the subject's body, and measuring the amount of light that exits the subject's body on the other side. Transmission sensors, and particularly pulse oximeters, are typically applied to finger tips or the nose, generally due to the thin nature of those parts of the body as well as the ease in applying a sensor to both sides thus enabling the transmission measurement. Other areas of the body do not lend themselves as well to applying such sensors, and thus back scatter or reflection sensors may be used. Back scatter sensors operate by generating a source of light at a known frequency and wavelength, and then measuring the amount of light that bounces or reflects back to the measurement sensor which is on the same side as the light generator. These sensors tend to be less accurate than transmission sensors due to the loss of light as it scatters once it enters the subject's body—100% reflection is generally unachievable. In spite of the generally decreased accuracy, these sensors, particularly in pulse oximeters, are useful for application to the subject's ear to which would be uncomfortable and difficult to apply a transmission sensor. More specifically, with regard to the preferred sensor, the pulse oximeter can measure the oxygenation of the subject's blood by producing a source of light originating from the oximeter at two wavelengths (such as, in one embodiment, 650 nm and 805 nm). The light is partly absorbed by hemoglobin, by amounts which differ depending on whether it is saturated or desaturated with oxygen. By calculating the absorption at the two wavelengths the proportion of hemoglobin which is oxygenated can be estimated. Some embodiments, where the optional pulse oximeter is attached to or incorporated into a helmet, may be referred to as helmet-mounted pulse oximeter (HMPO) embodiments. In some embodiments, a pulse oximeter may be placed on a subject's fingertip. In other embodiments, a pulse oximeter may be placed directly on a subject's earlobe or forehead. In yet other embodiments, a pulse oximeter may be incorporated into a mask, helmet, or some other wearable, and then placed on the subject's forehead or earlobe when the mask, helmet or wearable is donned. In still yet other embodiments, a pulse oximeter may be attached in the subject's ear cup. In yet other embodiments, a pulse oximeter may be incorporated into a mask, helmet, or some other wearable, and is then placed in the subject's ear cup. In even other embodiments, a pulse oximeter may be applied to the bridge of the subject's nose, and is preferably incorporated into a mask, helmet, or other wearable. Pulse oximetry, with respect to the present invention, can provide an indication, through derivation of the pulse oximeter measurements, of abnormalities in the subject's ventilation caused by pain which lead to changes in the blood oxygen concentration.

Video sensors, such as cameras, video cameras, electro-optical infrared camera combinations, or the like, may be included as a sensor of various embodiments of the present invention as well. Video sensors of any variety can be used in conjunction with the present invention to provide or assist in recording pictures or video of the user and/or his or her surroundings while the method, system or device is in use, to provide movement or motion recognition (e.g., detect a subject's eye movement and adapt output or display of information based on such eye movement), or other such uses for photographic or video data recorded by such sensors. Video sensors may also be used to actually record the subject's movements in order to analyze how such movement is affected by any disorders and/or symptoms, or to even monitor the subject's facial expressions for indications of symptoms or changes in mood or demeanor. Preferably, embodiments in which a video sensor is used to acquire movement data of the subject's movements, such video movement data is correlated or synchronized with respect to time with movement data measured or acquired by any movement sensors attached to, worn, or carried by the subject. More preferably, the video data is time synchronized or correlated with respect to other all other sensors data, as well as treatments, clinician scores, treatment scores, and any other data acquired or generated by the system. Such time synchronization enables correlation and verification of the two types of movement data. Time synchronization further enables a clinician, physician, or technician to provide scores or ratings of the subject's movement and to coordinate those scores with scores or indexes generated by the system. Further, time synchronization allows for more accurate review at a later time. Facial recognition algorithms may be utilized with video or other visual data to detect a wide array of moods, attitudes or demeanors of the subject, including, but not limited to joy, sadness, anger, fear, surprise, contempt, disgust, and the like. Recognition of such moods or demeanors can be correlated with other objectively measured or subjective data to determine whether the subject is experiencing or otherwise struggling with disorders and/or symptoms, for example, symptoms of Alzheimer's or dementia or pain. Accordingly, many embodiments of the present invention will include a facial recognition algorithm for performing such analysis using video or other image data. All of this data can then be correlated with the other measures and metrics to help provide a quantification of symptom level or severity or to populate a symptom response or severity map.

Audio sensors may be included in various embodiments of the present invention as well. A typical audio sensor may be a microphone mounted or directed towards the subject, included in an ear-worn piece such as an earbud or headset, or can be a microphone included in the processor or processing device (i.e., smartphone or tablet), or in other similar or related locations. When placed in close proximity to the subject's mouth or nose, an audio sensor or microphone can be used to record or measure several various signals or metrics. In some embodiments, such a microphone may be used for the subject to actually record audio signals such as voice notes or messages, or to interact with an external device. The system may further monitor the subject's speech to detect speech patterns and volume. Various algorithms in the present invention may analyze a number of speech components in order to determine abnormalities that may indicate, particularly when correlated with cognitive test results, symptoms of disorders and/or symptoms, for example Alzheimer's or dementia or pain. Additionally, a facially-oriented microphone may be used to measure a subject's breathing (i.e., breath rate or air pressure of breaths), and relatedly, snoring or other such breathing conditions. Such measurements can be used to help identify sleep cycle patterns or stages as well as be fused with other metabolic and physiological data to form a complete picture of the subjects health (e.g., breath rate during exercise may be fused with ECG and heart rate data to provide a more complete metabolic profile or cardiovascular health indication).

More preferably, audio sensors can be used to record speech patterns of the subject in order to allow those speech patterns to be analyzed in a manner to assess the subject's symptoms. Measures or metrics pertaining to a subject's disorders and/or symptoms, particularly Alzheimer's or dementia or pain symptoms may be measured, calculated or estimated from processing and analysis of these speech patterns include pitch, loudness or sound pressure level, timbre, tone, sharpness or crispness of certain words or syllables of a subject's speech, the rate at which these words or syllables are formed, the time it takes to form a particular aspect of speech or syllable, time gaps between words, and the like. Depending on the particular subject and his or her symptoms, the speech patterns may vary in different ways. Some subjects may vary their speech linearly such that the subject's symptoms include, for example, a dulling or softening of the sharpness or crispness of a speech pattern or syllable as well as a lengthening of the time it takes to form the pattern or syllable and slowing of the rate of forming such pattern or syllable. Typically, the stronger the symptoms and/or more advanced the disorders and/or symptoms, the more the subject's ability to form particular speech patterns is impaired. The exact combination of measures or metrics regarding speech patterns may thus be very subject-specific and therefore require calibration of the system to the particular subject's speech patterns and symptom responses. In order to measure the subject's speech and use the various speech measures or metrics to help determine the subject's quantified disorders and/or symptoms level, the system must receive and record the subject's speech, and in some embodiments perform a real-time monitoring of the subject's speech. The subject may be instructed to or otherwise perform a set of regimented speech exercises that direct the subject to speak certain words, phrases or syllables into the audio sensor, thus provided the system with a specific set of expected speech patterns to analyze. Alternatively, or in conjunction with instructed speech, the system may be used to measure the subject's speech either on demand whereby the subject or system initiates recording of the subject's speech, or in real-time, normal conversation or speech where the system measures whatever speech the subject happens to be engaging in. In any of these embodiments, the system records the subject's speech and performs a signal processing function to isolate the speech patterns or syllables of interest, and then processes the various measures or metrics of those patterns or syllables to help quantify the level or severity of the subject's disorders and/or symptoms. Algorithms for analyzing speech data preferably are adapted to receive as input speech data or processed data related to the subject's speech that represents components of the subject's speech. The Algorithms analyze the speech or related data to determine whether one or more of the speech metrics including one or more of: speech patterns, volume, pitch, loudness (sound pressure level), tone, time gap between words, and the like. With specific regard to speech patterns, patterns that may be utilized to determine symptomatic speech include repetition of words, incorrect combinations of words, stuttering, and the like. The algorithms may pick out repetition of words or syllables (stuttering) which may be signs of mental confusion or inability to form words or coherent thought and speech. An algorithm may detect that the subject is using combinations of words that make little or no sense, further indicating faulty thought processes or a disconnect between thought and speech. Sound characteristics of speech, such as pitch, loudness, volume, timbre, tone, and the like may be determined by one or more speech analysis algorithms as indicators of the subject's mood or demeanor. Anger or annoyance may be indicated by one or more of these metrics, for example, and may be indicative of the occurrence of symptoms that give rise to these emotions. For example, if a subject cannot remember what he or she is trying to do or say, a common reaction might be to become angry or annoyed. Thus, analysis of the subject's speech allows the algorithms to analyze the subject's speech and make determinations or quantifications of the subject's symptoms. Emotion determinations can be correlated with other symptom measurements or tests (e.g., cognitive tests) in order to more accurately determine the occurrence of disorders and/or symptoms, particularly Alzheimer's or dementia or pain.

The system preferably is able to identify and measure the specific speech patterns in a given subject. Calibration of the system system's sensors may be required and can be performed in a number of ways. Preferably, the sensors are calibrated during a set of defined or known tasks designed to record each sensor's particular signal under the known variables to calibrate the sensors and algorithms to the subject's movement or speech. Multiple sensor measurements can preferably calibrated between and amongst each other in order to align particular disorders and/or symptoms related responses with similar responses measured by other sensors. One example of calibration involving the speech metrics or measures preferably is performed with a regimented set of speech patterns or exercise by the subject. As the subject performs the predetermined, regimented speech patterns, the system records the speech. This speech data can be correlated to various types of other data, both objective and subjective, in order to teach the system the correlation between the measured symptoms, perceived symptoms and the speech pattern response. The objective calibration data may include one or more physiological signal measurements such as magnetic resonance imaging (MRI), EEG, EMG, ECG, or the like, or a combination of such signals and other measures such as described herein. For example, during a calibration session, the subject may be attached to an EEG or MRI recording device, and the subject's EEG or MRI activity measured while he or she performs the regimented calibration speech patterns. EEG or MRI data can provide an objective measure of the subject's symptom level through the level of activity in the brain. Similarly, the patient may provide subjective data regarding his or her perceived symptom level, for example indicating the degree of difficulty in performing a tasking or remembering instructions, while performing the calibration speech. The same process can be performed for movement sensors. Once the calibration tasks are completed, the data can be analyzed to correlate the measured and/or subjective symptom response to the change in the subject's speech or movement patterns, and thus the system can learn how the particular subject's speech or movement correlates to levels of symptoms.

With specific respect to the various speech-related measures or metrics, the system is preferably able to determine changes in the measures or metrics with a high degree of accuracy and sensitivity in order to determine even slight changes in the subject's speech that may indicate the subject is experiencing disorders and/or symptoms. The symptoms and metrics for speech disclosed above can be separated into three basic groups: 1) speech pattern metrics (e.g., repetitive or rambling patterns or words or syllables, word combinations, and the like); 2) speech sound quality metrics (e.g., volume, pitch, loudness or sound pressure level, timbre, tone, and the like); and 3) speech timing metrics (e.g., time gap between words, length of time to form syllables or words, and the like). With respect to the various speech patterns or syllables, preferably the system is able to detect a 75% or less variance in a speech pattern metric, a speech sound quality metric, and/or a speech timing metric. More preferably, the system is able to detect a 65% or less variance in a speech pattern metric, a speech sound quality metric, and/or a speech timing metric. Still more preferably, the system is able to detect a 50% or less variance in a speech pattern metric, a speech sound quality metric, and/or a speech timing metric. Yet more preferably, the system is able to detect a 35% or less variance in a speech pattern metric, a speech sound quality metric, and/or a speech timing metric. Even more preferably, the system is able to detect a 25% or less variance in a speech pattern metric, a speech sound quality metric, and/or a speech timing metric. Still yet more preferably, the system is able to detect a 20% or less variance in a speech pattern metric, a speech sound quality metric, and/or a speech timing metric. Yet still more preferably, the system is able to detect a 15% or less variance in a speech pattern metric, a speech sound quality metric, and/or a speech timing metric. Even yet more preferably, the system is able to detect a 10% or less variance in a speech pattern metric, a speech sound quality metric, and/or a speech timing metric. Even still more preferably, the system is able to detect a 5% or less variance in a speech pattern metric, a speech sound quality metric, and/or a speech timing metric. Still even yet more preferably, the system is able to detect a 3% or less variance in a speech pattern metric, a speech sound quality metric, and/or a speech timing metric. Yet even still more preferably, the system is able to detect a 2% or less variance in a speech pattern metric, a speech sound quality metric, and/or a speech timing metric. Even still yet more preferably, the system is able to detect a 1% or less variance in a speech pattern metric, a speech sound quality metric, and/or a speech timing metric. Detection of such degrees of variation in the given measures or metrics of speech patterns allows the system to determine that the subject's speech is becoming impaired, which may correlate to an increased symptoms of Alzheimer's or dementia.

The system preferably uses at least one of the various types of sensors described above, but may use multiple sensors, and multiple types of sensors, in many combinations to provide a more complete and robust analysis of many facets and aspects of the subject's physiological and, in some embodiments, mental states to more accurately determine the level or severity of disorders and/or symptoms the subject is experiencing and provide a quantitative value for assessment of that disorder's and/or symptom's level or severity. Some of the described sensors may be more sensitive to actual measurement of subject symptoms while others may be more useful in providing other physiological or status data that can be used to calculate or estimate symptom-related information. Thus, using various types of sensors, measurements and data in conjunction with each other allows the system to be better trained and calibrated to the particular user's unique symptom responses, and to provide a more accurate detection or identification of actual response to symptoms to, in turn, provide a much more accurate quantitative symptom level or severity output.

The sensors of the present invention are preferably designed to be particularly accurate, reliable, and repeatable, and thus sensitive, in obtaining their respective measurements. Many statistical metrics can be used to evaluate the reliability and repeatability sensor measurements. Several of the most commonly used and accepted metrics include standard error of measurement (SEM), minimal clinically important change or difference (MCIC/MCID), smallest detectable difference (SDD), fluctuation, intraclass correlation (ICC), and minimal detectable change (MDC). These metrics each provide a quantitative analysis of how statistically accurate a measurement system is, and thus provide measures of the reliability, accuracy and sensitivity of these scales and systems. Methods for measuring and determining the reliability, accuracy and sensitivity of the sensor measurements, including descriptions of the metrics and their use, are described in greater detail in U.S. Pat. No. 8,845,557 issued on Sep. 30, 2014 and U.S. patent application Ser. No. 13/785,273 filed on Mar. 5, 2013, which are herein incorporated by reference. As such, preferably the present invention is capable of measurements using its sensors with the same degree of sensitivity, accuracy and reliability as is described in the incorporated applications.

As noted, many embodiments of the present invention will utilize wearable sensors and, in certain embodiments, processors or processing devices. Examples of such sensor devices, processor or processing devices, or devices that combine both sensors and processing capability include smart phones, personal digital assistants (PDAs), laptop computers, tablet computers, personal electronic accessory devices such as watches (e.g., Apple Watch, Fitbit Ionic, Samsung Gear watches, LG smart watches, Google smart watches, and the like), headphones, smart glasses or eyewear, personal fitness monitors (such as those offered by Fitbit, Jawbone, Garmin, Toobur, Amazfit, Omron, Withings, and the like), or the like, or standalone processing devices designed specifically for use or compatible with applications of the present invention, each embodiment including or being able to have coordinated application(s), program(s) or software installed in order to perform the analysis. The present invention preferably involves leveraging and adapting these technologies in an integrated platform with unique features to improve gait, balance, posture and movement in general or resulting from a movement disorder or disease, but also after injury (such as TBI or stroke)—a process and concept not currently known or utilized in the art. The system components provide a low-cost, portable platform that integrates sensing movement (e.g., gait patterns) and delivering cues from either or both the processor/interface/device (e.g., smart phone and associated application) and sensor(s) lends itself to many rehab and research markets stroke and TBI recovery and therapy or treatment of such injuries as well as movement disorders. The cueing device in some embodiments will provide tactile/sensory cueing on the affected body part while the subject performs activities of daily living, which commonly plays an important role and has shown success in in-clinic therapy. The small wearable profile and tactile/sensory cueing will allow the system of the present invention to be worn under clothing during the day without attracting attention that could lead to social stigma, known to discourage community use and increase abandonment of assistive technology.

The systems and methods of the present invention utilize a number of metrics or measures to quantify a subject's disorders and/or symptoms. With respect to movement and movement-related disorders and symptoms, calculating these metrics may include measuring a single movement metric, different movement metrics, or a combination of a number of movement metrics using any sensor which is capable of measuring movement or from which movement-related data may be extracted or calculated; and the movement metric or metrics being measured may include linear or rotational displacement, velocity, or acceleration, or any other metric that could give a quantitative indication of motion; and the part of the body being measured for motion may be a limb (as at a wrist, ankle, or finger) or may be the trunk of the body (as at a shoulder or torso), and the head. Further, kinematic features representative of the subject's movement are additional metrics useful in the scope of the present invention. Useful kinematic features that may be extracted from gyroscopic data may include, for example, peak power angular velocity, peak power angle, RMS angular velocity, frequency, maximum amplitude, maximum peak-to-peak amplitude, mean angular velocity, and wavelet parameters, as well as the covariance or standard deviation over time of any of these metrics. Useful kinematic features that may be extracted from accelerometer data may include, for example, peak power acceleration, peak power velocity, peak power position, RMS acceleration, RMS velocity, RMS position, frequency, maximum amplitude, maximum peak-to-peak amplitude, mean acceleration, and wavelet parameters, as well as the covariance or standard deviation over time of any of these metrics. In a movement data acquisition system, or movement disorder diagnostic measuring apparatus, that combines a three-axis accelerometer and a three-axis gyroscope to produce 6 channels of movement data, one or any combination of the above kinematic features can be extracted from any of the 6 kinematic channels to be used as inputs to a trained scoring algorithm in the next step. The listed kinematic features for the sensors above are intended to be exemplary, and not limiting; other types of sensors will produce different data from which different sets of features may be extracted.

The trained scoring algorithm used to process the kinematic features extracted from the movement data may comprise, for example, one or more of a simple or multiple linear regression, an artificial neural network, a Bayesian network, or a genetic algorithm. The output of the trained scoring algorithm may be a single score or multiple scores of any scale; a single score on the same scale as that of the UPDRS may be preferred in certain applications where simplicity or familiarity is the paramount concern, while more sophisticated scores and scales may be preferred for other advanced applications, such as those that involve recommendations for treatment or closed-loop automated treatment delivery.

Other disorder and/or symptom metrics or measures may be directly measured utilizing the sensors or calculated or derived from one or more direct sensor measurements. The disorder and/or symptom metrics or measures each pertain to different aspects of the subject's physical condition and help provide the system with data that is then used to translate or correlate into a measure of the level or severity of disorder or symptom the subject is experiencing. The disorder and/or symptom metrics or measures can be grouped into separate families or domains based on the particular physical condition, activity or other attribute they are focused on or relevant to.

One such family or domain of metrics or measures includes those related to the subject's physical activity. Physical activity measures or metrics may include, but are not limited to, body postures and the distribution thereof, a burstiness parameter, and an overall activity level. The distribution of body postures measure is a record of the subject's body posture (e.g., seated, standing, reclined, prone, etc.). Body posture can be directly measured from the sensors, typically from at least accelerometers and/or gyroscopes that may be mounted to the subject's torso. The system preferably detects and records the subject's body posture, and further preferably also the amount of time the subject spends in each different posture. The system can them calculate a percentage of time spent in each posture during the time the subject is being monitored. Another disorder or symptom metric or measure related to the subject's physical activity is a parameter of burstiness. In the context of the present invention, burstiness is a measure of the dynamic relationship between periods of rest and activity. This burstiness parameter can be extracted or calculated from measures obtained by accelerometers mounted to the subject. Burstiness is thus a measurement of the increase or decrease in the subject's physical activity. Still another metric or measure related to the subject's physical activity is the subject's overall physical activity level. This measure is a cumulative measure of the subject's movement detected by the system. Typically, overall activity level can best be measured by accelerometers mounted to various parts of the subject's body including torso and limbs. From the cumulative measure of detected movement, the system can calculate the percentage of the monitoring period that physical activity was detected as well as other indications and breakdowns of the amount and type of movement or activity the subject performed, such as amount of activity using particular limbs or parts of the body.

In addition to the percentage of monitoring time that a subject spends in each postural position, a measure or metric relating to the distribution of body postures may be reported as a categorization of the subject's posture, or as a measure of the angle at which the subject's body is positioned. Preferably, the system is able to differentiate between body posture angles of at least 30 degrees. More preferably, the system is able to differentiate between body posture angles of at least 20 degrees. Yet more preferably, the system is able to differentiate between body posture angles of at least 15 degrees. Still more preferably, the system is able to differentiate between body posture angles of at least 10 degrees. Even more preferably, the system is able to differentiate between body posture angles of at least 7 degrees. Still yet more preferably, the system is able to differentiate between body posture angles of at least 5 degrees. Yet still more preferably, the system is able to differentiate between body posture angles of at least 4 degrees. Even still more preferably, the system is able to differentiate between body posture angles of at least 3 degrees. Even yet more preferably, the system is able to differentiate between body posture angles of at least 2 degrees. Most preferably, the system is able to differentiate between body posture angles of 1 degree or less. Further, while measuring the amount of change in body posture angles, the system is preferably able to detect and measure the rate at which the body posture angle is changing which may provide an indication of unsteadiness which may be caused by the subject's disorders and/or symptoms.

With respect to the metric or measure of burstiness, the system is preferably able to detect at least a 50% increase and/or decrease in the subject's physical activity. More preferably, the system is able to detect at least a 40% increase and/or decrease in the subject's physical activity. Still more preferably, the system is able to detect at least a 30% increase and/or decrease in the subject's physical activity. Yet more preferably, the system is able to detect at least a 25% increase and/or decrease in the subject's physical activity. Even more preferably, the system is able to detect at least a 20% increase and/or decrease in the subject's physical activity. Still yet more preferably, the system is able to detect at least a 15% increase and/or decrease in the subject's physical activity. Yet still more preferably, the system is able to detect at least a 10% increase and/or decrease in the subject's physical activity. Even yet more preferably, the system is able to detect at least a 7% increase and/or decrease in the subject's physical activity. Even still more preferably, the system is able to detect at least a 5% increase and/or decrease in the subject's physical activity. Still yet even more preferably, the system is able to detect at least a 3% increase and/or decrease in the subject's physical activity. Most preferably, preferably, the system is able to detect 1% or less increase and/or decrease in the subject's physical activity.

With respect to the measure or metric of overall activity level, the system is preferably able to detect at least a 50% increase and/or decrease in the subject's overall activity level. More preferably, the system is able to detect at least a 40% increase and/or decrease in the subject's overall activity level. Still more preferably, the system is able to detect at least a 30% increase and/or decrease in the subject's overall activity level. Yet more preferably, the system is able to detect at least a 25% increase and/or decrease in the subject's overall activity level. Even more preferably, the system is able to detect at least a 20% increase and/or decrease in the subject's overall activity level. Still yet more preferably, the system is able to detect at least a 15% increase and/or decrease in the subject's overall activity level. Yet still more preferably, the system is able to detect at least a 10% increase and/or decrease in the subject's overall activity level. Even yet more preferably, the system is able to detect at least a 7% increase and/or decrease in the subject's overall activity level. Even still more preferably, the system is able to detect at least a 5% increase and/or decrease in the subject's overall activity level. Still yet even more preferably, the system is able to detect at least a 3% increase and/or decrease in the subject's overall activity level. Most preferably, preferably, the system is able to detect 1% or less increase and/or decrease in the subject's overall activity level.

Another family or domain of disorder and/or symptom metrics or measures that may be used by various embodiments of the present invention includes those metrics and measures related to a subject's mobility. Mobility is different from simple physical activity in that physical activity is a quantitative domain that pertains to the amount of movement or activity a subject performs whereas mobility relates to the subject's actual ability to perform movement or activity and is thus more of a qualitative measure. Mobility metrics or measures also can be directly measured from one or more sensors of the system or calculated, derived or estimated from those sensor measurements. Some examples of metrics or measures that can be considered in the mobility domain include, but are not limited to, leg swing velocity, stride variability, double limb support time, and overall gait speed. Leg swing velocity is a metric or measure that measures the velocity of the subject's leg swing. Further, leg swing velocity measurements can be used to identify gait-related events, such as commencement or ending of gait activity or disturbances in gait, by using the angular velocity measurements. The angular velocity measurements obtained from gyroscopes attached to the subject's lower extremities can further be used to estimate the velocity of different shank segments during the swing phase of the subject's gait. Stride variability is another metric or measure related to the subject's mobility. Stride variability also can be used to detect and identify gait-related events like gait commencement or halting or disturbances in the subject's gait using the angular velocity measurements from gyroscopes. Further, stride variability metrics or measures can be used to estimate standard deviations of the subject's gait cycle for given periods of time. Double limb support time is still another metric or measure that can use angular velocity measurements obtained from gyroscopes attached to the subject's lower extremities to determine gait events, and further can be used to estimate the amount of time that a subject spends supporting himself or herself in double limb support. Overall gait speed is a measure of the subject's gait speed that can be estimated from gyroscopes attached to the subject's lower extremities.

With respect to the measure of leg swing velocity, the system is preferably able to detect changes in the subject's leg swing velocity of at least 50%. More preferably, the system is able to detect changes in the subject's leg swing velocity of at least 40%. Yet more preferably, the system is able to detect changes in the subject's leg swing velocity of at least 30%. Still more preferably, the system is able to detect changes in the subject's leg swing velocity of at least 25%. Even more preferably, the system is able to detect changes in the subject's leg swing velocity of at least 20%. Still yet more preferably, the system is able to detect changes in the subject's leg swing velocity of at least 15%. Yet still more preferably, the system is able to detect changes in the subject's leg swing velocity of at least 10%. Even still more preferably, the system is able to detect changes in the subject's leg swing velocity of at least 7%. Even yet more preferably, the system is able to detect changes in the subject's leg swing velocity of at least 5%. Still even more preferably, the system is able to detect changes in the subject's leg swing velocity of at least 3%. Most preferably, the system is able to detect changes in the subject's leg swing velocity of 1% or less.

With respect to the measure or metric of stride variability, preferably the system is able to accurately detect or measure the variability with a standard deviation of 50% or less. More preferably, the system is able to accurately detect or measure the variability with a standard deviation of 40% or less. Still more preferably, the system is able to accurately detect or measure the variability with a standard deviation of 30% or less. Yet more preferably, the system is able to accurately detect or measure the variability with a standard deviation of 25% or less. Even more preferably, the system is able to accurately detect or measure the variability with a standard deviation of 20% or less. Still yet more preferably, the system is able to accurately detect or measure the variability with a standard deviation of 15% or less. Yet still more preferably, the system is able to accurately detect or measure the variability with a standard deviation of 10% or less. Even still more preferably, the system is able to accurately detect or measure the variability with a standard deviation of 7% or less. Even yet more preferably, the system is able to accurately detect or measure the variability with a standard deviation of 5% or less. Even still more preferably, the system is able to accurately detect or measure the variability with a standard deviation of 3% or less. Most preferably, the system is able to accurately detect or measure the variability with a standard deviation of 1% or less.

With respect to the measure or metric of overall gait speed, the system is preferably able to detect at least a 50% increase and/or decrease in the subject's overall gait speed. More preferably, the system is able to detect at least a 40% increase and/or decrease in the subject's overall gait speed. Still more preferably, the system is able to detect at least a 30% increase and/or decrease in the subject's overall gait speed. Yet more preferably, the system is able to detect at least a 25% increase and/or decrease in the subject's overall gait speed. Even more preferably, the system is able to detect at least a 20% increase and/or decrease in the subject's overall gait speed. Still yet more preferably, the system is able to detect at least a 15% increase and/or decrease in the subject's overall gait speed. Yet still more preferably, the system is able to detect at least a 10% increase and/or decrease in the subject's overall gait speed. Even yet more preferably, the system is able to detect at least a 7% increase and/or decrease in the subject's overall gait speed. Even still more preferably, the system is able to detect at least a 5% increase and/or decrease in the subject's overall gait speed. Still yet even more preferably, the system is able to detect at least a 3% increase and/or decrease in the subject's overall gait speed. Most preferably, preferably, the system is able to detect 1% or less increase and/or decrease in the subject's overall gait speed.

Other measures and metrics related to less direct movement or activity domains are also used in various embodiments of the present invention. One such domain is community participation which relates to the subject's ability to carry on normal daily activities that require the subject to leave his or her home in spite of any pain experienced. The number and duration of trips and stops away from home that the subject takes is a measure or metric that can allow the system to quantify the subject's community participation and can be measured by using GPS tracking data, such as through use of the GPS on a smartphone or any other GPS sensor.

Sleep quality is yet another domain which relates to the subject's level or severity of many disorders and/or symptoms where the disorders and/or symptoms cause the subject to awaken or have trouble falling asleep. The system can measure the number of times the subject awakens and duration sleep by measuring periods of activity during sleep using accelerometer and/or gyroscope data attached to the subject's extremities or torso to determine position and movement during those periods of sleep.

Another important domain is speech, which can provide a strong indication of the presence of or severity of various disorders and/or symptoms, particularly many movement disorders, Alzheimer's or dementia, or pain symptoms that the subject is experiencing. A particularly useful measure or metric in the speech domain is motor control rate and various derivatives or extrapolations thereof, such as the time it takes to form a particular speech pattern or syllable or the variability of pattern or syllable formation rate, and the like. Motor control rate is essentially a measure of the rate at which the subject forms a particular pattern of speech or syllable. The system, in certain embodiments and for various purposes, may allow and optionally instruct the subject to perform a single or series of speech tasks that records a series of vocal samples, for example through the use of a smartphone using an application and the phone's microphone, though other systems are also contemplated for use with such tasks. The system would then analyze the recorded vocal sample to detect the number and accuracy of productions of syllables. The number, frequency and duration of mistakes can be used to determine symptom response of the subject during the task.

With specific respect to the motor control rate, or the rate at which a subject can form a particular speech pattern or syllable, the measure requires identification and detection of the discrete patterns or syllables. Preferably, the system is able to discern the rate at which the subject is able to form speech patterns of 50 syllables or less. More preferably, the system is able to discern the rate at which the subject is able to form speech patterns of 40 syllables or less. Even more preferably, the system is able to discern the rate at which the subject is able to form speech patterns of 30 syllables or less. Still more preferably, the system is able to discern the rate at which the subject is able to form speech patterns of 25 syllables or less. Yet more preferably, the system is able to discern the rate at which the subject is able to form speech patterns of 20 syllables or less. Still yet more preferably, the system is able to discern the rate at which the subject is able to form speech patterns of 15 syllables or less. Yet still more preferably, the system is able to discern the rate at which the subject is able to form speech patterns of 10 syllables or less. Even still more preferably, the system is able to discern the rate at which the subject is able to form speech patterns of 7 syllables or less. Even yet more preferably, the system is able to discern the rate at which the subject is able to form speech patterns of 5 syllables or less. Still even more preferably, the system is able to discern the rate at which the subject is able to form speech patterns of 3 syllables or less. Most preferably, the system is able to discern the rate at which the subject is able to form individual syllables. Further, the system is preferably able to measure and detect the amount of time it takes for the subject to form each pattern or syllable.

Another speech measure or metric that can be correlated to the subject's level or severity of disorders and/or symptoms is the sharpness or crispness of a particular speech pattern or syllable the subject forms. As the subject's disorder or symptom level or severity increases, the sharpness or crispness of words or syllables tends to be dulled. Thus, the system preferably can measure the change in the sharpness or crispness of a particular pattern or syllable in order to determine whether a subject's symptoms are increasing (decreasing sharpness) or decreasing (increasing sharpness). Therefore, the system is preferably able to detect at least a 75% change in the sharpness or crispness of a particular speech pattern, word or syllable. More preferably, the system is able to detect at least a 60% change in the sharpness of a particular speech pattern, word or syllable. Yet more preferably, the system is able to detect at least a 50% change in the sharpness of a particular speech pattern, word or syllable. Still more preferably, the system is able to detect at least a 35% change in the sharpness of a particular speech pattern, word or syllable. Even more preferably, the system is able to detect at least a 25% change in the sharpness of a particular speech pattern, word or syllable. Still yet more preferably, the system is able to detect at least a 15% change in the sharpness of a particular speech pattern, word or syllable. Yet still more preferably, the system is able to detect at least a 10% change in the sharpness of a particular speech pattern, word or syllable. Even still more preferably, the system is able to detect at least a 7% change in the sharpness of a particular speech pattern, word or syllable. Even yet more preferably, the system is able to detect at least a 5% change in the sharpness of a particular speech pattern, word or syllable. Still even more preferably, the system is able to detect at least a 3% change in the sharpness of a particular speech pattern, word or syllable. Most preferably, the system is able to detect 1% or less change in the sharpness of a particular speech pattern, word or syllable.

Still another domain of metrics or measures are those related to autonomic tone and heart rate variability. Autonomous system time domain variability metrics or measures are typically based on physiological signals, for example those based on the beat-to-beat intervals of the subject's heart rate and include standard deviation of the beat-to-beat intervals, proportion of successive intervals that differ my more than a predetermined threshold of time, and standard deviation of successive differences in beat-to-beat intervals. Any physiological signal that provides information as to the subject's autonomic physiological response to stimuli, such as symptoms, may be used with the present invention to provide at least one metric or measure pertaining to the subject's level or severity of disorders and/or symptoms. For example, autonomic system response and/or heart rate variability may be strong indicators of the subject's mood or demeanor, which as noted above are indicators of the subject experiencing symptoms and becoming frustrated, annoyed or angry. Examples of such physiological signals may include electroencephalogram (EEG) which may show the subject's brain-wave response, electrocardiogram (EKG or ECG) which may show the subject's cardiovascular response, electromyogram (EMG) which shows the electrical activity related to muscle movement, magnetic resonance imaging (MRI) which can be used to form images of the subject's body which can provide information as to its physiological state alone or in conjunction with other signals and measures described herein, and the like. Each of these physiological signals varies over time and provides an indication of the physiological status of the subject's body, and thus can be used to track how the subject is responding to disorders and/or symptoms. Other physiological signals may be directly measured or derived from these signals. One particularly important measure or metric is the subject's heart rate. Changes in a subject's heart rate, which may be measured or derived from EKG or ECG signals, may be indicative of a subject's symptom response. Rapid increase in the heart rate, in particular, may indicate frustration or anger as the subject struggles with certain disorders and/or symptoms, for example Alzheimer's or dementia symptoms, chronic pain, or movement disorder symptoms. Another metric or measure that often is linked closely with heart rate in terms of disorders and/or symptoms response is respiration. Such symptoms can similarly lead to increased respiration rates as the heart rate increases. Further still, accompanying such symptom response may be an increase in perspiration which can be detected and measured with a galvanic skin response sensor. All of these responses are autonomic responses to increases in symptoms which can be measured by the system to determine the subject's level of symptoms.

Frequency domain measures or metrics also fall into this domain and involve calculation of the power of beat-to-beat variability in various frequency bands. Typically, the preferred frequency bands utilized are high frequency and or low frequency, depending on the particular embodiment, and also the ratio of the power of the two bands can be used as a separate measure or metric.

The present invention utilizes various algorithm(s) to combine, process, assess and analyze the various metrics or measures and provide output related to the metrics or measures, the subject's disorders and/or symptoms, treatment or therapy for the disorders and/or symptoms, and many other possible outputs and combinations thereof. The different algorithms may be used alone or in conjunction in order to provide various combinations of outputs that would be useful in helping detect, quantify, mitigate and treat a subject's disorders and/or symptoms. Effectively, the algorithms monitor the various measures and metrics described above related to the subject movement, and track the changes in those metrics and measures over time. Such changes in the values of the measures or metrics may be measured through normal activity of the subject providing a picture of the changes as the subject performs those normal activities, or may be measured as a response to applied or delivered therapy or treatment. As noted, the algorithms can be tailored to output data and information in numerous forms, depending on the particular embodiment of the present invention and the needs of the subject.

Some algorithm(s) may be used to process the various measures or metrics and create a disorder and/or symptom index, and may be referred to as disorder and/or symptom quantification algorithms (symptom quantification algorithms, quantification algorithms, scoring algorithms). In some embodiments, the symptom quantification algorithm (s) may take the form of artificial intelligence that is adapted to combine data and/or movement and/or symptom measurements to create an index indicative of the severity or level of the patient's disorders and/or symptoms. Preferably, such artificial intelligence (AI) algorithms may compare, contrast, and/or correlate the instant subject's measured data with a plurality of data, such as in a database, comprising historical data from the instant patient, a plurality of other patients with similar disorders and/or symptoms, or a combination thereof. Historical data preferably includes a combination of relevant patient characteristics, treatment parameters, and results. More specifically, the historical data may include patient demographic and physiological or physical information such as age, weight, race, gender, ethnicity, activity levels (e.g., very active, moderately active, sedentary, etc.). Also preferably, the historical data includes information on each subject's diseases, disorders, and/or injuries, symptoms thereof, scores, indexes or other quantifications of the disorders and/or symptoms, duration and length of time suffering from or experiencing such disorders and/or symptoms, and the like. Further, the historical data preferably includes data related to any treatments or therapies (e.g., electrical stimulation such as DBS, FES, spinal cord stimulation, or the like; medications or drugs the subject has used, both prescription and over the counter (OTC), as well as the delivery mechanism for such drugs, such as implanted closed-loop or semi-closed loop drug pumps, injections, transdermal patches, oral medications such as liquids, pills, tablets, and the like, as well as the doses and instructions for taking the medications or drugs such as timing between doses, time of day, with or without meals, with or without other drugs or medications either prescription or OTC, and the like) the subject has been prescribed or otherwise tried and the results of those treatments or therapies. Preferably, the results of the treatments or therapies include the effects that such treatments or therapies had on the subject's disorders and/or symptoms quantitatively (e.g., indexes or scores representing the severity or level of the disorders and/or symptoms when on and/or off of the treatment or therapy, length of time between recurrences of disorders and/or symptoms, duration of the occurrence of disorders and/or symptoms, and the like) and/or qualitatively (e.g., subjective data representing the subject's thoughts, feelings, impressions, ratings of his or her disorders and/or symptoms (including subjectively quantitative scores or indexes), and other subject-diary entries including activity tracker data, diet tracker data, mood inputs, and the like. This AI correlation process preferably utilizes the historical information to more accurately and precisely guide the determination of the instant subject's disorder and/or symptom severity by using the plurality of historical data to narrow down the results and base the analysis on those data points that are most similar or related to those of the instant subject. The AI algorithms take into account all available data in determining the data points that are most relevant and applicable to the instant subject's current status and condition, and thus informs its calculations based on the data that is most likely to yield positive results for the instant subject. The result, as stated, is the calculation of a disorder and/or symptom index that is preferably a quantitative, numerical index value that provides a clear representation of the level, amount or severity of the subject's disorders and/or symptoms. The disorder and/or symptom index may also be referred to as a symptom index, disorder and/or symptom score, severity score, or quantified score. The symptom index can be provided according to any numerical scale (e.g., from 0 to 10, or 1-100), and can be tailored to be presented in any numerical form (e.g., whole numbers, integers, fractional numbers). Preferably, for the sake of ease and rapid interpretation, the symptom index is presented as a positive integer and the scale is adjusted to provide the amount of detail required. The symptom quantification algorithm may optionally employ any one, or a combination of, mathematical models currently known to those in the art, including, but not limited to linear and non-linear classification methods such as logistic regression, artificial neural networks, k-means clustering, genetic algorithms, and the like in order to analyze and process the various metrics or measures and translate them into a symptom index value. Preferably, an artificial neural network, genetic algorithm, or other such advanced type of algorithm is used when correlating with a database in order to provide rapid and robust optimization and AI functionality in calculating the symptom severity index.

Other algorithm(s) may not output a numerical value representing the disorder and/or symptom or disability level or severity, but rather may output a visual representation, or disorder and/or symptom response or severity map (symptom response map, symptom severity map). Such algorithms may be referred to as disorder and/or symptom severity mapping algorithms or mapping algorithms. These mapping algorithms may also preferably operate in conjunction with the AI disclosure above to optimize the results using historical data in a similar manner as the scoring algorithms. A disorder and/or symptom response or severity map, described in greater detail below, is a visual representation depicting the measured or calculated values of various variables (e.g., symptom metrics or measures) obtained as a result of known variables surrounding the subject's activity, state or condition. For example, if the subject is provided with a known type of therapy under known parameters, the system can measure and calculate the various metrics or measures as a result of the known therapy parameters, and populate the map with values for the metrics or measures as a result of those parameters. The disorder and/or symptom response or severity map thus visually depicts the values of various metrics and measures, as well as the level of the subject's disorders and/or symptoms. The maps can take on any form that usefully portrays the data to a clinician or user for analysis. One preferred embodiment presents the data as follows: columns represent objectively measured, calculated or estimated metrics or measures as obtained from the sensors of the system, rows represent different variables or parameters of the subject's movement or activity such as types of therapies, therapy parameters, (e.g., drug dosage, stimulation parameters, or the like), and the individual points (intersections of column and row vertices) are somehow coded to represent the resultant symptom or disability intensity, for example by color-coding, shading, pattern, or the like. Thus, for mapping algorithms that populate a disorder and/or symptom response or severity map, the objectively measured metrics or measures are analyzed and processed in such a way that the resulting symptom intensity is displayed visually as a map depicting multiple responses to various parameters or variables, as opposed to the single, perhaps momentary numerical index presented by other algorithms.

An output device is also part of many embodiments of the present invention and is adapted to provide some output, feedback, information or other communication. Preferably, the output device includes at least a visual display device, and more preferably a display that also functions as a user interface, in many embodiments of the present invention. Preferably, the user interface is a graphical user interface (GUI) that both presents information to the user (e.g., subject, clinician, physician, technician, researcher, and the like) and allows the user to interact with the device whether via touchscreen interface, buttons, dials, keyboard and mouse, hand or eye movements and gestures, or other such input devices known in the art. The display device may include any of smartphones, televisions, computer or laptop monitors, tablets, eyewear (e.g., eyeglasses, sunglasses, goggles, standalone devices attached to eyewear, and the like), vehicle windshield, heads up displays, projections, or any other such medium where one could reasonably expect to notice a visual indication or message displayed. Visual indicators or messages are preferably displayed in a noticeable, conspicuous manner so as to effectively notify the subject, but not in an invasive or distracting manner such that the subject's attention is completely diverted from whatever task or activity of daily living he or she is performing (e.g., driving). The visual indicator or message may take on many and various forms, including, but not limited to a representation (e.g., numerical index) of the quantified level or severity of disorders and/or symptoms (e.g., symptom index or score), a warning or message regarding any aspect or part of the device or use of the device (e.g., low battery, poor sensor contact or signal, loss of communication, etc.), any aspect or part of the measurement, analysis or treatment functions (e.g., treatment or therapy protocols such as stretches or exercises to alleviate movement-related symptoms, measurement values obtained from the sensors, an indicator that the quantified symptom severity or level has exceeded a threshold and treatment or therapy is recommended ore required, notification to take a self-administered medication, etc.), and the like. The display device may also be used to view data and to enter data into the system. For example, the display device may preferably be a smartphone wherein the screen of the smartphone can provide any of the above messages to the user or clinician, but where, for example, the user can further interact with the device to input personal symptom data, or the clinician or a technician can input initial data for the system's operation. Most preferably, the display is capable of displaying multiple types and forms of data, messages, warnings and other information simultaneously and also of emphasizing certain information based on importance or potential emergency. For example, if the drug titration device is set to provide much too high of a dose, the display might flash a warning to gain a user's attention to prevent overdosing the subject. Additionally, other output devices may be used to help provide any data, message or warning, such as audio output devices to provide an audible form of the information displayed on the display.

The display device may be integrated into the portable symptom measurement and quantification device, or may be separate therefrom and independent or part of another device or system, such as a smartphone, computer or tablet. Wired tethering or connection to a visual display may be feasible in some embodiments, such as if the visual display is part of a video game system the subject is playing while stationary, worn on the subject such as in the form of eyewear or a heads up display, or perhaps in a vehicle—in other words only embodiments where the subject is substantially stationary and wired connections are not a hindrance or embarrassment to the subject. Even in those circumstances, however, wireless communication is still preferred when possible.

As noted, preferably the system includes a GUI allowing a user to interact with the measurement/quantification and/or treatment devices. The GUI preferably is adapted to display information to the user as well as for the user to input information to the system, and in some embodiments to communicate with a remote system and/or clinician, physician, or technician. The GUI may be used to display raw measured data from the sensors of the system (e.g., electrophysiological or physiological signals, raw or preprocessed signals from sensors). The GUI preferably is adapted to at least display any calculated indices, such as symptom severity indices or scores for the subject or other user to readily see and be able to ascertain the objective quantified severity of their disorder(s) and/or symptom(s). The score or index may be represented purely as a numerical value, but preferably, the numerical value may be further indicative of the relative severity based on predetermined or adaptive thresholds. For example, if the severity is within normal ranges that are not particularly strong or troublesome to the subject, the index or score may be depicted as the numerical value in green or white, but if the index or score is indicative of a high, painful, or particularly strong level of severity, then the index or score may be presented in red, as a flashing numerical value, or other such indication that the value is above the preferred threshold. This representation of the index preferably allows and enables the subject to initiate treatment or therapy when the index or score is indicative of a severity that is increasing or is already above the preferred threshold. Different disorders and/or symptoms may use different thresholds, and the thresholds may be adaptive in that the threshold value may be changed to better suit the subject's particular activity, surroundings, environment, or condition. For example, if the subject is going to sleep, he or she may input to the system that he or she is doing so, and the threshold might be lowered so that if the disorder and/or severity index approaches the lower threshold the system can notify the subject to take medication so that the symptoms do not become too severe and thus interrupt or otherwise perturb the subject's sleep. However, if the subject is relaxing at home or out performing activities of daily living (e.g., eating, shopping, exercising, and the like), and he or she is able to tolerate a higher level or severity of disorder and/or symptoms, then the threshold may be raised in order to only provide instructions for therapy if the disorder and/or symptoms approach or exceed the higher threshold. Preferably the subject is able to input preferred threshold levels based on his or her own tolerance and preference levels. The subject may be able to input specific threshold values for the index or score, or may merely select a more qualitative threshold (e.g., high severity, medium severity, low severity) and the system will automatically select a threshold for that qualitative level. For the qualitative threshold levels, preferably a physician, clinician, or technician determines the threshold for each representative level, or the system may automatically determine the qualitative threshold values using an AI algorithm and calculating the optimal threshold value based on a database of historical data comprising such threshold values for other subjects and/or the instant subject's past thresholds. THE GUI may further be adapted to output additional signals, such as an audible alarm or notification or visual message or indicator (e.g., flashing screen or icon, color changes) in order to obtain the subject's attention when the index or score changes in a manner significant to require attention or action by the subject.

Preferably, the GUI is part of the software app described above and thus incorporates the subject input capabilities in association with the software app. Notably, the GUI preferably allows the subject to input diary entries including diet information (e.g., tracking and inputting foods eaten or planned to eat), activity logging (e.g., exercises or activities of daily living performed), subjective physiological and mental status input (e.g., perceived level or severity of disorders and/or symptoms, energy level, mood, stress, and the like), objective measured status (e.g., blood pressure, temperature, other physiological measurements taken by sensors from those associated with the devices and systems or measured by a clinician, physician, or technician—these external measurements may be redundant o those associated with the devices and systems of the present invention, such as for verification or calibration), and the like. When the subject inputs any of such data, the algorithms of the present invention incorporate such data into their calculations. This may not affect the quantification or scoring algorithms in many embodiments, though it me be used in scoring for some other embodiments. Preferably, all subject-input data is used by a treatment or therapy algorithm, along with all measured and calculated data, in order to provide a recommended treatment or therapy to the subject and/or to a clinician, physician, or technician. With regard to the GUI, preferably, the treatment or therapy algorithm outputs a recommended therapy or treatment at least via the GUI to the subject instructing the subject on what treatment or therapy is recommended and when it should be performed. This is particularly useful for self-administered medication or drug treatment or therapy where the system can determine a change in the level or severity of the subject's disorder and/or symptoms and notify the subject to take a particular dose of medication. Such instructions may be preventative in order to maintain a level or severity of the disorder or symptoms before a prior dose of medication or other treatment begins to wear off, or otherwise as the worsening disorder or symptom severity approaches or crosses the threshold. The instructions may also be provided such that the subject takes the medication only when the disorder and/or symptom severity crosses the threshold and the worsening disorder and/or symptoms start to become disruptive to the subject. As mentioned above, all drug titration recommendations are preferably made within the particular drug's intended uses and indications of use, and are preferably cross-referenced with other medications and treatments the subject is undergoing or using to ensure safe treatment.

As noted above, the present invention may be used in conjunction with other treatment, therapy or assistance devices, systems and modalities, such as with electrical stimulation devices, pharmaceutical delivery devices (e.g., drug titration and delivery systems, drug pumps, implanted or externally worn), and other such systems and devices. Such treatment, therapy or assistance devices and/or methods are intended to be complementary, and possibly even secondary considerations to the disorders and/or symptoms measurement and quantification of the system, but to operate in a synergistic manner such that the measurement and quantification device can be used to control and complement the treatment or therapy device to best supply the proper amount, type or level of treatment or therapy to the subject. Examples of such treatment, therapy or assistance devices and/or methods include electrical stimulation devices such as deep brain stimulation (DBS), functional electrical stimulation (FES devices), transcranial direct current stimulation (tDCS) devices, and spinal cord stimulation devices, and medication or drug delivery devices such as closed-loop or semi-closed loop drug or medication titration and delivery systems, each of which is described in greater detail below, or can include providing suggestions for stretches, exercises, movement, activities (e.g., take a bath or shower, lie down or sit up, etc.), diet changes (e.g., avoid certain foods, increase certain foods, eat a particular food item at a particular time or interval, etc.), changes in habit (e.g., change sleeping routine, get a certain amount of exercise, etc.), routine or activities, changing environmental conditions (e.g., change room temperature, change lighting, etc.) or other such actions the subject can perform to prevent, alleviate or otherwise address his or her disorders and/or symptoms. The drug delivery device may also include devices for assisting or facilitating the administration of self-administered drugs or medications. Such devices may include an actuator that, upon the system's providing notification to the subject that it is time to take a dose of, for example, an oral medication such as a pill, opens a pill box or drug dispensing device that makes the proper dose of the drug or medication readily available to the subject or clinician to retrieve and administer. Similarly the actuator may automatically fill a syringe to the proper dose and dispense it to the subject for injection. In other words, drug delivery devices may include actuators and other systems that not only notify the subject or clinician that a dose is recommended, but then make the drug available in the proper dose for administration. The main object of the present invention is to measure and quantify the subject's disorders and/or symptoms so that the subject and/or clinician can become aware of the root cause of the subject's disorders and/or symptoms and understand the exact nature thereof, and this increased knowledge and understanding can lead to a more effective and targeted approach to addressing the subject's disorders and/or symptoms. Through continuous use of the system, it is intended for the subject and clinician arrive at not only a long-term treatment plan involving passive treatments that mask reduce or minimize the subject's disorders and/or symptoms temporarily, but also to incorporate preventative and "curative" treatments and therapies that help address the root cause of the disorders and/or symptoms and thus can help to, over time, completely alleviate the subject's disorders and/or symptoms when possible depending on the type and nature thereof. However, it is conceivable that there may be disorders and/or symptoms and root causes thereof too severe for the subject to address merely by changing aspects of his or her movement, posture, activity, or the like. Therefore, it is very likely that numerous treatment or therapy modalities, devices, methods, or the like will be used simultaneously or at various stages in the process of the subject's treatment. In these embodiments, the included treatment, therapy or assistance device(s) would possibly only activate, or be able to activate, under circumstances where the disorders and/or symptoms severity or level is too severe or where the root cause has yet to be identified. In the case of a DBS device, the system may activate the DBS device to provide an electrical stimulus to the subject's brain in order to initiate proper movement or motion to avoid symptomatic movement. DBS devices and methods such as those described in U.S. Pat. No. 9,662,502 issued on May 30, 2017, U.S. Pat. No. 9,393,418 issued on Jul. 19, 2016, U.S. Pat. No. 9,211,417 issued on Dec. 15, 2015, U.S. Pat. No. 9,289,603 issued on Mar. 22, 2016, and U.S. Pat. No. 9,238,142 issued on Jan. 19, 2016 are quite useful in light of or with the present invention, and are herein incorporated by reference. Similarly, with an FES device, the system may activate the FES device to provide electrical stimulation to a particular muscle to help the subject perform the necessary movement correction. Another implanted electrical stimulation treatment or therapy includes spinal cord stimulation devices which may be implanted in the subject to deliver electrical stimulation directly to the subject's spinal cord to alleviate disorders and/or symptoms when the precise cause can be isolated and identified to be in the subject's spinal cord. A drug or medication titration and delivery system may be utilized to administer, for example, pain medication of some variety. Additionally or alternatively, treatment or therapy may be provided in the form of instructions, suggestions or other such guidance on drugs or medications to take including dosage, timing, and other indications or instructions such as with meals or avoid taking with other medications, or instructions as to activities, movements, exercises, stretches, dietary changes, habit or activity changes, or the like for the subject to perform to address causes of the disorders and/or symptoms that are based in some aspect of the subject's movement, posture, motion, or the like. This type of therapy can be delivered directly to the output device and/or GUI of the subject's device, or any other such display, in any format that provides sufficient instruction to the subject to carry out the particularly instructed drug dosing or exercise, stretch, movement or correction. These devices are not intended to be an exclusive list of potential treatment, therapy or assistance devices contemplated for use with the present invention, but merely exemplary selections intended to show the type of devices contemplated for use and the manner in which they are best used in conjunction with the present invention.

Many embodiments of the present invention further include one or more reporting functions and steps for monitoring the use of the systems and methods and managing the subject's disorders and/or symptoms. These reporting methods are particularly useful for embodiments involving the recommendation and/or dispensing or providing of self-administered medications to the subject. For example, in some embodiments, the subject may be required to, or optionally be able to, report via the device(s) that he or she is taking a medication from a supply, which functions to monitor the use of the subject's medication. Alternatively, the system may automatically record and report when a drug dose is recommended, thus monitoring when the subject's prescription is expected to run out and or a refill would be required or expected. This further has the benefit of preventing or at least reducing the risk of overuse of the drug or medication by the subject by providing a level of oversight of the drug or medication use. Some embodiments of the system may also prompt the subject to order refills when needed or expected, or may automatically order such refills. Preferably, such reports and any refill requests are also transmitted or provided to a clinician, physician, or technician for review and notification purposes so that the clinician, physician, or technician can note and record such activity. Further, the clinician, physician, or technician may be able to monitor for misuse of the dug or medication, and further may be able to exercise approval authority over any refill requests. Still further, the data may be reported to the clinician, physician, or technician so that he or she may review the drug, drug dose, and instructions for safety and efficacy, and to make alternative recommendations if necessary.

Many method embodiments of the present invention include a step of providing a portable measurement and quantification system or device to a subject. The portable measurement and quantification system or device preferably, as described herein, comprises at least one sensor having a signal, a processor comprising an algorithm and an output, an output device, and in some embodiments a pain treatment or therapy device. The portable measurement and quantification system or device may be a single enclosure with all components embedded, integrated or otherwise contained within or attached to the single enclosure. Alternatively, the portable measurement and quantification system or device may comprise an electronics housing or enclosure with the at least one sensor(s) placed radially on one or more parts of the subject's body and in communication, either wired or wireless, with the electronics housing or enclosure or processing device or component (i.e., smartphone, computer, standalone processing device). The signal of the at least one sensor may also depend on the particular embodiment utilized. In some embodiments, the signal from the at least one sensor may be related to the subject's movement, may be related to voluntary and/or involuntary movement, and may be as specific as movement of a particular limb or portion of the subject's body, or as general as overall movement of the subject's body as a whole. Other sensors as described herein may be utilized as well, either alone or in conjunction with such movement sensors. In other embodiments, the signal of the at least one sensor may be related to a response of the subject's autonomous nervous system to a stimulus, such as pain, and can be of any variety discussed herein. The signal of the at least one sensor may depend on the particular sensors used (e.g., accelerometer and gyroscope as opposed to EMG electrode, GSR sensor, temperature sensor, etc.), the placement of the sensor(s), or the particular condition, movement, disorder or other such impairment that is causing the subject's disorders and/or symptoms. Similarly to the at least one sensor, the treatment or therapy device may also be embedded, integrated or otherwise attached to the portable measurement and quantification system or device or may be a separate component in communication with the electronics housing or enclosure or processing device or component (i.e., smartphone, computer, standalone processing device). The exact nature of the portable measurement and quantification system or device depends on the particular use. By way of non-limiting example, in an embodiment used for overcome chronic back pain, the portable measurement and quantification system or device may include all components in a single enclosure, including at least one sensor and the pain treatment or therapy device, and might be worn discreetly about the subject's torso or abdomen attached to a strap or harness. Such a device may require at least one gyroscope and/or at least one accelerometer, which can be installed into the device enclosure of the therapy device, and the treatment or therapy device might be a cueing device or a temperature element that can provide heat or cooling to the subject, and can be similarly installed into the device enclosure, or into the strap or harness. When the system of this exemplary embodiment detects back pain of the subject based on the signals of the at least one sensor, the treatment or therapy would provide a cue for the subject to correct his or her posture (for a cueing treatment or therapy device) or provide heat, cold, or cycle between heat and cold to help ease the pain the subject is suffering. Alternatively, in another non-limiting example, the sensors may include electromyogram electrodes placed on the subject's arms or legs, or other parts of the body, to measure the muscle movement therein, and the device enclosure may be a centralized unit attached to or carried by the subject while in communication with the remote sensors. The treatment or therapy device in such example might be separate from the portable measurement and quantification device and take the form of a drug titration and/or delivery system. In this example, the remote sensors measure the subject's muscle movement and transmit their signals back to the device enclosure which, upon measuring and quantifying the subject's pain, triggers the drug titration and/or delivery device to provide a drug or medication to the subject to alleviate the pain he or she is suffering. In yet another example, the system may be used for treating a movement disorder, much like the example immediately preceding this one, but instead of a drug titration and/or delivery device, the system outputs instructions to a GUI on the subject's smartphone instructing the subject to take an oral medication, whether it be a pill or liquid, in a specified time frame in order to prevent the onset or increase in severity of the subject's movement disorder symptoms. In yet another example, the subject's Alzheimer's or dementia symptoms may begin to worsen and the system, upon measurement and detection of such increase in symptoms, instructs the subject that either a new transdermal medication patch needs to be applied or an injection of a given medication is recommended. The combinations of disorder and/or symptoms, elements of the system, and treatment modalities are all interchangeable based on a particular subject's condition and situation, and in cooperation with his or her clinician, physician, or technician.

In any such embodiment of the portable measurement and quantification system or device must first be provided to the subject. Providing the device to the subject may require a nominal amount of training, instruction or assistance to familiarize the subject with the device and its use. Such training may occur in the clinical setting where a physician, clinician, therapist or technician guides the subject in the donning, doffing and use of the portable measurement and quantification system or device and the particular or various embodiments that the particular subject may utilize. Alternatively, or in addition, video, audio or telecommunication instruction may be made available to the subject such that the subject may become acquainted with, or reacquainted with, the instructions for use of the device outside of the clinical setting, and thus not requiring a special, separate clinical appointment for retraining or recollection on the use of the device. Such non-clinical instruction may be provided through video medium (e.g., DVD, video file provided through a smartphone or tablet application) provided with the device, audio recording (e.g., .mp3 format sent to subject for remote access, on the portable device itself, provided through a smartphone or tablet application), or through teleconference or video conference whereby the subject interacts directly with the physician, clinician, therapist or technician and is walked through the use and operation of the device. Such initial and ongoing training, instruction or assistance ensures that the subject is always able to safely, properly and effectively use the system.

Once the portable measurement and quantification system or device has been provided to the subject and the subject is comfortable and knowledgeable as to the use of the device, the subject may then utilize the system in the manner best fitting his or her particular needs, preferably as discussed and agreed upon with the physician, clinician, therapist or technician. The subject preferably is able to use the portable measurement and quantification system or device, including all physical and electrical parts, including donning and doffing the device and navigating any software, user interface (GUI or otherwise) or other interactive and/or virtual components of the system required to effectively and safely measure the subject's movement and/or other physiological signals or indicators of disorders and/or symptoms, and provide the particular desired outcome, whether it be treatment, therapy, training, or any other such output the system is able to provide.

Many embodiments of the present invention include the step of measuring some aspect, characteristic, signal or metric from the subject. The particular measurement taken is determined by the particular embodiment, and thus the particular needs of the subject and the sensors utilized with the particular embodiment. Measurements, or data acquisition, may be performed a single time or multiple times, iteratively over an extended period of time, or may even be performed substantially continuously for the entire time the subject has the device with or attached to him or her. Preferably, for all embodiments, the measurement time adheres to the above described time periods for measurement (real-time measurement and quantification), treatment or therapy delivery time, and measurement-to-treatment time. As noted herein, the system may be adapted to measure the subject's movement, a response of the subject's autonomous nervous system to a stimulus, voice or speech, physiological biopotential signals such as EMG, EEG, ECG/EKG, EOG, and the like, or any other similar metric of the subject that relates to the subjects disorders and/or symptoms.

For embodiments that include measuring the subject's movement, more specifically the external body movement or motion, or a physiological signal associated with external body movement or motion with the at least one sensor of the portable diagnostic/measurement and therapy systems or devices, the measurement is performed using the various sensors described herein to measure the subject's body motion. As noted, typical sensors may include at least one of, or combinations of, gyroscopes, accelerometers, EMG electrodes, magnetometers, resistive bend sensors, load cells, and the like. The various sensors can be placed on any part of the subject's body such that the sensor can measure the movement of that part of the body and effectively provide movement data that can be used to measure the subject's movement and quantify the subject's disorders and/or symptoms from those measurements. The sensors acquire their respective signals and transmit those signals to the electronic components of the portable measurement and quantification device. The particular transmission method determines on the format of the particular embodiment. As noted herein, some embodiments may include sensors embedded in, integrated in or attached to the device enclosure of the portable measurement and quantification device and thus the device enclosure would likely include internal hard-wired communication circuitry between the sensor(s) and the electronics of the device, and other embodiments may include separate, remotely-placed sensors which may utilize wires or cords to connect the sensors to the electronics in the device enclosure or, more preferably, communicate wirelessly with the electronic components. Wireless communication requires at least one electronic component for transmission of the signal from the sensor and at least one electronic component for receiving the signal by the device enclosure. Preferably, such wireless communication components are each capable of two-way communication such that the remotely-placed sensors and the electronics of the portable diagnostic/measurement and therapy systems or devices are each capable of transmitting and receiving signals and data to and from each other. This is particularly preferable for embodiments including a treatment or therapy device that is separate from the portable measurement and quantification device and local to the remote sensor locations, and thus allows the device to provide treatment or therapy directly to the particular part of the subject's body.

Further preferably, the one or more electronic components also filter (and possibly amplify) the detected movement, physiological, electrophysiological, or other sensor signals, when necessary, and more preferably convert these signals into a digital signal when the acquired signal is in analog form. The one or more electronic components are attached to, worn, carried, or otherwise borne by the subject as part of device or system. Further preferably, the one or more electronic components can receive a signal from local devices and systems, remote devices and systems, or other remote transmitters. The one or more electronic components may include circuitry for but are not limited to for example electrode amplifiers, signal filters, analog to digital converter, blue tooth radio, a DC power source, and combinations thereof. The one or more electronic components may comprise one processing chip, multiple chips, single function components or combinations thereof, which can perform all of the necessary functions of detecting signals from the various sensors, storing that data to memory, uploading data to a local or remote external system or database, transmitting a signal corresponding to sensor signal to a local or remote external system or database, and optionally receiving a signal from a remote transmitter as part of another system or device. These one or more electronic components can be assembled on a printed circuit board or by any other means known to those skilled in the art. Preferably, the one or more electronic components can be assembled on a printed circuit board or by other means so its imprint covers an area less than 4 $in^2$, more preferably less than 2 $in^2$, even more preferably less than 1 $in^2$, still even more preferably less than 0.5 $in^2$, and most preferably less than 0.25 $in^2$.

Preferably, the circuitry of the one or more electronic components is appropriately modified so as to function with any suitable miniature DC power source. More preferably, the DC power source is a battery. The most preferred battery of the present invention is lithium powered batteries. Lithium ion batteries offer high specific energy (the number of given hours for a specific weight), which is preferable. Additionally, these commercially available batteries are readily available and inexpensive. Other types of batteries include but are not limited to primary and secondary batteries. Primary batteries are not rechargeable since the chemical reaction that produces the electricity is not reversible. Primary batteries include lithium primary batteries (e.g., lithium/thionyl chloride, lithium/manganese dioxide, lithium/carbon monofluoride, lithium/copper oxide, lithium/iodine, lithium/silver vanadium oxide and others), alkaline primary batteries, zinc-carbon, zinc chloride, magnesium/manganese dioxide, alkaline-manganese dioxide, mercuric oxide, silver oxide as well as zinc/air and others. Rechargeable (secondary) batteries include nickel-cadmium, nickel-zinc, nickel-metal hydride, rechargeable zinc/alkaline/manganese dioxide, lithium/polymer, lithium-ion and others.

Preferably, the circuitry of the one or more electronic components comprises data acquisition circuitry further including an amplifier that amplifies the sensor signals (particularly electrophysiological signals such as EEG, EMG, EOG, EKG/ECG, and the like as kinetic sensor signals (e.g., accelerometer, gyroscope, magnetometer) or other sensor signals (e.g., video, audio) may not need to be amplified). The data acquisition circuitry is designed with the goal of reducing size, lowering (or filtering) the noise, increasing the DC offset rejection and reducing the system's offset voltages. The data acquisition circuitry may be constrained by the requirements for extremely high input impedance, very low noise and rejection of very large DC offset and common-mode voltages, while measuring a very small signal of interest. Additional constraints arise from the need for a "brick-wall" style input protection against ESD and EMI. The exact parameters of the design, such as input impedance, gain and passband, can be adjusted at the time of manufacture to suit a specific application via a table of component values to achieve a specific full-scale range and passband.

More preferably, a low-noise, lower power instrumentation amplifier is used. The inputs for this circuitry is guarded with preferably, external ESD/EMI protection, and very high-impedance passive filters to reject DC common-mode and normal-mode voltages. Still preferably, the instrumentation amplifier gain can be adjusted from unity to approximately 100 to suit the requirements of a specific application. If additional gain is required, it preferably is provided in a second-order anti-bias filter, whose cutoff frequency can be adjusted to suit a specific application, with due regard to the sampling rate. Still preferably, the reference input of the instrumentation amplifier is tightly controlled by a DC cancellation integrator servo that uses closed-loop control to cancel all DC offsets in the components in the analog signal chain to within a few analog-to digital converter (ADC) counts of perfection, to ensure long term stability of the zero reference.

Preferably, the acquired analog signals are converted to a digital form. This can be achieved with an electronic component or processing chip through the use of an ADC. More preferably, the ADC restricts resolution to 16-bits due to the ambient noise environment in such chips. Despite this constraint, the ADC remains the preferable method of choice for size-constrained applications such as with the present invention unless a custom data acquisition chip is used because the integration reduces the total chip count and significantly reduces the number of interconnects required on the printed circuit board.

Preferably, the circuitry of any sensor board of the present invention comprises a digital section. The heart of the digital section of the sensor board may the Texas Instruments MSP430-169 microcontroller, or another microcontroller with similar characteristics and capabilities, or more preferably more advanced characteristics and capabilities. The Texas Instruments MSP430-169 microcontroller, for example, contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry of any transceiver module of the present invention also comprises a digital section. More preferably, the heart of the digital section of the sensor board may be the Analog Devices ADVC7020 microcontroller, or another microcontroller with similar characteristics and capabilities, or more preferably more advanced characteristics and capabilities. The Analog Devices ADVC7020 microcontroller, for example, contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry for the one or more electronic components comprises nonvolatile, rewriteable memory. Alternatively, if the circuitry for the one or more electronic components doesn't comprise nonvolatile, rewriteable memory then an approach should be used to allow for reprogramming of the final parameters such as radio channelization and data acquisition and scaling. Without nonvolatile, rewriteable memory, the program memory can be programmed only once. Therefore one embodiment of the present invention involves selective programming of a specific area of the program memory without programming the entire memory in one operation. Preferably, this is accomplished by setting aside a specific area of program memory large enough to store several copies of the required parameters. Procedurally, this is accomplished by initially programming the circuitry for the one or more electronic components with default parameters appropriate for the testing and calibration. When the final parameters have been determined, the next area is programmed with these parameters. If the final testing and calibration reveals problems, or some other need arises to change the values, additional variations of the parameters may be programmed. The firmware of various embodiments of the present invention scans for the first blank configuration block and then uses the value from the preceding block as the operational parameters. This arrangement allows for reprogramming of the parameters up to several dozen times, with no size penalty for external EEPROM or other nonvolatile RAM. The circuitry for the one or more electronic components has provisions for in-circuit programming and verification of the program memory, and this is supported by the breakoff test connector. The operational parameters can thus be changed up until the time at which the test connector is broken off just before shipping the final unit. Thus the manufacturability and size of the circuitry for the one or more electronic components is optimized.

Preferably the circuitry of the one or more electronic components includes an RF transmitter which may be a Bluetooth radio as described herein. Another feature of the circuitry of the one or more electronic components preferably is an antenna. The antenna, preferably, is integrated in the rest of the circuitry. The antenna can be configured in a number of ways, for example as a single loop, dipole, dipole with termination impedance, logarithmic-periodic, dielectric, strip conduction or reflector antenna. The antenna is designed to include but not be limited to the best combination of usable range, production efficiency and end-system usability. Preferably, the antenna consists of one or more conductive wires or strips, which are arranged in a pattern to maximize surface area. The large surface area will allow for lower transmission outputs for the data transmission. The large surface area will also be helpful in receiving high frequency energy from an external power source for storage. Optionally, the radio transmissions of the present invention may use frequency-selective antennas for separating the transmission and receiving bands, if a RF transmitter and receiver are used on the electrode patch, and polarization-sensitive antennas in connection with directional transmission. Polarization-sensitive antennas consist of, for example, thin metal strips arranged in parallel on an insulating carrier material. Such a structure is insensitive to or permeable to electromagnetic waves with vertical polarization; waves with parallel polarization are reflected or absorbed depending on the design. It is possible to obtain in this way, for example good cross polarization decoupling in connection with linear polarization. It is further possible to integrate the antenna into the frame of a processing chip or into one or more of the other electronic components, whereby the antenna is preferably realized by means of thin film technology. The antenna can serve to just transfer data or for both transferring data to and for receiving control data received from a remote communication station which can include but is not limited to a wireless relay, a computer or a processor system. Optionally, the antenna can also serve to receive high-frequency energy (for energy supply or supplement). In any scenario, only one antenna is required for transmitting data, receiving data and optionally receiving energy. Optionally, directional couples can be arranged on the transmitter outputs of the electrode patch and/or the remote communication station. The couplers being used to measure the radiated or reflected radio wave transmission output. Any damage to the antenna (or also any faulty adaptation) thus can be registered, because it is expressed by increased reflection values.

An additional feature of the present invention is an optional identification unit. By allocating identification codes—a patient code, the remote communication station is capable of receiving and transmitting data to several subjects, and for evaluating the data if the remote communication station is capable of doing so. This is realized in a way such that the identification unit has control logic, as well as a memory for storing the identification codes. The identification unit is preferably programmed by radio transmission of the control characters and of the respective identification code from the programming unit of the remote communication station to the patient worn unit. More preferably, the unit comprises switches as programming lockouts, particularly for preventing unintentional reprogramming.

In any RF link, errors are an unfortunate and unavoidable problem. Analog systems can often tolerate a certain level of error. Digital systems, however, while being inherently much more resistant to errors, also suffer a much greater impact when errors occur. Thus the present invention when used as a digital system, preferably includes error control sub architecture. Preferably, the RF link of the present invention is digital. RF links can be one-way or two-way. One-way links are used to just transmit data. Two-way links are used for both sending and receiving data.

If the RF link is one-way error control, then this is preferably accomplished at two distinct levels, above and beyond the effort to establish a reliable radio link to minimize errors from the beginning. At the first level, there is the redundancy in the transmitted data. This redundancy is performed by adding extra data that can be used at the remote communication station or at some station to detect and correct any errors that occurred during transit across the airwaves. This mechanism known as Forward Error Correction (FEC) because the errors are corrected actively as the signal continues forward through the chain, rather than by going back to the transmitter and asking for retransmission. FEC systems include but are not limited to Hamming Code, Reed-Solomon and Golay codes. Preferably, a Hamming Code scheme is used. While the Hamming Code scheme is sometimes maligned as being outdated and underpowered, the implementation in certain embodiments of the present invention provides considerable robustness and extremely low computation and power burden for the error correction mechanism. FEC alone is sufficient to ensure that the vast majority of the data is transferred correctly across the radio link. Certain parts of the packet must be received correctly for the receiver to even begin accepting the packet, and the error correction mechanism in the remote communication station reports various signal quality parameters including the number of bit errors which are being corrected, so suspicious data packets can be readily identified and removed from the data stream.

Preferably, at a second, optional level, an additional line of defense is provided by residual error detection through the use of a cyclic redundancy check (CRC). The algorithm for this error detection is similar to that used for many years in disk drives, tape drives, and even deep-space communications, and is implemented by highly optimized firmware within the electrode patch processing circuitry. During transmission, the CRC is first applied to a data packet, and then the FEC data is added covering the data packet and CRC as well. During reception, the FEC data is first used to apply corrections to the data and/or CRC as needed, and the CRC is checked against the message. If no errors occurred, or the FEC mechanism was able to properly correct such errors as did occur, the CRC will check correctly against the message and the data will be accepted. If the data contains residual errors (which can only occur if the FEC mechanism was overwhelmed by the number of errors), the CRC will not match the packet and the data will be rejected. Because the radio link in this implementation is strictly one-way, rejected data is simply lost and there is no possibility of retransmission.

More preferably, the RF link utilizes a two-way (bi-directional) data transmission. By using a two-way data transmission the data safety is significantly increased. By transmitting redundant information in the data emitted by the electrodes, the remote communication station is capable of recognizing errors and request a renewed transmission of the data. In the presence of excessive transmission problems such as, for example transmission over excessively great distances, or due to obstacles absorbing the signals, the remote communication station is capable of controlling the data transmission, or to manipulate on its own the data. With control of data transmission it is also possible to control or re-set the parameters of the system, e.g., changing the transmission channel. This would be applicable for example if the signal transmitted is superimposed by other sources of interference then by changing the channel the remote communication station could secure a flawless and interference free transmission. Another example would be if the signal transmitted is too weak, the remote communication station can transmit a command to increase its transmitting power. Still another example would be the remote communication station to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements. This also reduces the energy requirements, thereby providing longer battery life. Another advantage of a two-way, bi-directional digital data transmission lies in the possibility of transmitting test codes in order to filter out external interferences such as, for example, refraction or scatter from the transmission current. In this way, it is possible to reconstruct falsely transmitted data.

Preferably, the step of measuring the subject's movement is performed substantially continuously. By substantially continuously, it is meant that preferably, while the subject is wearing the portable measurement and quantification device, the device and its sensors effectively monitor the subject's movement constantly as opposed to taking intermittent or periodic measurements, and as opposed to only measuring during a particular task or function. This substantially continuous measurement effectively means to support real-time discreet movement measurement while the subject goes about performing activities of daily living rather than being a clinical device for measurement of measurement at predetermined times, during predetermined activities or tasks designed for clinical purposes. Instead, the portable measurement and quantification device of the present invention is intended to be a measurement and quantification, and preferably a therapy, training and improvement tool constantly monitoring the subject's movement to detect pain substantially as it occurs. Real-time for purposes of movement measurement is meant to fit within the preferred ranges and constraints defined above. With respect to substantially continuous measurement of the subject's movement, it is meant that preferably the sensor(s) of the portable measurement and quantification device acquire movement data once every 60 seconds. More preferably the sensor(s) of the portable measurement and quantification device acquire movement data once every 30 seconds. Still more preferably the sensor(s) of the portable measurement and quantification device acquire movement data once every 10 seconds. Even more preferably the sensor(s) of the portable measurement and quantification device acquire movement data once every second. Still yet more preferably the sensor(s) of the portable measurement and quantification device acquire movement data once every 0.5 seconds. Even still more preferably the sensor(s) of the portable measurement and quantification device acquire movement data once every 100 milliseconds. Yet even more preferably the sensor(s) of the portable measurement and quantification device acquire movement data once every 50 milliseconds. Even yet more preferably the sensor(s) of the portable measurement and quantification device acquire movement data once every millisecond. Most preferably the sensor(s) of the portable measurement and quantification device acquire movement data at intervals less than 1 nanosecond. Such continuous measurement intervals may, in some embodiments, also include not only acquisition and measurement of movement data but also transmission of the signal from the sensor(s) to the electronics of the portable measurement and quantification device.

Many embodiments of the present invention include a step of providing some variety of treatment or therapy to the subject to help alleviate, prevent or otherwise address the disorders and/or symptoms he or she is experiencing. The treatment or therapy provided can be of any type using the treatment or therapy devices or tools described herein, or those known in the art. Examples of providing treatment or therapy to the subject include providing deep brain stimulation (DBS) to the subject using a DBS device or system, providing transcranial direct current stimulation (tDCS) using a tDCS device or system, providing pharmaceutical, drug or medication treatment to the subject by either instructing or prescribing a drug or medication to the subject or using a drug or medication titration and/or delivery system, or by providing instructions or guidance on particular movements, exercises, stretches, motions, posture, dietary or activity changes or recommendations, or other similar guidance to the subject on how to correct or address some aspect of his or her movement or body in order to address the cause of the disorders and/or symptoms. Such instructions or guidance may be provided to the subject visually, such as on a visual display of the portable measurement and quantification device, or any other visual display, or audibly via speakers or headphones of any variety that project audible commands or instructions to the user. The visual instructions or guidance can take the form of text, video, animation, or any other such form of portraying instructions for the subject to perform.

The particular type or variety of treatment or therapy depends on the particular embodiment of the present invention. Regardless of the type or variety of treatment or therapy being utilized, various embodiments of the present invention employ an iterative step of providing the treatment or therapy in order to attempt to reduce or eliminate the subject's disorders and/or symptoms. Whether the treatment or therapy is effective in reducing or eliminating the subject's pain is preferably measured and determined by subsequent or successive measurements and quantifications of the subject's disorders and/or symptoms using the portable measurement and quantification device. Essentially, whether the sensor measurement is periodic or continuous, when an initial pain measurement and quantification leads to a determination that treatment or therapy is required, the treatment or therapy is applied, and a successive disorders and/or symptoms quantification is measured and provided. The difference between successive quantifications of the subject's disorders and/or symptoms allows the system to determine whether the applied treatment or therapy is effective in reducing or eliminating the subject's disorders and/or symptoms. The determination then allows the system to determine whether new or additional treatment or therapy, a reduction or cessation of the applied treatment or therapy, or maintaining the same level and variety of treatment or therapy is required or likely to be beneficial to the subject.

Some embodiments of the present invention allow for the user or subject to input personal data into the device for use in the analysis or for cataloguing and notation purposes. Examples of personal data the subject may be able to enter include perceived or experienced symptom(s), experiences, observations or opinions of events that occur during the monitoring period, habits or usual activities the subject tends to perform, activities or tasks performed, and limitations, hindrances, pain or other impairments experienced during such activities or tasks. Additionally, the subject may be able to input personal symptom data directly related to the subject's perceived level of symptoms. The subject's perceived symptom level can be input according to any scale chosen and set into the device. The subject may be able to enter such symptom information freely on an ad hoc basis, or may be prompted to do so at various intervals or periods, or during certain events such as beginning and ending of the monitoring period. If the system prompts the subject for personal symptom level or severity input, it may be done in any manner sufficient to guide the user to select an appropriate level on the chosen scale, such as in a manner similar to the subject being presented rating scale and asked to select the value that most closely represents the perceived level of symptom (e.g., similar to a patient selecting the face on a Wong-Baker pain scale). Preferably, the system requires a higher level of inquiry into the subject's perceived disorders and/or symptoms level, and utilizes more in depth information relating to how the level of disorders and/or symptoms is affecting or has affected the subject's ability to perform certain tasks or activities, effectively going beyond merely the amount of perceived symptom and analyzing the level of disability due to disorders and/or symptoms.

In order to allow the user to input such personal data, the system preferably includes an input device. The input device can be a separate, standalone unit or device that transmits data and information to the system, such as a computer or tablet in communication with the subject-worn system. More preferably, however, the input device is integrated into or otherwise part of the system, such as the processor or processing device, for example the GUI described above. As noted above the processing device may be part of a computer or tablet, but such processors are not as readily portable for use while the subject is out performing activities, particularly in community involvement scenarios. In a preferred embodiment, the processor and input device are part of a smartphone or similar device with an accompanying application designed for the purposes of the present invention to receive input from the subject, clinician and sensors, analyze the data, and provide and output results of the monitoring and analysis. As such, the subject can utilize the input modalities (GUI) of the smartphone or similar device, such as physical keyboard, on-screen keyboard, microphone, camera and video camera in order to input any information required or desired.

Many embodiments of the present invention further include a step of calculating various quantified disorders and/or symptoms levels. This step is preferably performed by an algorithm specifically designed and optimized to account for the unique and numerous metrics and inputs of the system of the present invention in order to provide an accurate and object value for the quantity of disorders and/or symptoms severity or level the subject is experiencing. The algorithm is designed to gather all subject data—either objectively measured by the device or system or subjectively input from the user or clinician—and to coordinate, weigh, and integrate all sources of data in order to calculate an objective disorders and/or symptoms quantification value. The algorithm calculates and produces a quantification of the symptoms that represents the subject's level of disorders and/or symptoms or the disorders and/or symptoms intensity, preferably in the form of an index or score as disclosed above Based on the particular clinician and/or subject, the objective disorders and/or symptoms severity scale used to calculate and analyze the subject's disorders and/or symptoms can be different depending on the particular circumstances. The disorders and/or symptoms severity scale used can be of any variety that can demonstrate varying levels or intensities of disorders and/or symptoms, and different scales may be used for different disorders and/or symptoms. For example, the scale may be numeric and use whole numbers or positive integers from 0-100, fractional or rational numbers from 0-10 (on any incremental scale in between such as quarter, half or tenth numbers for example), or any other numbering system the clinician or device programmer may choose. The scale may also be shade- or color-based with various symptom quantifications being represented on a grey-scale (from white to black) or in color (e.g., shades of green to shades of red) to show the intensity, or in different patterns (e.g., cross-hatched, lined, dotted). The quantified symptom severity or level value or indication, in whatever form, is preferably output or presented to the user via the output device of the portable symptom measurement and quantification device. Optionally, and in addition or alternatively, the quantified symptom value may be transmitted and/or output for a clinician to see and analyze the subject's symptoms, and any treatment or therapy being applied.

The quantified symptom level or severity can be displayed in a manner that shows the subject's response to various treatment or therapy modalities and/or to various treatment or therapy variables or parameters. A map, or disorder and/or symptom response or severity map, is a two-dimensional representation of a three-dimensional set of data wherein the system can present the subject's quantified symptom severity or level as a function of many variables or factors. For example, items or labels along the vertical axis may represent different treatment or therapy types or modalities (e.g., drug delivery, DBS therapy, and tDCS), or may represent different settings or levels of a particular type of therapy or treatment (e.g., different drug or medication doses of the same drug, different drugs or medications, different exercises or stretches, different DBS amplitudes). Similarly, for example, items or labels along the horizontal axis may represent different variables of the treatment or therapy or groupings thereof, such as several groups of DBS parameters where each group has at least one parameter or variable that is different from the other groups, such as the selected stimulation contact, waveform, duration, or the like. Therefore, when treatment or therapy is applied according to the variables or factors indicated on the vertical and horizontal axes, the system can measure and quantify the level or severity of disorders and/or symptoms the subject experiences in light of the treatment or therapy, and populates the point of intersection with the quantified disorder and/or symptom level or severity. Such a map allows the user, and more importantly a clinician, to see exactly which treatment or therapy and the settings, parameters or variables are the most effective in alleviating the subject's disorders and/or symptoms. This map system allows for tailored and targeted treatment or therapy based on objective, quantitative data rather than merely relying on observation of the subject or the subject's self-reported level or severity of disorders and/or symptoms.

Another step in many method embodiments of the present invention is determining whether the treatment or therapy needs to be changed, adjusted, or altered in any way. By performing the iterative measurement and quantification of symptoms as described above, the system can populate the map, or disorder and/or symptom response or severity map, in order to show the subject's response to various forms and variables of treatment or therapy. This not only provides the clinician or system with a desired or optimal or most effective treatment or therapy plan, but it also clearly demonstrates the treatment or therapy that is almost as effective as the optimal combination. Therefore, when the subject is receiving a prescribed treatment or therapy and the system measures and quantifies an increased level or intensity of disorders and/or symptoms, or simply a quantified level or intensity of disorders and/or symptoms that is not expected based on the applied treatment or therapy, the system or a clinician can then determine that the treatment or therapy is not presently effective, and that the treatment or therapy needs to be changed, adjusted, or otherwise altered. The benefit of the disorder and/or symptom response or severity map is that set of "next best" treatment or therapy alternatives is known and available and allows the system to intelligently select the next treatment or therapy, and the parameters thereof, to apply. This significantly reduces the amount of time the subject likely has to suffer from the increased or altered disorders and/or symptoms and allows the system to rapidly adapt to the subject's changed disorder and/or symptom conditions.

A primary benefit of the present invention involves the ability to provide precision dosing of medication or drug treatments or therapies to the subject. By precision dosing it is mean that the systems and methods of the present invention can recommend and/or provide smaller doses of drugs or medications at precise and specific times to most accurately and effectively treat the subject's disorders and/or symptoms. Precision dosing allows the system to provide the drug or medication, or to instruct the a clinician or the subject to administer or take the drug or medication, precisely when needed to prevent the onset or return of disorders and/or symptoms, or to treat such disorders and/or symptoms at the optimal time in order to mitigate the effects thereof and or the intensity or severity thereof. Smaller doses of drugs and medication is highly beneficial for preventing overdose, dependency, and tolerance to the drug or medication. The precision dosing function of the present invention effectively provides a smaller dose of a drug or medication to the subject, or instructs a user to administer or take a smaller dose, precisely when needed based on the various metrics or measurements of the system, and thus the drugs or medications are only provided when needed, and in smaller amounts thereby increasing the effectiveness of the treatment while minimizing the cost of the treatment by potentially reducing the cost of the medication and number of refills, while also optimizing the efficacy of the drug in the subject's system as it relates to treating his or her disorders and/or symptoms. The step of providing precision dosing creates a desired or optimal drug or medication profile in the subject's bloodstream in order to provide the maximum effect and benefit to the subject in treating their disorders and/or symptoms while reducing the chance of building a tolerance or overdosing. Maintaining the desired or optimal concentration of the drug or medication in the subject's bloodstream reduces the highs and lows associated with normal drug or medication dosing and maintains the desired or optimal level for controlling the subject's disorders and/or symptoms without the oscillations that normally occur when taking a drug or medication simply based on an instructed time frame. When referring to a desired or optimal drug profile, preferably the profile is maintained within the drugs intended uses and indications of use. Also preferably, the desired or optimal drug profile takes into account the particular physiological and demographic condition and status of the subject. Different subjects metabolize drugs differently. It is therefore preferable that a subject's desired or optimal drug profile takes into account the particular subject's past experience with a particular drug, or such experience of other subject's that are as similar to the instant subject as possible. Preferably, over a period of time, the subject's symptoms and treatments are tracked—either clinically (e.g., by a physician, clinician, or technician), or personally by the subject (e.g., personal diary or recording of dosing and symptoms via the present invention's systems or other such recordation systems). Preferably at least the drug, drug dose, timing of dosages, symptoms, symptom severity, and timing of symptoms are tracked and/or otherwise recorded for the subject. Additional information that may be recorded may include the subject's activities, habits, environment, and other such conditions which were present and thus might affect the drug's efficacy and metabolization. Such information is preferably saved, digitized, and stored for later reference, and ay preferably be stored in a central or cloud database as described herein. With this information it is possible to predict the particular subject's metabolization of the drug under given circumstances, and a subject-based profile of the drug's activity can be formulated which predicts when the drug will take effect, how long it will last, when the subject's symptoms might be expected to begin to recur, how severe the symptoms will be during off times (times when the drug is having diminishing effect or is out of the subject's system), and the like. Thus, preferably, the system can provide a customized, precision prediction within the drug's intended uses and indications of use to provide a desired or optimal drug profile in the subject's bloodstream based on the predicted activity of the drug in the subject's system. Further preferably, the desired or optimal drug profile is maintained within ±75% of the preferred or recommended blood concentration or a desired threshold value. More preferably, the desired or optimal drug profile is maintained within ±60% of the preferred or recommended blood concentration or a desired threshold value. Still more preferably, the desired or optimal drug profile is maintained within ±50% of the preferred or recommended blood concentration or a desired threshold value. Yet more preferably, the desired or optimal drug profile is maintained within ±35% of the preferred or recommended blood concentration or a desired threshold value. Even more preferably, the desired or optimal drug profile is maintained within ±25% of the preferred or recommended blood concentration or a desired threshold value. Still yet more preferably, the desired or optimal drug profile is maintained within ±15% of the preferred or recommended blood concentration or a desired threshold value. Yet even more preferably, the desired or optimal drug profile is maintained within ±10% of the preferred or recommended blood concentration or a desired threshold value. Even still more preferably, the desired or optimal drug profile is maintained within ±7% of the preferred or recommended blood concentration or a desired threshold value. Yet still more preferably, the desired or optimal drug profile is maintained within ±5% of the preferred or recommended blood concentration or a desired threshold value. Still even more preferably, the desired or optimal drug profile is maintained within ±3% of the preferred or recommended blood concentration or a desired threshold value. Even yet more preferably, the desired or optimal drug profile is maintained within ±1% of the preferred or recommended blood concentration or a desired threshold value. Many embodiments are adapted to provided automated or semi-automated notification to a clinician, physician, or technician if the recommended drug regimen or protocol fails to maintain the desired or optimal blood profile of the drug. Such determination would be made based at least in part on the quantified severity of the subject's disorder's and/or symptoms and/or side effects. If the drug regimen or protocol is administered, and the subject's disorders, symptoms, and/or side effects are too severe compared to what would be expected from the regiment or protocol, then the system may transmit a message to the clinician, physician, or technician of the discrepancy, and the clinician, physician, or technician can then take appropriate measures to alter the subject's recommended drug regimen or protocol. Such alterations may include prescribing a new drug, altering the dose of a drug, suggesting combinations of drugs and/or action recommendations, and providing proper instructions to the subject and/or into a device for administration of the new regimen or protocol. The subject and/or the system may then provide notification to the clinician, physician, or technician when the new regimen or protocol has begun to be administered so that the quantification results can be evaluated based on the new regimen or protocol.

The precision dosing step further enables the unexpected benefit of being particularly effective and useful for drugs or medications that exhibit a shorter time release profile and having a more immediate effect (e.g., drugs that are fastacting by being quickly metabolized, but that are typically depleted or used faster requiring more frequent doses). Such compounds are more easily controlled and administered using the precision dosing steps of the present invention. Preferably, the precision dosing step may be used for drugs or medications that have an effective life in the subject's bloodstream of 8 hours or less. More preferably, precision dosing may be used for drugs with an effective life in the subject's bloodstream of 8 hours or less. Still more preferably, precision dosing may be used for drugs with an effective life in the subject's bloodstream of 6 hours or less. Yet more preferably, precision dosing may be used for drugs with an effective life in the subject's bloodstream of 5 hours or less. Even more preferably, precision dosing may be used for drugs with an effective life in the subject's bloodstream of 4 hours or less. Still yet more preferably, precision dosing may be used for drugs with an effective life in the subject's bloodstream of 3 hours or less. Yet even more preferably, precision dosing may be used for drugs with an effective life in the subject's bloodstream of 2 hours or less. Even still more preferably, precision dosing may be used for drugs with an effective life in the subject's bloodstream of 1 hour or less. Thus, the precision dosing of the present invention enables the use of drugs or medications that normally would not be considered due to the difficulty in maintaining compliance with their administration. Precision dosing inures this benefit to self-administered drugs and medications as well as those delivered by drug pump systems (semi-closed loop or closed loop).

Another step in many method embodiments of the present invention is that of outputting the determination(s) of the algorithms for use by the subject, a clinician, or another device. The determinations may be one or more of those discussed herein, including data for storage and/or review, a quantified disorder and/or symptom index or score, a visual disorder and/or symptom response or severity map, various warnings or messages, commands or controls for other systems or devices such as treatment or therapy devices, or recommended treatment protocols or regimens or protocols such as recommended drugs, drug doses, and timing. The step of outputting the determination, then, depends on the particular embodiment. Data for storage and/or review is preferably output by transmitting the data to device or remote location intended for storage of the data and for retrieval by the subject or a clinician when necessary or desired for review, such as a database as disclosed herein. Quantified disorder and/or symptom indices or scores are preferably output both to a display device (e.g., GUI of subject's device(s), remote computer, phone, tablet, or other display for physician, clinician, or technician) and stored over time. The disorder and/or symptom index display allows the subject or clinician to see the estimated level or severity of disorders and/or symptoms on a real-time basis, either through a continuous display or on demand (e.g., the system utilizes a smartphone for continuous monitoring and the user can turn on the smartphone display to see the disorder and/or symptom index). The disorder and/or symptom index or score could also be output audibly such as by an auditory recitation of the actual index or score value, or by any variety of audible sound to indicate that the index or score has changed or perhaps reached some threshold related to a disorder and/or symptom level or severity of interest to the subject or a clinician. Similarly, the disorder and/or symptom response or severity map may be output to any visual display device such as the integrated or connected processor device (e.g., smartphone) or may be transmitted to a separate and/or remote display device such as a computer or tablet. By the very nature of the information displayed in the disorder and/or symptom response or severity map, the most preferable output of the map is to a device where the clinician can review and analyze the subject's disorder and/or symptom response and determine an appropriate course of action, treatment or therapy to help reduce, mitigate and alleviate the subject's disorders and/or symptoms. Warnings or messages can be output visually (e.g., flashing lights or screens, changing colors, text messages across a visual display, or the like), audibly (e.g., audible tones, notes or tunes akin to notifications from a cellular phone, spoken messages, or the like), through tactile notifications (e.g., vibration), or any other method of alerting or notifying the subject or clinician of a condition or event requiring attention. The system further can output commands or controls for other devices such as treatment or therapy devices, particularly where for systems utilizing semi-closed-loop or closed-loop control. In these embodiments, the system may output recommended treatment parameters or protocols and allow the subject, or more preferably, a clinician to review, edit and/or approve the parameters or protocols so that the treatment or therapy device may administer the treatment or therapy to the subject. Such output may include a disorder and/or symptom response or severity map as well as recommended parameters, but may just include treatment parameters while allowing for the option to selectively view actual measurement data to confirm that the recommended settings are acceptable or need to be edited. Alternatively, particularly in closed-loop systems, the processor device may directly transmit treatment or therapy parameters or settings to the treatment or therapy device such that the parameters or settings are programmed into the treatment or therapy device such that the device then operates to provide treatment or therapy to the subject based on the newly programmed parameters or protocol. Similarly, the output may be in the form of a recommended drug or medication regimen or protocol comprising the recommended drug, drug dosage, and/or instructions and timing for taking said drug. The recommended drug regimen or protocol is preferably displayed visually for the subject, such as on the GUI of the subject's device(s), may be audibly presented by reciting the regimen or protocol to the subject, and is also preferably sent in print form to the subject, such as by email or made available through the app where the subject may access the regimen or protocol on-demand at any time he or she wants to review the regimen or protocol.

The semi-closed-loop or closed-loop treatment or therapy embodiments of the present invention can either utilize the local processor device or a remote processor device to suggest and provide recommended or automated treatment or therapy parameters or protocols. In such embodiments, at least one electronic component for transmitting and receiving signals is required. The subject-worn monitoring device needs to have at least one electronic component for transmitting signals and data, particularly programming commands comprising treatment or therapy protocols, and the treatment or therapy device must have at least one electronic component for receiving such signals and data. In such embodiments, data corresponding to the subject's measured and calculated metrics and measures and resulting symptom analysis data may be collected by the subject-worn monitoring device and transmitted using the at least one electronic component for transmitting signals either directly to the treatment or therapy device (closed-loop systems) or to a remote location or remote locations for review and analysis by a clinician, physician or technician (semi-closed-loop or open-loop systems). The data may be transmitted to a clinical center or location where a clinician, physician or technician can view the data. In such embodiments, the clinician, physician or technician can then make a decision and determination regarding a level of treatment or therapy parameters or settings that should be applied to the subject's therapy device. Alternatively or in addition, an algorithm may be used to provide the determination as to the level of therapy parameters to be applied to the subject's therapy device, and a clinician, physician or technician may optionally review the settings determined by the algorithm. In some embodiments utilizing remote adjustment of therapy or treatment, once a determination as to level of treatment or therapy parameters or settings is made, this level of parameters or settings is then transmitted back to the subject's therapy device where it is received by at least on electronic component for receiving signals. In still other remote embodiments the subject-worn monitoring device may provide a suggested or determined level of therapy parameters, and in such embodiments the movement data and/or such suggested or determined treatment or therapy parameters or settings may be transmitted to the treatment or therapy device to automatically program the treatment or therapy device to operate according to the parameters or settings. Additionally, the movement data and/or level of treatment or therapy parameters or settings may additionally be transmitted to a remote location for review and/or storage, and/or a central server, cloud based server, or other such database for storage and backup purposes.

Once suggested treatment or therapy parameter or setting adjustments are computed by the treatment or therapy computation algorithm(s), the adjustments or new parameters or settings may optionally be displayed on a display or user interface of a local or remote processing device or system (e.g., GUI of the subject's device(s)). A treatment or therapy algorithm of the processor or processing device then computes suggested therapy device parameters or settings based at least in part collected movement data comprising the measured or calculated metrics or measures and/or the resulting output of the system regarding symptom severity or level quantification, for example quantified symptom index or the disorder and/or symptom response or severity map produced from the measures or metrics. Other input that may necessarily be included in the determination of therapy or treatment parameters or settings includes previously set treatment or therapy parameters that have been applied to the subject. This is particularly relevant for embodiments utilizing the disorder and/or symptom response or severity map which may include as an input current therapy or treatment parameters or settings and which then tracks the subject's symptom response to those parameters or settings and attempts to offer new parameters or settings that better alleviate the subject's symptoms. In many embodiments, the various algorithms utilized are able to analyze the measured and quantified movement and symptom data in correlation to the therapy parameters or settings being provided, determine if those parameters or settings are adequately addressing the subject's needs, and be able to adjust the parameters or settings to better address the subject's needs. In such embodiments, the algorithm would then know to avoid the parameters or setting that are likely to not adequately address the subject's symptoms, and thus avoid including them in the provided set or group of parameters and settings. Much like the scoring and mapping algorithms disclosed above, in some embodiments, the therapy algorithm(s) may take the form of artificial intelligence that is adapted to combine data and/or movement and/or symptom measurements to create a treatment or therapy regimen or protocol that is more precisely directed to the instant subject's particular state. Preferably, such artificial intelligence (AI) algorithms may compare, contrast, and/or correlate the instant subject's measured data with a plurality of data, such as in a database, comprising historical data from the instant patient, a plurality of other patients with similar disorders and/or symptoms, or a combination thereof. Historical data preferably includes a combination of relevant patient characteristics, treatment parameters, and results. More specifically, the historical data may include patient demographic and physiological or physical information such as age, weight, race, gender, ethnicity, activity levels (e.g., very active, moderately active, sedentary, etc.). Also preferably, the historical data includes information on each subject's diseases, disorders, and/or injuries, symptoms thereof, scores, indexes or other quantifications of the disorders and/or symptoms, duration and length of time suffering from or experiencing such disorders and/or symptoms, and the like. Further, the historical data preferably includes data related to any treatments or therapies (e.g., electrical stimulation such as DBS, FES, spinal cord stimulation, or the like; medications or drugs the subject has used, both prescription and over the counter (OTC), as well as the delivery mechanism for such drugs, such as implanted closed-loop or semi-closed loop drug pumps, injections, transdermal patches, oral medications such as liquids, pills, tablets, and the like, as well as the doses and instructions for taking the medications or drugs such as timing between doses, time of day, with or without meals, with or without other drugs or medications either prescription or OTC, and the like) the subject has been prescribed or otherwise tried and the results of those treatments or therapies. Preferably, the results of the treatments or therapies include the effects that such treatments or therapies had on the subject's disorders and/or symptoms quantitatively (e.g., indexes or scores representing the severity or level of the disorders and/or symptoms when on and/or off of the treatment or therapy, length of time between recurrences of disorders and/or symptoms, duration of the occurrence of disorders and/or symptoms, and the like) and/or qualitatively (e.g., subjective data representing the subject's thoughts, feelings, impressions, ratings of his or her disorders and/or symptoms (including subjectively quantitative scores or indexes), and other subject-diary entries including activity tracker data, diet tracker data, mood inputs, and the like. This AI correlation process preferably utilizes the historical information to more accurately and precisely guide the determination of the instant subject's disorder and/or symptom severity by using the plurality of historical data to narrow down the results and base the analysis on those data points that are most similar or related to those of the instant subject. The AI algorithms take into account all available data in determining the data points that are most relevant and applicable to the instant subject's current status and condition, and thus informs its calculations based on the data that is most likely to yield positive results for the instant subject. The result of the therapy algorithm(s)' calculations is to produce a set of recommended treatment or therapies, or treatment or therapy parameters, settings or instructions, specifically tailored to the instant subject's needs. The recommended treatment or therapy, or treatment or therapy parameters, settings, or instructions (collectively or individually "recommended therapy") may be of any type disclosed herein including, but not limited to, drug, drug dose, and/or instructions for taking or otherwise self-administering a medication or drug therapy (e.g., oral medications such as liquids, pills, tablets, or the like, self-administering injectable drugs or medications, applying transdermal patches for drug or medication delivery, etc.), parameters or settings for semi-automated or automated (semi-closed loop or closed-loop) delivery of drugs or medications such as via external or implantable drug delivery pumps, and/or stimulation parameters or settings (such as for DBS devices, FES devices, spinal cord stimulation devices, and the like). Additionally, the therapy regimen or protocol may include personal suggestions for the subject directed to the subject's lifestyle, activities and habits in order to improve his or her condition and mitigate his or her disorders and/or symptoms. Such lifestyle treatment recommendations may include dietary suggestions or changes (e.g., recommended foods to eat or avoid, vitamins/supplements to take, real-time suggestions that the subject should eat within a given time period, and the like) and activity suggestions or changes (e.g., exercise or training recommendations such as intensity level, specific exercises or activities to perform, frequency of activity; sleep habit suggestions including duration, position, and supplements to aid sleep; activities, positions, movements to avoid; and the like). The therapy algorithm may optionally employ any one, or a combination of, mathematical models currently known to those in the art, including, but not limited to linear and non-linear classification methods such as logistic regression, artificial neural networks, k-means clustering, genetic algorithms, and the like in order to analyze and process the various metrics or measures and translate them into a recommended treatment or therapy regimen or protocol. Preferably, an artificial neural network, genetic algorithm, or other such advanced type of algorithm is used when correlating with a database in order to provide rapid and robust optimization and AI functionality in calculating the recommended treatment or therapy regimen or protocol.

Referring to the drawings, FIG. 1 presents a pictorial overview of one embodiment of the system of the present invention in use by a subject. The particular embodiment depicted utilizes motion sensors 105, other sensors related to physiological characteristics affected by the subject's disorders and/or symptoms (not shown), GPS 120, and a smart phone 115 application (i.e., "app") 125 to monitor physical activity, location, and self-reported information on symptom severity or level and QOL. The depicted embodiment of the smartphone app shows a user interface which allows the subject to enter or review data corresponding to the activities 130 he or she has performed or is performing, the symptoms 135 her or she exhibits in the measured movement which may contribute to or cause symptoms or other disability, and general settings 140 for the app and system. Whether the subject 100 is at rest 145 or performing some activity, movement or motion 150, the sensors 105 can be worn, attached to, or carried by the subject 100 to continuously acquire signals to monitor the subject's physiological status. The sensor(s) 105 are preferably small and wireless, though wired embodiments may be preferable for some applications. The sensors 105 may include motion or physiological sensors to measure and monitor the actual movement or condition of the subject 100, or environmental sensors, such as GPS 120, to determine the subject's location and overall activity. The sensors 105 preferably communicate 110 with the processing device, in this embodiment a smartphone 115 with an associated app 125, and the smartphone 115 and app 125 collect, process and analyze the data. The analyzed data can be organized and/or presented in many different ways, and can optionally be transmitted to a remote, secure location or server (not shown) for further analysis.

Figure 2A:
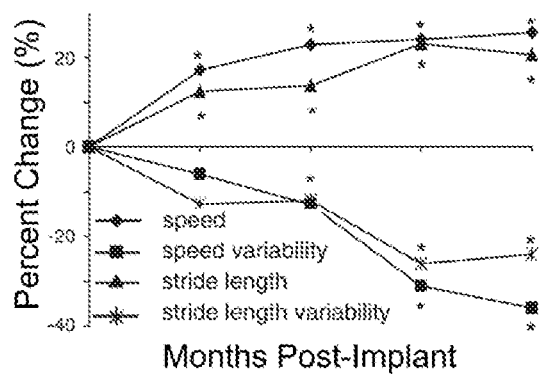
FIGS. 2A-C. Graphical depiction of various clinically observed or measured metrics or analytical data processing values in an experimental group, such metrics being able to be measured by the present invention objectively, such measures or analyses including: (A) percent change in pain intensity over time after treatment or therapy, (B) fractal exponent characterization of subject pain, and (C) heart rate variability measurements compared with therapy or treatment on or off.
Figure 2B:
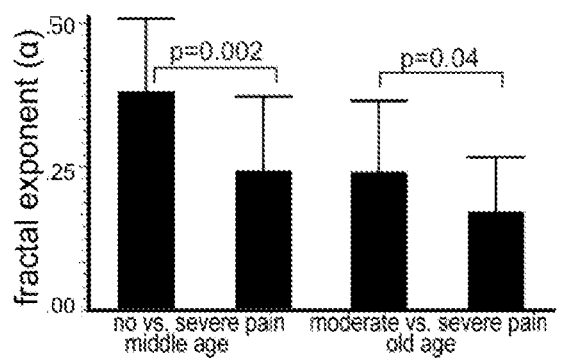
Figure 2C:
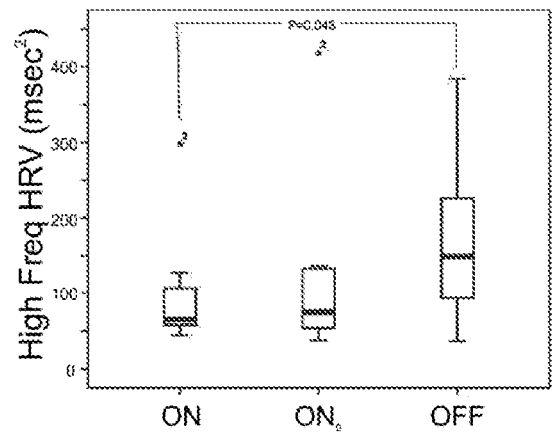

FIGS. 2A-C depict graphical trends of results for various metrics that show improvement over time in subject pain perception after implantation of an electrical impulse generator system, such as a spinal cord stimulation system. Specifically, the graphs show (A) percent change from baseline before implant to 12 months after SCS implant in self-rated pain intensity—a subjective grading value provided by the subject based on perceived pain, (B) a fractal exponent metric or measure used to characterize subtle differences in subject's with chronic pain as a result of the high degree of sensitivity of the sensors and system, and (C) a heart rate variability measure or metric of a subject. The motion-sensor measured metrics depicted are merely examples of metrics which can be used to objectively and accurately measure and monitor the subject's pain level in order to ensure that proper and optimal treatment and therapy is being provided to the subject. These graphs depict improvements of a subject over time as a result of treatment or therapy and monitoring of the subject's pain and the sensitivity of the various sensors and the system as a whole.

Figure 3A:
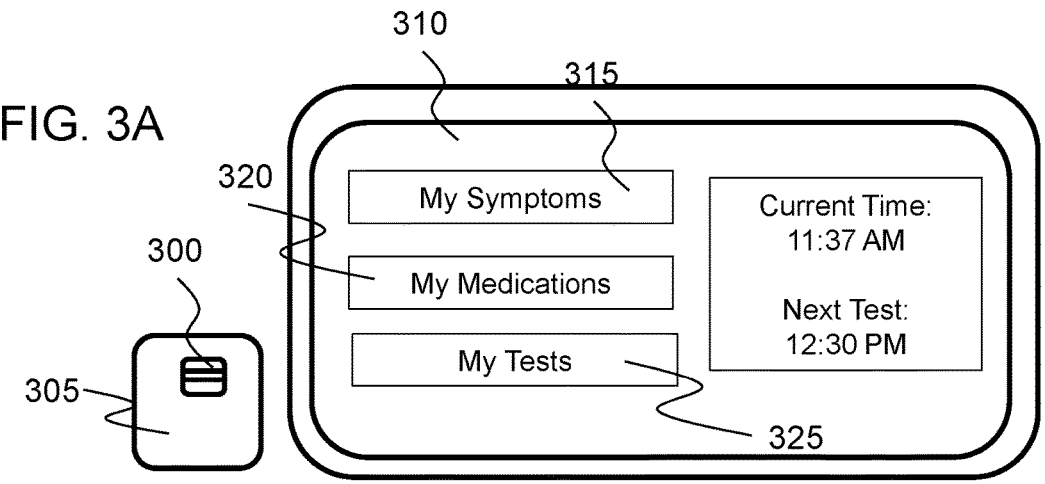
FIGS. 3A-B. Depiction of various components of the system and device of the present invention, including: (A) sensor unit and processing device, and (B) software/user interface and monitoring results.
Figure 3B:
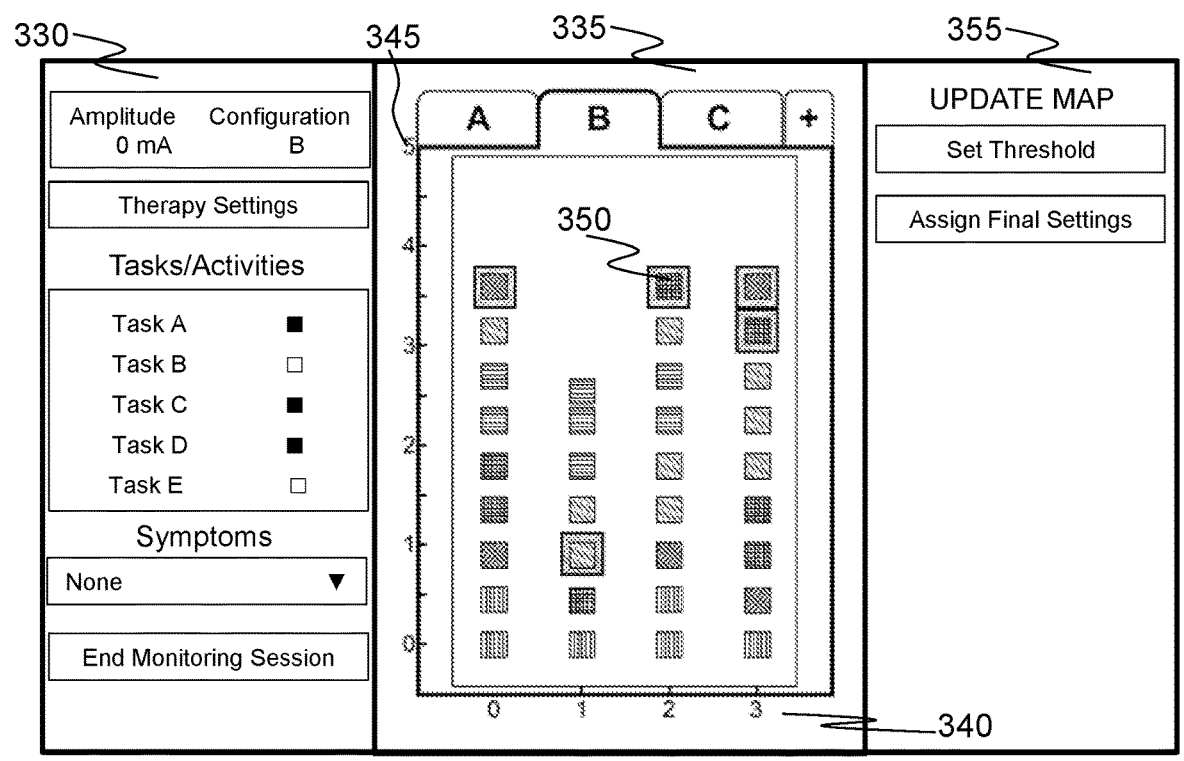

FIGS. 3A-B depict various aspects of the device or system of the present invention. FIG. 3A depicts an example of a subject-mountable sensor unit 300 on top of a charging pad 305 that can be used to charge the sensor unit's internal batteries via an induction charging process. The charging pad 305 may, in some embodiments, additionally provide a cue to initiate data transmission from the sensor device to a processing device and/or a remote location or server. Alternatively, such data transmission may be automatic and/or continuous. The system further includes a processing device 310, which is depicted as a tablet computer 310 in the present embodiment. However, the processing device can be any variety of devices capable of processing data and running associated software for proper data analysis. Examples of such devices may include tablet computers, laptop computers, desktop computers, personal digital assistants (PDAs), standalone specialty processing devices, smartphones, smart watches, and the like. The specific embodiment depicted in FIG. 3A includes a subject-mountable sensor unit 300 that contains three-axis accelerometers (not shown) and gyroscopes (not shown), and a Bluetooth radio (not shown). In some embodiment, instructional videos on a tablet 310 may guide subjects through a motor exam. All data is uploaded from the tablet 310 to a secure HIPAA compliant server (not shown). In the depicted embodiment, the tablet is displaying a user interface whereby the subject can interact with the app or software in order to input, review, or edit various sets of data including a list of symptoms 315 that the system has determined to be present from the various metrics and measures, a list of medications 320 the subject is taking that may affect the subject's movement or condition and thus the measurements of the system, and a list of tests 325 that the subject has performed or perhaps are in queue for the subject to perform.

FIG. 3B depicts one screen of an embodiment of the graphical user interface (GUI) through which a user (e.g., subject or clinician) interacts with the system and the data. The screen depicted in the present embodiment shows a set input windows 330 and 355 whereby the user can input data regarding the subject, activities or tests, therapy or treatment, and the like which will be used to populate the results of the monitoring. The screen further depicts a disorder and/or symptom response or severity map 335 which graphically depicts in a two-dimensional representation the results (i.e., quantified symptom level or severity measure) 350 based on various inputs or variables (axes of the graph) 340 and 345. The user can see the results 350 of the system's measurement and can interact with the data to change views, transmit the data, alter treatment or therapy protocols, or the like.

FIG. 4 depicts an alternative view from the disorder and/or symptom response or severity map in FIG. 3B in which actual sensor measurements 400, 405, 410 are presented in graphical form as measured over time. In the particular embodiment depicted, individual signals from each of the three axes of gyroscope measurements are shown. This represents merely one example of an alternative view the user can select for display depending on the particular sensors and measurements used for the given embodiment. For example, other embodiments may display substantially real time physiological sensor recordings such as EEG, EKG, or the like waveforms, accelerometer data, or any combination of sensor measurements the system obtains.

FIG. 5 presents a number of outcome measures that can be measured or derived by the system in order to analyze the subject's physiological status. The measures 505 can be broken down into several domains 500 in order to more accurately classify and explain what each measure 505 describes or correlates with physiologically. Certain measures 515 relate to physical activity 510, and may include: percentage of the day spent moving, relationship between activity and rest periods, percentage of day in different body postures, and the like. Other measures 525 relate to mobility and community participation 520 of the subject, including: leg swing velocity, stride variability, double limb support time, number and duration of trips and stops, percentage of time spent at and away from home, and the like. Measures such as number and duration of trips and stops and percentage of time spent at or away from home are measured by or extracted from GPS data rather than motion sensors or other sensors related to physiological characteristics affected by the subject's disorders and/or symptoms. Other measures 535 relate to sleep quality 530, including: amount of time spent asleep, number of times awoken, sleep efficiency, and the like. Speech domain 540 measures 545 may also be used, such as alternating motion rate.

Figure 6:
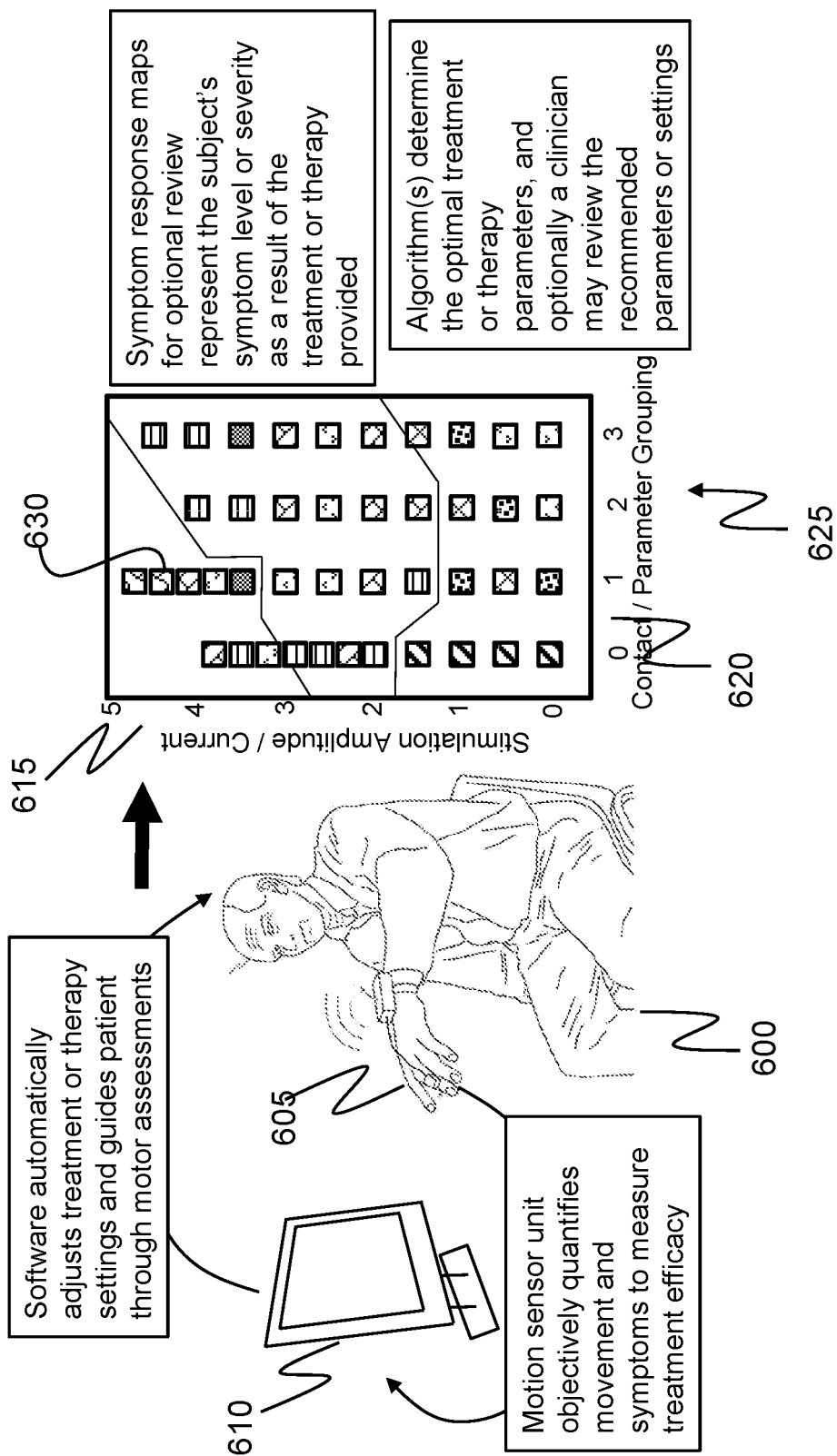
FIG. 6. Illustration of the monitoring process utilizing structured or instructed movement tasks for providing recommended treatment or therapy parameters or settings.

FIG. 6 depicts a method of the present invention utilizing an automated treatment or therapy system during guided testing. As the subject 600 performs tests, as instructed via a display 610 (automated), while wearing the subject-worn monitoring device 605, the system records and analyzes the results of those tests in light of the many variables. The system then populates a disorder and/or symptom response or severity map 625, in the background, to show the subject's response to the tested treatment or therapy parameters for each symptom while substantially simultaneously entering the same data into an algorithm(s) for quantifying the subject's level or severity of disorders and/or symptoms and optionally for recommending new treatment or therapy parameters or settings, or drug, drug dose, and/or instructions. The axes 615 and 620 of the disorder and/or symptom response or severity map 625 may represent a single test variable, or may represent a grouping of variables or therapy settings or parameters that are used while the subject 600 conducts a test(s). The disorder and/or symptom response or severity map 625 is populated by visual results 630 representing the severity of the subject's 600 symptoms or symptom severity level, or some other metric being measured, and the same data is entered into the algorithm(s). A clinician, technician or physician then determines, based on the test results, a set of treatment or therapy settings or parameters that are then entered into the subject's therapy device (not shown), or transmitted to the subject such as via the GUI of the subject's device(s). Alternatively, the system may utilize the disorder and/or symptom response or severity map 625 to suggest treatment or therapy parameters or settings to the clinician, physician or technician for review. The parameters or settings are preferably optimized to meet a number of criteria or constraints, including best managing and addressing the subject's needs for comfort and symptom alleviation, but also for maximizing performance of the system, for example through maximizing battery. The parameters are then entered into the subject's treatment or therapy device (not shown) for further testing or for delivering treatment and therapy to the subject.

Figure 7:
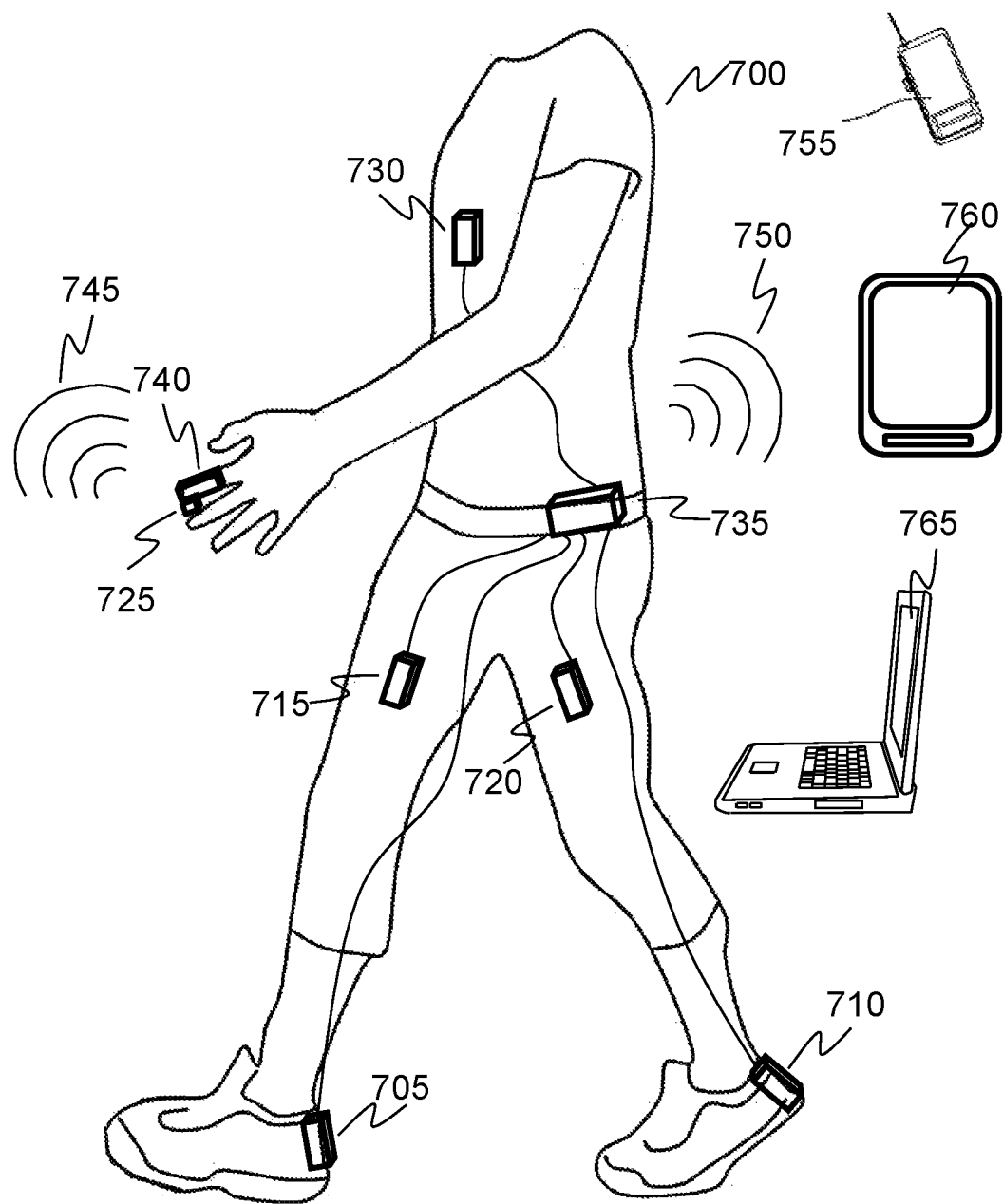
FIG. 7. Graphic depiction of a subject showing possible sensor and sensor unit placement options on multiple, separate parts of the subject's body either individually or simultaneously in multiple, separate locations for monitoring of the subject's movement and physiological status.

FIG. 7 illustrates possible sensor or sensor unit locations of a subject-worn monitoring or portable diagnostic/measurement and therapy systems or devices or system for different embodiments of the present invention for measuring or monitoring full body motion, or body motion from multiple, discrete body parts. The subject 700 in this particular embodiment is wearing six separate sensor units 705, 710, 715, 720, 725, 730 comprising accelerometers and gyroscopes (not shown) for recording movement data. The subject 700, in this embodiment, is depicted to be wearing at least one sensor unit on each foot 705, 710, thigh 715, 720, on one finger 725, and on the torso or trunk 730, though more sensors or sensor units may be placed in each, and/or other locations. Additionally, an optional, separate transceiver unit 735 for preprocessing and transmitting the movement data may be in wired (see connection to sensors/units on subject's heels, thighs and torso) or, more preferably, wireless communication 745 with wireless transmission components 740 one or more of the sensors (depicted only for the finger sensor 725, though optionally utilized for all sensors). The optional, separate transceiver unit 735 may further be in wired (not shown) or wireless 750 communication with the subject-worn monitoring device which may be a smartphone 755, tablet computer 760, laptop or other computer 765, or any other such device capable to be used as the portable diagnostic/measurement and therapy systems or devices. Alternatively, and preferably for some embodiments, no transceiver device may be present for local communication, and each of the sensors may be in direct communication with the processing device. The movement data from the optional, separate transceiver unit 735 or directly from the sensors is either stored for transfer at a later time or for immediate transmission to receiving circuitry or electronic components (not shown) on the portable diagnostic/measurement and therapy systems or devices via various mediums and any transmission protocols, for example, radio link, or by Bluetooth, WIFI, or even USB, or the like. The processor (not shown) of the portable diagnostic/measurement and therapy systems or devices 755, 760, or 765 feeds the data into a trained algorithm preferably loaded into the processor. The trained algorithm then uses the measured movement data to determine, detect or predict symptoms of various disabilities or disorders and to quantify the severity or level of disorders and/or symptoms the subject is suffering, and outputs the determination in the form of a quantified symptom index or score, disorder and/or symptom response or severity map data population, or parameters or settings for treatment or therapy either for clinician review or as input to control a treatment device such as an electric stimulator, automated medicine delivery or titration device, or the like.

Figure 8:
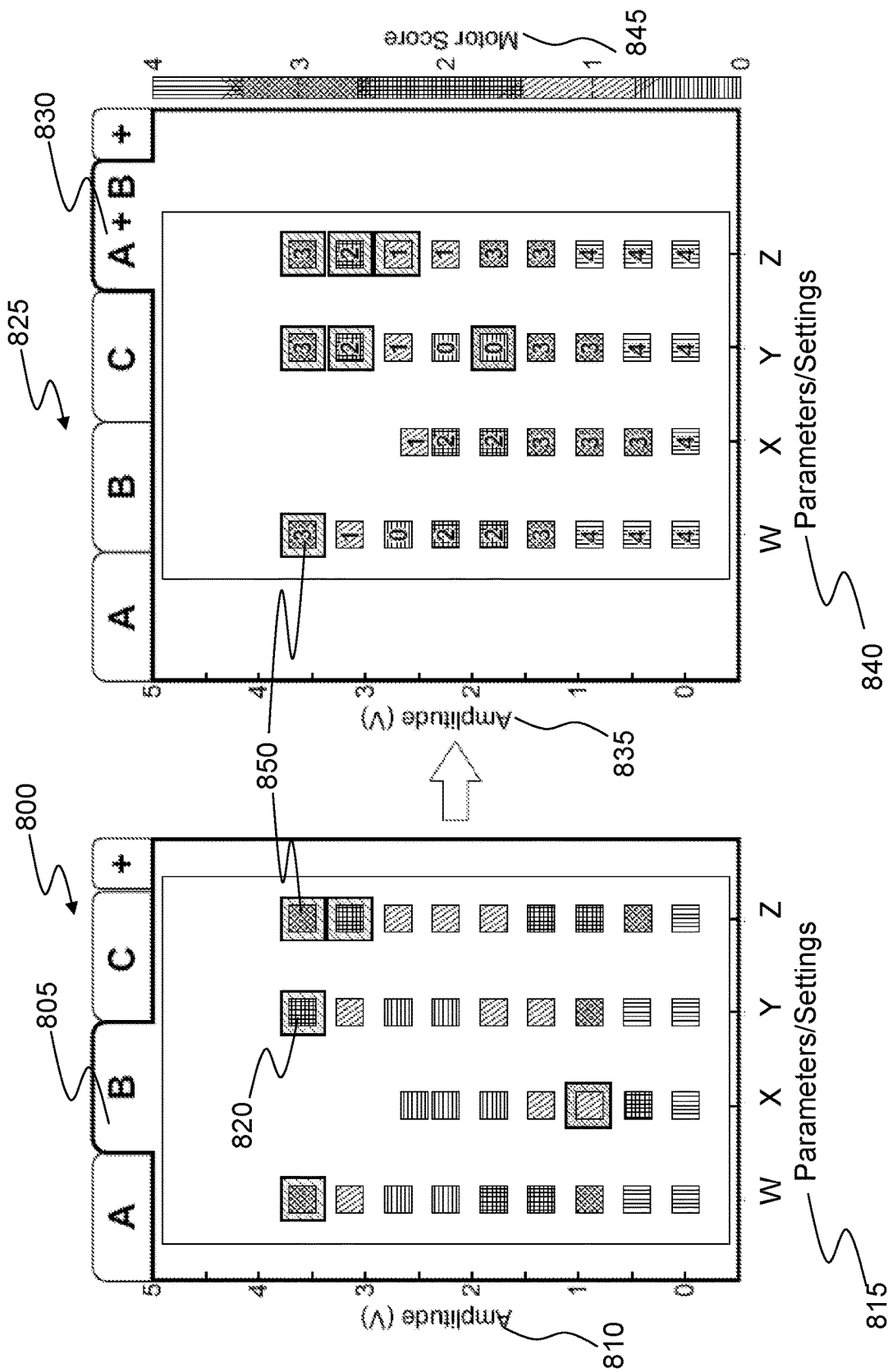
FIG. 8. Graphic depiction of one embodiment of pain response maps used to display test results and pain severity objectively measured by the system and displayed as a scatter plot of quantified pain severity scores.

FIG. 8 portrays one example of the disorder and/or symptom response or severity maps 800, 825 or other visual display tool or method for a particular embodiment with amplitude 810, 835 on the vertical axis and groupings of parameters or settings 815, 840 on the horizontal axis, in greater detail. Each task or test performed, activity or motion is represented by a separate tab 805 with its own disorder and/or symptom response or severity map 800, 825. Though the tabs 805 are labeled as A, B, C and A+B in the figure, in many preferred embodiments the tab 805 may be labeled with a number, the name of the task, test or activity it represents, an abbreviation thereof, or some other label indicating to the clinician, physician or technician what information is represented in the given tab 805. The amplitude 810, 835 is merely one example of a treatment or therapy parameter or setting (particularly for electrical stimulation devices) that can be used as a constant in monitoring the subject's symptom response, and is used here as only an example, and is not intended to be limiting. In this example, amplitude is tracked along one vertical axis of the map 800, 825 for each grouping of parameters or settings 815, 840 that are used as shown on the horizontal axis, while the severity of the symptom detected or measured or quantified disorder and/or symptom severity or level 845 are shown on the other vertical axis 845 and correlated to an indicator 820 (e.g., cross-hatching pattern, color, or the like) of each individual test result box 850. Again, in many preferred embodiments, rather than the labeling the groupings of parameters or settings 815, 840 used to provide stimulation with letters (e.g., W, X, Y, Z in the figure), they may instead be labeled by a grouping number, grouping name, or any other labeling scheme or plan, which indicates to the clinician, physician, or technician which grouping of settings or parameters is represented. Preferably, the groupings are cross-referenced within the app, software and/or GUI such that a user, clinician, physician or technician may readily and easily be able to see what parameters or settings correspond to the chosen grouping label. The expanded example map view 825 portrays a new combination tab 830, which represents the combination of tabs A and B. This combination tab 830 represents the combination of the disorder and/or symptom response or severity maps for tasks or activities A and B, and the combination can be of any mathematical variety such as averaging, weighted averaging, or the like.

The combination task tab 830 is a result of the user selecting those two disorder and/or symptom response or severity maps to be combined together and optimized in some mathematical way (e.g., averaging) in order to show the results of how the symptom response to each task or series of variables and inputs combine in order to optimize the treatment or therapy settings as well as other constraints. In other words, the goal is to minimize the level of treatment or therapy while simultaneously minimizing the subject's disorders and/or symptoms and/or the severity of the subject's disorders and/or symptoms and/or side effects. Combining the disorder and/or symptom response or severity maps for each task or activity or group of parameters and variables allows the user to see a combined result and select the treatment or therapy settings or parameters that are as close to optimal as possible. In a preferred embodiment, the system would be designed to be a closed-loop system, (i.e., for an implanted home-diagnostic and therapeutic device), which would not require extensive, or any, user input, but would perform the optimization automatically.

Figure 9:
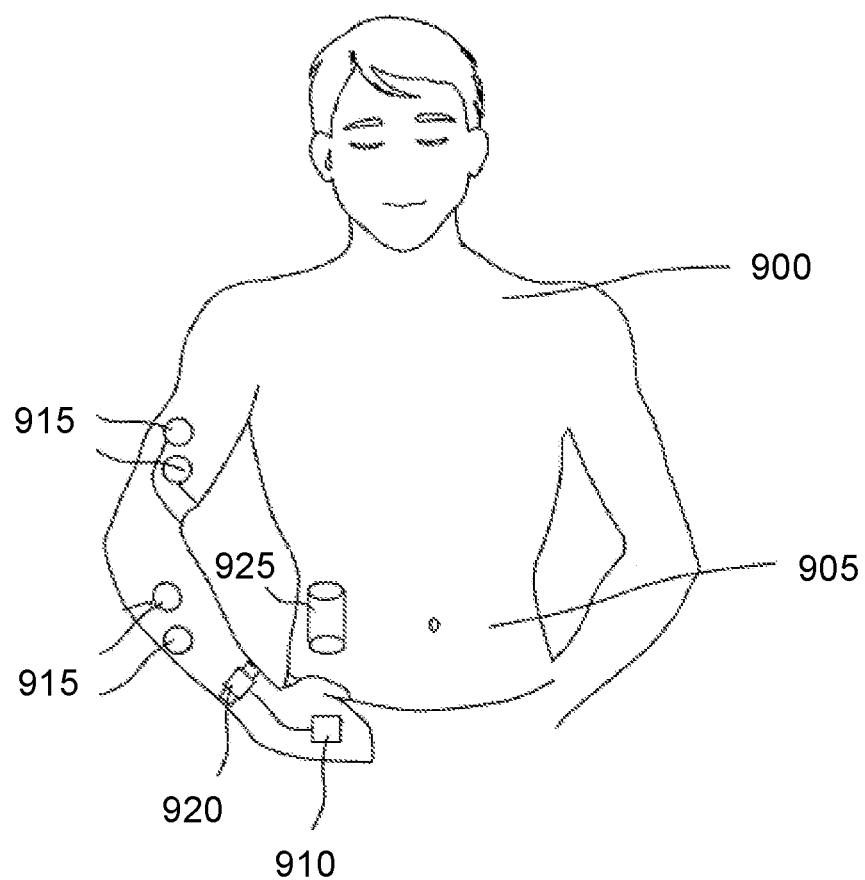
FIG. 9. Depiction of an optional treatment or therapy device that can be used in conjunction with the monitoring device of the present invention comprising an implanted treatment or therapy delivery system.

FIG. 9 is a diagram showing placement of various components of closed loop or semi-closed loop drug delivery system with drug or medication reservoir that can be used as a treatment or therapy device in conjunction with the monitoring device of the present invention. The system includes all of the components for measuring the subject's body movement, including, but not limited to, a sensors 915 and/or sensor modules 910, and a processing device 920 depicted as a smartwatch which may or may not be connected to or in communication with a smartphone (not shown), and adds a treatment or therapy device in the form of a drug delivery system 925, which includes a reservoir for holding medication or a drug with an embedded transceiver (not shown) and processor (not shown) and actuator (not shown) for allowing the drug delivery device to receive commands to dispense a certain amount of the drug, and a controller (not shown) for activating and deactivating the actuator based in part on the signal from the sensor(s) or processing device. In the depicted embodiment, a drug delivery device 925 is shown as implanted into the abdomen 905 of the subject 900. Alternatively, the drug delivery device 925 may be external and can be worn or attached to the subject by any device or methods known to those of skill in the art. The drug delivery device 925 contains a drug or medication, which is released into the subject's 900 body through activation of an actuator (not shown). This drug dispensing function is preferably initiated by the processing device 920 when it detects or makes a determination, via the embedded algorithms for processing the measured and calculated movement data, that the subject is experiencing symptoms of a disability that warrants pharmaceutical intervention. All components can be in wired or wireless communication. Such embodiments can be fully closed-loop wherein control of the drug or medication delivery is controlled solely by the output of the processing device and its algorithms based on the measured and calculated or estimated measures or metrics, or can be semi-closed loop such that intervention, preferably by a clinician who may be located remotely, is either required or allowed in order to trigger the drug or medication delivery based on the output of the system and algorithm.

Figure 10:
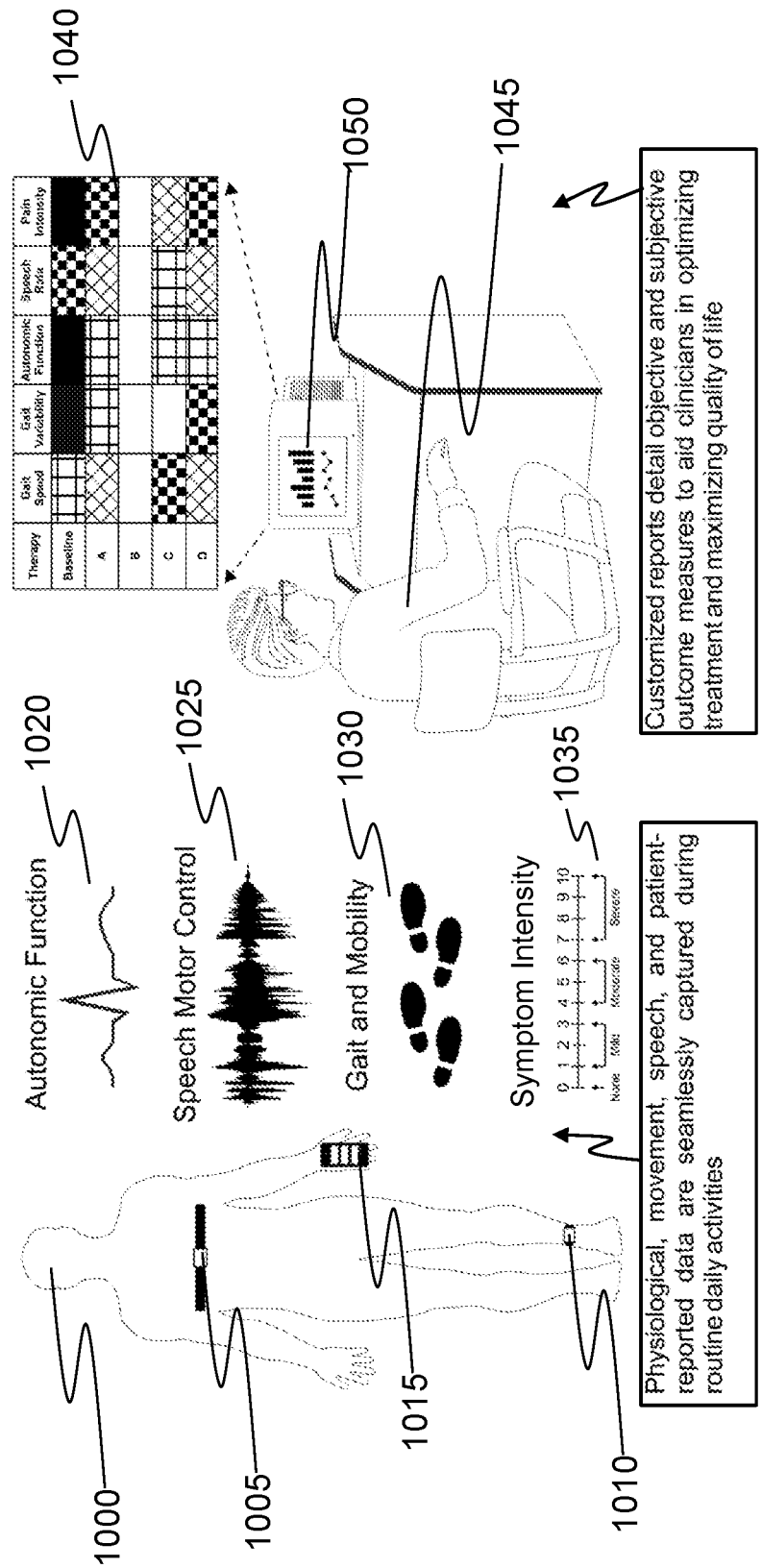
FIG. 10. Pictorial overview of operation of the system of the present invention whereby a subject's physiological status and movement are monitored and processed, and the system outputs a pain response report, where, optionally, a clinician reviews the reports for optimization of the treatment or therapy provided to the subject.

FIG. 10 presents a general overview of the function of the monitoring device of the present invention and the output of the system related to the subject's quantified level or severity of disorders and/or symptoms based on the subject's measured and monitored movement or other sensor signals. The subject 1000 dons the subject-worn monitoring device which comprises at least one (two are depicted, many more are possible) sensor or sensor unit 1005 and 1010. When the monitoring period begins or monitoring is otherwise initiated, the sensors 1005 and 1010 measure the subject's movement based on the particular sensor that is used (e.g., accelerometer, gyroscope, and/or other sensor(s) as disclosed herein) and transmit their measurements to a processing device 1015 which can be any processing device as described herein, but which is depicted as a smartphone. This system can record measurements and metrics from numerous domains for physiological and movement characteristics, including autonomous physiological signals 1020 (e.g., electromyogram (EMG), electrocardiogram (ECG), electroencephalogram (EEG), galvanic skin response, hear rate, and the like), speech motor control signals 1025, gait and mobility-related measurements 1030 as well as movement of other extremities or parts of the body, and symptom intensity 1035 (e.g., patient self-reporting or recording). Many measures or metrics utilized by the system fit into at least one of these domains or categories, and the domains are merely intended to be exemplary of the various forms and groupings of data the system utilizes. Once the system processes the measured and calculated or estimated metrics or measures, it generates an output related to the amount of symptoms or disability the subject 1000 experienced or is experiencing during the monitoring period. The output can be in many forms including a numerical quantified symptom index or score value, a visual representation of numerous iterations of variables and results, audio output, or any combination thereof. In the present figure, the output is depicted as a report 1040 that indicates value of several measures or metrics (gait speed, gait variability, autonomic function, speech rate, and symptom intensity) during various tasks or activities (baseline and Task or Activity A through D). This report is output onto a display 1050 for review and analysis by a clinician, physician or technician 1045 who can then determine severity of the disorders and/or symptoms the subject is experiencing, what is most directly contributing to the disorders and/or symptoms, and what the best form of treatment or therapy is to address the subject's disorders and/or symptoms.

Figure 11:
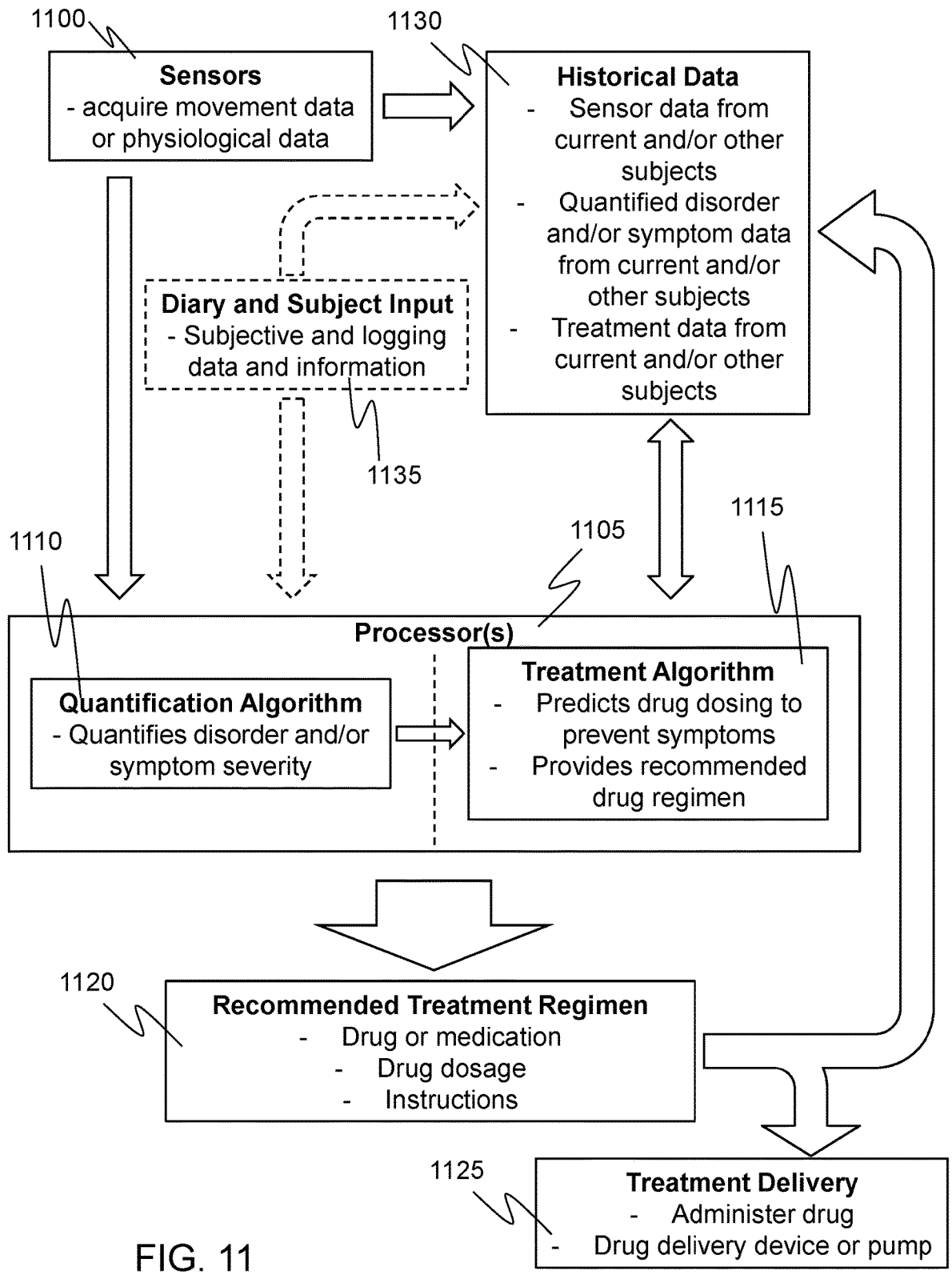
FIG. 11. Block diagram depicting various elements and steps of precision or personal drug dosing system and method embodiments of the present invention.

FIG. 11 is a block diagram depicting various elements and steps of precision or personal drug dosing system and method embodiments of the present invention. Such systems comprise at least one sensor 1100 which is adapted to acquire data from the subject. Such sensors 1100 can be of any variety described herein, including but not limited to movement sensors, physiological sensors, electrophysiological sensors, audio sensors, video sensors, and combinations thereof. These sensor(s) 1100 are used to acquire various signals from the subject, or data related to the sensor signals, in order to measure, monitor, track, or otherwise acquire data related to some condition, aspect, movement, activity, or other characteristic of the subject. Many embodiments include at least one sensor 1100 to measure the subject's movement, or from which movement data may be derived (e.g., physiological or electrophysiological sensors such as EMG or EEG). Acquired sensor 1100 data is then at least transmitted, either via wired or wireless communication methods as described herein, to at least one processor 1105. Preferably, and in many embodiments, the sensor 1100 data may also be transmitted via similar methods to a local, central, or cloud database, and thus made part of a historical data 1130 database, for storage and access at a later time. Other data, generally subjective and other subject input data 1135, such as diary and/or other data input to the system such as via the GUI (not show) of a device that is part of the system, is also handled in a similar manner and input into the algorithm(s) as well as transmitted to a database, and thus made part of a historical data 1130 database, for storage and access. As noted above, subject input data 1135 content depends on the input, but may include subject scores and qualitative assessments of disorders and/or symptoms, habits, activities, medication information (e.g., drugs taken, timing, doses, conditions under which taken, etc.), sleep quality and habit information, and the like. Whatever data is input into the system, whether sensors 1100 based or subject based 1135), the data is preferably transmitted to one or more processors 1105 for processing and analysis. Such processing may include any preprocessing of signals (e.g., filtering, analog-to-digital conversion, etc.), or such preprocessing may be performed at the sensor 1100 or sensor device or module. A single processor 1105 may be utilized, though some embodiments may utilize multiple devices which may each have separate processors 1105. The processor(s) 1105 are used to perform any necessary analysis of the acquired sensor 1100 data and/or subject input data 1135. Many embodiments comprise a quantification algorithm 1110 employed by at least one of the at least one processor(s) 1105. The quantification algorithm(s) 1110 analyze and process the sensor 1100 data and/or subject input data 1135, along with historical data 1130 from the current subject and/or other subjects, in order to quantify the level or severity of the subject's disorders and/or symptoms. The quantification may be a score, either arbitrarily scaled for purposes of a particular embodiment or correlated to a standardize scale (e.g., UPDRS, AIMS, Wong-Baker FACES scale, or the like). This quantification may be displayed to the subject or a physician, clinician, or technician, or may be kept internal to the system and merely transmitted to the next phase. Where the quantification is displayed, it may be displayed as a numerical index, a symptom response map, a symbol or message (visual or audio), and may be stylized to indicate relative severity or a severity value above or below a desired threshold. The quantification algorithm 1110 provides a quantified severity of the subject's disorders and/or symptoms, and that quantification is then input into a treatment algorithm 1115. The treatment algorithm 1115 is adapted to provide a recommended treatment protocol or regimen to specifically address the particular subject's needs based on the data input, sensor 1100 data and/or subject input data 1135, the output of the quantification algorithm 1110, and historical data 1130 from the current subject and/or other subjects. Both the quantification algorithm 1110 output and the treatment algorithms 1115 output are also preferably transmitted to a database and included in historical data 1130 databases for storage and future access. The output of the treatment algorithm 1115 is preferably a recommended treatment regimen or protocol 1120 comprising a recommended drug, including dosing and instructions for administering the drug, but may also be an alternative form of therapy or parameters or settings for a different therapy (e.g., DBS, FES, tDCS, etc.). The recommended treatment regimen or protocol 1120 may also include, additionally or in the alternative, action recommendations where the subject is provided with suggested exercises, activities, movements, stretches, dietary changes or suggestions, suggestions regarding environmental changes, or the like, to help address the determined level or severity of disorders and/or symptoms. Preferably, particularly for embodiments where the recommended treatment or therapy is pharmaceutical based, the recommended treatment regimen or protocol 1120 adapted to provide a precision or personal drug regimen or protocol. Precision drug regimens or protocols, as described herein, preferably involve the treatment algorithm further being adapted to predict the onset or recurrence of a subject's disorders and/or symptoms and to recommend a drug regimen or protocol that is adapted to prevent such occurrence or recurrence. Effectively, the precision drug regimen or protocol enables the proper drug and dose to be administered at precisely the right time in order to maintain an optimal or desired drug profile in the subject's bloodstream to maximize the effectiveness and effective time period of the drug for the subject and to reduce off time where the subject is not enjoying the benefits of the medication treatment or therapy. The precision drug regimen or protocol can also be accompanied by action recommendations as described above that help to further alleviate the subject's disorders and/or symptoms or to increase the effectiveness of the drug treatment or therapy. The recommended treatment regimen or protocol 1120 is then provided as an output at least to a treatment delivery system 1125, and also preferably to a historical data 110 database for storage and later access. The treatment delivery 1125 system can be of any type disclosed herein. The depicted embodiment is directed to delivery of medication or drugs, preferably according to a precision dosing regimen or protocol, where the recommended treatment regimen or protocol 1120 can be implemented for self-administered (e.g., pills, applications of transdermal patches, some injections, etc.) or human-administered (e.g., given by a clinician, physician, or technician) drugs or medications, or for semi-automated (e.g., semi-automated pill boxes or drug dispensers that make the medication available to the subject at the recommended or desired time) or automated drug delivery systems (e.g., external or implanted drug pumps and the like). The treatment delivery 1125 system, particularly for self-administered therapies, preferably involves the display or notification of the desired or recommended drug, dose, and instructions to the subject, such as via a GUI of a device of the system, such that the subject can repeatedly consult the recommended treatment regimen or protocol 1120 to ensure proper and safe administration of the pharmaceutical treatment or therapy. As noted, the recommended treatment regimen or protocol 1120 is preferably also transmitted to a historical data 1135 database for storage and or later access, such as for review by a clinician, physician, or technician, or by the system to use as input for the algorithm(s). Further, the recommended treatment regimen or protocol 1120 may be output immediately to a display (not shown) for a clinician, physician, or technician to review and approve or edit prior to being output to the subject's treatment delivery 1125 device.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claimed is:

1. A precision or personal drug or medication dosing system comprising:
 at least one movement sensor adapted to acquire movement data or the movement data derived from at least one physiological sensor, the movement data related to a first subject's external body motion;
 at least one processor adapted for processing the movement data;
 a quantification algorithm adapted to quantify symptom severity and to calculate a quantification score of at least one symptom based at least in part on the movement data; and
 a treatment algorithm adapted to predict when a drug or medication should be administered to prevent an increase in the symptom severity based in part on early detection of changes in the symptom severity and a historical data of at least the first subject and/or other subjects, and to provide a recommended drug or medication regimen comprising the drug, a drug dosage, and/or instructions for administration of the drug and/or the drug dosage, the recommended drug or medication regimen based at least in part on the calculated quantification score,
 wherein at least the quantification and treatment algorithms are trained at least in part on reference data of the first subject and/or the other subjects, the reference data comprising:
  historical movement data collected using at least one historical movement sensor or a historical physiological sensor corresponding to historical movement of the first subject and/or the other subjects, and at least one type of data from the group consisting of:
  clinician scores or sensor-based symptom quantification scores corresponding to the historical movement data, and
  treatment parameters for the first subject and/or the other subjects corresponding to the historical movement data, and
 further wherein the recommended drug or medication regimen is adapted to provide a desired drug profile in a bloodstream of the first subject, and the system is further adapted to recommend or provide a new or additional drug dose based on the quantified symptom severity in order to prevent an onset or recurrence of the at least one symptom, the desired drug profile adapted to be maintained within ±75% of a blood concentration or a desired threshold value corresponding to the desired drug profile in the bloodstream of the first subject.

2. The system of claim 1, wherein the treatment algorithm is further adapted to provide the recommended drug or medication regimen based on a constraint of minimizing the drug dose by providing one or more of the drug doses at a time adapted to prevent an increase in the quantification of the at least one symptom.

3. The system of claim 1, further comprising a treatment algorithm output adapted for outputting the recommended drug or medication regimen to a drug delivery device for adjusting settings or parameters of the drug delivery device for administration of the drug or medication according to the recommended drug or medication regimen.

4. The system of claim 3, further comprising an actuator adapted to open a pill box or dispense from a dispensing device the drug dose or the new or additional drug dose to be made available to the first subject for manual self-administration according to the recommended drug or medication regimen, the dispensing device not being a drug pump.

5. The system of claim 3, wherein the treatment algorithm is further adapted to provide an action recommendation corresponding to a suggested activity, exercise, diet, and/or environmental condition to prevent the onset or recurrence of the at least one symptom.

6. The system of claim 3, wherein the treatment algorithm output is further adapted for outputting the recommended drug or medication regimen to a graphic user interface (GUI) adapted to display the recommended drug or medication regimen to the subject and/or a clinician, physician, or technician for administration of the or another drug or medication according to the recommended drug or medication regimen.

7. The system of claim 6, wherein the recommended drug or medication regimen is reviewed by the or another clinician, physician or technician and approved or amended prior to displaying the recommended drug or medication regimen to the subject for administration.

8. A precision or personal drug or medication dosing system comprising:
 at least one movement sensor adapted to acquire movement data or the movement data derived from at least one physiological sensor, the movement data related to a first subject's external body motion;
 at least one processor adapted for processing the movement data;
 a quantification algorithm adapted to quantify symptom severity and to calculate a quantification score of at least one symptom based at least in part on the movement data; and
 a treatment algorithm adapted to predict when a drug or medication should be administered to prevent an increase in the symptom severity based in part on early detection of changes in the symptom severity and a historical data of at least the first subject and/or other subjects, to provide a recommended drug or medication regimen comprising the drug, a drug dosage, and/or instructions for administration of the drug and/or the drug dosage, the recommended drug or medication regimen based at least in part on the calculated quantification score, and to further provide an action recommendation corresponding to a suggested activity, exercise, diet, and/or environmental condition to prevent an onset or recurrence of the at least one symptom, wherein the recommended drug or medication regimen is adapted to provide a desired drug profile in a bloodstream of the first subject, and the system is further adapted to recommend or provide a new or additional drug dose based on the quantified symptom severity in order to prevent an onset or recurrence of the at least one symptom based on a constraint of minimizing the drug dose and/or the new or additional drug dose by providing the one or more of the drug doses at a time adapted to prevent an increase in the quantification of the at least one symptom, and at least the quantification and treatment algorithms are trained at least in part on reference data of the first subject and/or the other subjects, the reference data comprising:

historical movement data collected using at least one historical movement sensor or a historical physiological sensor corresponding to historical movement of the first subject and/or the other subjects, and at least one type of data from the group consisting of:

clinician scores or sensor-based symptom quantification scores corresponding to the historical movement data, and treatment parameters for the first subject and/or the other subjects corresponding to the historical movement data, wherein the desired drug profile is adapted to be maintained within ±75% of a blood concentration or a desired threshold value corresponding to the desired drug profile in the bloodstream of the first subject.

\* \* \* \* \*